United States Patent
Zahler et al.

(10) Patent No.: US 9,944,613 B2
(45) Date of Patent: Apr. 17, 2018

(54) FUMAGILLOL SPIROCYCLIC COMPOUNDS AND FUSED BICYCLIC COMPOUNDS AND METHODS OF MAKING AND USING SAME

(71) Applicant: Zafgen, Inc., Boston, MA (US)

(72) Inventors: Robert Zahler, Pennington, NJ (US); Zhenwei Cai, Skillman, NJ (US); Zhixing Wu, Pudong Shanghai (CN); James E. Vath, Lynnfield, MA (US)

(73) Assignee: Zafgen, Inc., Boston, MA (US)

( * ) Notice: Subject to any disclaimer, the term of this patent is extended or adjusted under 35 U.S.C. 154(b) by 0 days.

(21) Appl. No.: 15/827,074

(22) Filed: Nov. 30, 2017

(65) Prior Publication Data

US 2018/0079737 A1    Mar. 22, 2018

Related U.S. Application Data

(63) Continuation of application No. PCT/US2016/046515, filed on Aug. 11, 2016.

(60) Provisional application No. 62/210,102, filed on Aug. 26, 2015.

(30) Foreign Application Priority Data

Aug. 11, 2015  (CN) .......................... 2015 1 0490559

(51) Int. Cl.
| | |
|---|---|
| *A61K 31/336* | (2006.01) |
| *A61K 31/195* | (2006.01) |
| *C07D 303/04* | (2006.01) |
| *C07D 491/107* | (2006.01) |
| *C07D 491/08* | (2006.01) |
| *C07D 491/048* | (2006.01) |
| *C07D 495/10* | (2006.01) |
| *C07D 487/10* | (2006.01) |
| *C07D 407/06* | (2006.01) |
| *C07D 405/14* | (2006.01) |
| *C07D 401/14* | (2006.01) |
| *C07D 487/04* | (2006.01) |

(52) U.S. Cl.
CPC .......... *C07D 303/04* (2013.01); *A61K 31/195* (2013.01); *A61K 31/336* (2013.01); *C07D 401/14* (2013.01); *C07D 405/14* (2013.01); *C07D 407/06* (2013.01); *C07D 487/04* (2013.01); *C07D 487/10* (2013.01); *C07D 491/048* (2013.01); *C07D 491/08* (2013.01); *C07D 491/107* (2013.01); *C07D 495/10* (2013.01); *A61K 2300/00* (2013.01)

(58) Field of Classification Search
None
See application file for complete search history.

(56) References Cited

U.S. PATENT DOCUMENTS

| | | | |
|---|---|---|---|
| 5,164,410 A | 11/1992 | Kishimoto et al. | |
| 5,166,172 A | 11/1992 | Kishimoto et al. | |
| 5,180,735 A | 1/1993 | Kishimoto et al. | |
| 5,180,738 A | 1/1993 | Kishimoto et al. | |
| 5,196,406 A | 3/1993 | Kamei et al. | |
| 5,204,345 A | 4/1993 | Kishimoto et al. | |
| 5,288,722 A | 2/1994 | Kishimoto et al. | |
| 5,290,807 A | 3/1994 | Folkman et al. | |
| 5,422,363 A | 6/1995 | Yanai et al. | |
| 5,536,623 A | 7/1996 | Ohmachi et al. | |
| 5,698,586 A | 12/1997 | Kishimoto et al. | |
| 5,767,293 A | 6/1998 | Oku et al. | |
| 5,846,562 A | 12/1998 | Yanai et al. | |
| 5,900,431 A | 5/1999 | Molina et al. | |
| 6,017,949 A | 1/2000 | D'Amato et al. | |
| 6,017,954 A | 1/2000 | Folkman et al. | |
| 6,040,337 A | 3/2000 | Hong, II et al. | |
| 6,063,812 A | 5/2000 | Hong et al. | |
| 6,180,626 B1 | 1/2001 | Shimomura et al. | |
| 6,207,704 B1 | 3/2001 | Liu et al. | |
| 6,242,494 B1 | 6/2001 | Craig et al. | |
| 6,277,391 B1 | 8/2001 | Seo et al. | |
| 6,306,819 B1 | 10/2001 | Rupnick et al. | |
| 6,323,228 B1 | 11/2001 | BaMaung et al. | |
| 6,383,471 B1 | 5/2002 | Chen et al. | |
| 6,548,477 B1 | 4/2003 | Olson et al. | |
| 6,566,541 B2 | 5/2003 | Liu et al. | |
| 6,664,244 B1 | 12/2003 | Furuse et al. | |
| 6,803,382 B2 | 10/2004 | Eustache et al. | |
| 6,877,863 B2 | 4/2005 | Wood et al. | |
| 6,989,392 B2 | 1/2006 | Collins et al. | |
| 7,030,262 B2 | 4/2006 | BaMaung et al. | |
| 7,037,890 B2 | 5/2006 | Olson et al. | |
| 7,084,108 B2 | 8/2006 | Olson et al. | |
| 7,268,111 B2 | 9/2007 | Olson et al. | |
| 7,304,082 B2 | 12/2007 | Marino, Jr. et al. | |
| 7,718,695 B2 | 5/2010 | Kim et al. | |
| 8,367,721 B2 | 2/2013 | Hughes et al. | |
| 8,642,650 B2 | 2/2014 | Hughes et al. | |
| 8,980,946 B2 | 3/2015 | Hughes | |
| 9,000,035 B2 | 4/2015 | Hughes | |
| 9,173,865 B2 | 11/2015 | Hughes | |
| 9,573,918 B2 | 2/2017 | Zahler et al. | |
| 9,682,965 B2 | 6/2017 | Vath et al. | |

(Continued)

FOREIGN PATENT DOCUMENTS

| | | | |
|---|---|---|---|
| EP | 0354787 A1 | 2/1990 | |
| EP | 0682020 A1 | 11/1995 | |

(Continued)

OTHER PUBLICATIONS

U.S. Pat. No. 9,573,918, Issued on Feb. 21, 2017; U.S. Appl. No. 14/399,392; published as US 2015-0126489 A1 on May 7, 2015, Fumagillol Compounds and Methods of Making and Using Same, filed Nov. 6, 2014.

(Continued)

*Primary Examiner* — Samantha L Shterengarts
(74) *Attorney, Agent, or Firm* — Goodwin Procter LLP

(57) ABSTRACT

Disclosed herein, in part, are fumagillol compounds and methods of use in treating medical disorders, such as obesity. Pharmaceutical compositions and methods of making fumagillol compounds are provided. The compounds are contemplated to have activity against methionyl aminopeptidase 2.

14 Claims, No Drawings

(56) References Cited

U.S. PATENT DOCUMENTS

| | | |
|---|---|---|
| 2003/0220371 A1 | 11/2003 | Kallander et al. |
| 2004/0067266 A1 | 4/2004 | Toppo |
| 2004/0116495 A1 | 6/2004 | Marino, Jr. et al. |
| 2004/0157836 A1 | 8/2004 | Comess et al. |
| 2004/0167128 A1 | 8/2004 | Comess et al. |
| 2004/0204472 A1 | 10/2004 | Briggs et al. |
| 2005/0037994 A1 | 2/2005 | Kim et al. |
| 2005/0239878 A1 | 10/2005 | Thompson et al. |
| 2006/0045865 A1 | 3/2006 | Jacob et al. |
| 2006/0069161 A1 | 3/2006 | Lee et al. |
| 2006/0276512 A1 | 12/2006 | Han et al. |
| 2007/0078172 A1 | 4/2007 | McElroy et al. |
| 2008/0200402 A1 | 8/2008 | Alvinerie et al. |
| 2009/0148396 A1 | 6/2009 | Akullian et al. |
| 2010/0016425 A1 | 1/2010 | Vath |
| 2010/0111894 A1 | 5/2010 | Benny-Ratsaby et al. |
| 2012/0004162 A1 | 1/2012 | Vath |
| 2012/0010259 A1 | 1/2012 | Vath |
| 2012/0010290 A1 | 1/2012 | Vath |
| 2012/0034233 A1 | 2/2012 | Hughes et al. |
| 2012/0322867 A1 | 12/2012 | Hughes et al. |
| 2013/0316994 A1 | 11/2013 | Hughes |
| 2014/0011870 A1 | 1/2014 | Hughes |
| 2014/0045934 A1 | 2/2014 | Hughes |
| 2014/0045935 A1 | 2/2014 | Hughes |
| 2014/0051752 A1 | 2/2014 | Hughes |
| 2014/0336251 A1 | 11/2014 | Hughes et al. |
| 2015/0150840 A1 | 6/2015 | Vath |
| 2015/0150857 A1 | 6/2015 | Vath |
| 2015/0209320 A1 | 7/2015 | Hughes et al. |
| 2015/0335608 A1 | 11/2015 | Hughes et al. |
| 2015/0361061 A1 | 12/2015 | Vath |

FOREIGN PATENT DOCUMENTS

| | | |
|---|---|---|
| WO | WO-1998/056372 A1 | 12/1998 |
| WO | WO-1999/039702 A2 | 8/1999 |
| WO | WO-1999/057097 A2 | 11/1999 |
| WO | WO-1999/059986 A1 | 11/1999 |
| WO | WO-1999/059987 A1 | 11/1999 |
| WO | WO-2000/064876 A1 | 11/2000 |
| WO | WO-2002/026782 A2 | 4/2002 |
| WO | WO-2002/042295 A2 | 5/2002 |
| WO | WO-2002/083065 A2 | 10/2002 |
| WO | WO-2003/027104 A1 | 4/2003 |
| WO | WO-2003/082845 A1 | 10/2003 |
| WO | WO-2004/033419 A1 | 4/2004 |
| WO | WO-2005/066197 A2 | 7/2005 |
| WO | WO-2005/082349 A1 | 9/2005 |
| WO | WO-2006/010498 A2 | 2/2006 |
| WO | WO-2006/080591 A1 | 8/2006 |
| WO | WO-2009/073445 A2 | 6/2009 |
| WO | WO-2010/042163 A2 | 4/2010 |
| WO | WO-2010/048499 A1 | 4/2010 |
| WO | WO-2010/065877 A2 | 6/2010 |
| WO | WO-2010/065879 A2 | 6/2010 |
| WO | WO-2010/065881 A2 | 6/2010 |
| WO | WO-2010/065883 A2 | 6/2010 |
| WO | WO-2011/044506 A2 | 4/2011 |
| WO | WO-2011/085198 A1 | 7/2011 |
| WO | WO-2011/085201 A1 | 7/2011 |
| WO | WO-2011/088055 A2 | 7/2011 |
| WO | WO-2011/127304 A2 | 10/2011 |
| WO | WO-2011/150338 A1 | 12/2011 |
| WO | WO-2012/012642 A1 | 1/2012 |
| WO | WO-2012/064838 A1 | 3/2012 |
| WO | WO-2012/051318 A1 | 4/2012 |
| WO | WO-2012/064928 A1 | 5/2012 |
| WO | WO-2012/074968 A1 | 6/2012 |
| WO | WO-2012/075020 A1 | 6/2012 |
| WO | WO-2012/075026 A1 | 6/2012 |
| WO | WO-2012/103333 A1 | 8/2012 |
| WO | WO-2012/122264 A1 | 9/2012 |
| WO | WO-2012/154676 A1 | 11/2012 |
| WO | WO-2012/154678 A1 | 11/2012 |
| WO | WO-2012/154679 A1 | 11/2012 |
| WO | WO-2013/033430 A1 | 3/2013 |
| WO | WO-2013/055385 A2 | 4/2013 |
| WO | WO-2013/109735 A1 | 7/2013 |
| WO | WO-2013/109739 A1 | 7/2013 |
| WO | WO-2013/169727 A1 | 11/2013 |
| WO | WO-2013/169860 A1 | 11/2013 |

OTHER PUBLICATIONS

U.S. Appl. No. 15/399,071, Fumagillol Compounds and Methods of Making and Using Same, filed Jan. 5, 2017.
U.S. Pat. No. 9,682,965; Issued Jun. 20, 2017; U.S. Appl. No. 15/354,834; published as US 2017-0066749 A1 on Mar. 9, 2017, Fumagillol Heterocyclic Compounds and Methods of Making and Using Same, filed Nov. 17, 2016.
U.S. Appl. No. 15/596,512, Fumagillol Heterocyclic Compounds and Methods of Making and Using Same, filed May 16, 2017.
Anderson, "The Use of Fumagillin in Amoebiasis," Annals of the New York Academy of Sciences, 55:1118-1124, 1952.
Benny et al., "An Orally Delivered Small-Molecule Formulation with Antiangiogenic and Anticancer Activity," Nat Biotechnol. Jul. 2008;26(7):799-807.
Bernier et al.,"Fumagillin class inhibitors of methionine aminopeptidase-2," Drugs of the Future 30(5):497-500, 2005.
Brakenhielm et al., "Angiogenesis Inhibitor, TNP-470, Prevents Diet-Induced and Genetic Obesity in Mice" Circulation Research, http://circres.ahajournals.org (accessed on Feb. 8, 2007), 2004.
Braunwald et al., "Obesity" in Harrison's Principles of Internal Medicine, 15th Ed., McGraw Hill (New York) pp. 479-486, 2001.
Butler et al., "Clinical Findings and Natural History of Prader-Willi Syndrome," Chapter 1; Clinical Findings and Natural History of PWS, pp. 3-48 (2006).
Cassidy et al., "Prader-Willi syndrome," European Journal of Human Genetics 17:3-13 (2009).
Cassidy et al., "Prader-Willi syndrome," Genetics in Medicine, vol. 14(1) pp. 10-26 (2012).
Cataletto et al., "Prader-Willi syndrome: A primer for clinicians," International Journal of Pediatric Endocrinology, vol. 12:1-13 (2011).
Chun et al., "Novel inhibitors targeted to methionine aminopeptidase 2 (MetAP2) strongly inhibit the growth of cancers in xenografted nude model," Int J Cancer. Mar. 10, 2005;114(1):124-30.
Didier et al., "Antimicrosporidial Activities of Fumagillin, TNP-470, Ovalicin, and Ovalicin Derivatives in Vitro and In Vivo" Antimicrob Agents Chemother. Jun. 2006;50(6):2146-55.
DiPaolo et al.,"Studies on the Carcinolytic Activity of Fumagillin and Some of its Derivatives," Antibiot Annu.1958-1959;6:541-6.
Drevs et al.,"Antiangiogenic Potency of FK866/K22.175, a New Inhibitor of Intracellular NAD Biosynthesis, in Murine Renal Cell Carcinoma," Anticancer Res. Nov.-Dec. 2003;23(6C):4853-4858.
Dumas et al., "Synthesis and Structure Activity Relationships of Novel Small Molecule Cathepsin D Inhibitors" Bioorg Med Chem Lett. Sep. 6, 1999;9(17):2531-6.
Dykens et al., "Assessment of Hyperphagia in Prader-Willi Syndrome," Obesity 15:7 (2007).
Eder et al., "Phase 1 Dose Escalation Safety & Tolerance Study of PPI-2458 in Subjects with Non-Hodgkin's Lymphoma or Solid Tumors" (Presented on Nov. 7-10, 2006 at EORTC-NCI-AACR Symposium on "Molecular Targets and Cancer Therapeutics.").
Edgar et al., "Body composition in Prader-Willi syndrome compared with nonsyndromal obesity: Relationship to physical activity and growth homrone function," The Journal of Pediatrics 139:5, 708-714 (2001).
Einfield et al., "Mortality in Prader-Willi Syndrome," Am. J. Ment. Retard. 111(3):193-198 (2006).
European Communication for EP Application No. 12 798 444.1, dated Aug. 28, 2015 (8 pages).
European Search Report for EP 09798793 dated Oct. 11, 2011, 9 pages.

(56) References Cited

OTHER PUBLICATIONS

Evdokimov et al., "Serendipitious discovery of novel bacterial methionine aminopeptidase inhibitors," Proteins Feb. 15; 66(3):538-546 (2007).
Everhart, "Contributions of Obesity and Weight Loss to Gallstone Disease" Ann Intern Med. Nov. 15, 1993;119(10):1029-35.
Garrabrant et al.,"Small molecule inhibitors of methionine aminopeptidase type 2 (MetAP-2) fail to inhibit endothelial cell proliferation or formation of microvessels from rat aortic rings in vitro" Angiogenesis. 2004;7(2):91-6.
Garrison et al., "A metabolic basis for fibromyalgia and its related disorders: the possible role of resistance to thyroid hormone," Med. Hypotheses. Aug;61(2):182-189 (2003).
Han et al., "Design and Synthesis of Highly Potent Fumagillin Analogues from Homology Modeling for a Human MetAP-2," Bioorg Med Chem Lett. Jan. 3, 2000;10(1):39-43.
Holland et al., "The paradoc of Prader-Willi syndrome: a genetic model of starvation," The Lancet 362, 989-991 (2003).
Huang et al., "Inhibition of Monometalated Methionine Aminopeptidase: Inhibitor Discovery and Crystallographic Analysis," J. Med. Chem., Nov. 15;50(23):5735-5742 (2007).
Ingber et al., "Synthetic Analogues of Fumagillin that Inhibit Angiogenesis and Suppress Tumour Growth," Nature, 348(6301):555-557 (1990).
International Search Report for International Application No. PCT/US2011/020515, International Filing Date Jul. 1, 2011, 4 pages.
International Search Report for International Application No. PCT/US2011/020866, dated Jul. 22, 2011, 8 pages.
International Search Report for International Application No. PCT/US2011/060127, dated Jan. 2, 2012, 2 pages.
International Search Report for International Application No. PCT/US2011/062320, dated Feb. 17, 2012, 3 pages.
International Search Report for International Application No. PCT/US2011/062421, dated Feb. 17, 2012, 3 pages.
International Search Report for International Application No. PCT/US2011/38352, International Filing Date May 27, 2011,3 pages.
International Search Report for International Application No. PCT/US2012/000461, dated May 2, 2013, 7 pages.
International Search Report for International Application PCT/US2010/052050, dated Mar. 25, 2011, 3 pages.
Jauregi et al., "Behavioral profile of adults with Prader-Willi syndrome: correlations with individual and environmental variables," Journal of Neurodevelopmental Disorders 5:18, 1-10 (2013).
Jeong et al, "Total synthesis and antiangiogenic activity of cyclopentane analogues of fumagillol" Bioorg Med Chem Lett. Aug. 1, 2005;15(15):3580-3.
Kawai et al., "Development of Sulfonamide Compounds as Potent Methionine Aminopeptidase Type II Inhibitors with Antiproliferative Properties", Bioorg. Med. Chem. Lett. Jul. 1;16(13):3574-3577 (2006).
Kim et al. "Assessment of the Anti-Obesity Effects of the TNP-470 Analog, CKD-732" J Mol. Endocrinol. Apr. 2007;38(4):455-65.
Kim et al. "Development of parenteral formulation for a novel angiogenesis inhibitor, CKD-732 through complexation with hydroxypropyl-beta-cyclodextrin" Int J Pharm. Mar. 19, 2004;272(1-2):79-89.
Kim et al. "General pharmacology of CKD-732, a new anticancer agent: effects on central nervous, cardiovascular, and respiratory system" Biol Pharm Bull. Feb. 2005;28(2):217-23.
Kim et al., "Depletion of Methionine Aminopeptidase 2 does not Alter Cell Response to Fumagillin or Bengamides," Cancer Res., May 1;64(9):2984-2987 (2004).
Kruger, "TNP-470: An Angiogenesis Inhibitor in Clinical Development for Cancer" Expert Opin Investig Drugs. Jun. 2000;9(6):1383-96.
Lee et al. "Absorption, distribution, metabolism, and excretion of CKD-732, a novel antiangiogenic fumagillin derivative, in rats, mice, and dogs" Arch Pharm Res. Feb. 2004;27(2):265-72.

Lee et al. "Design, Synthesis, and Antiangiogenic Effects of a Series of Potent Novel Fumagillin Analogues" Chem Pharm Bull (Tokyo). Jul. 2007;55(7):1024-9.
Lee et al. "Selective N-demethylation of tertiary aminofumagillols with selenium dioxide via a non-classical Polonovski type reaction" Heterocycles 68(5):915-932, 2006.
Lijnen et al. "Fumagillin Reduces Adipose Tissue Formation in Murine Models of Nutritionally Induced Obesity" Obesity (Silver Spring). Dec. 2010;18(12):2241-6. doi: 10.1038/oby.2009.503. Epub Jan. 21, 2010.
Luo et al., "Discovery and Structural Modification of Inhibitors of Methionine Aminopeptidases from *Escherichia coli* and *Saccharomyces cerevisiae*," J. Med. Chem. Jun. 19;46(13):2631-2640 (2003).
Ma et al., "Structural Analysis of Inhibition of *E. coli* Methionine Aminopeptidase: Implication of Loop Adaptability in Selective Inhibition of Bacterial Enzymes," BMC Struct Biol., Dec. 19;7:84 (2007).
Masiero et al. "New Anti-angiogenesis Agents: Review of the Clinical Experience with Carboxyamido-Triazole (CAI), Thalidomide, TNP-470 and Interleukin-12" Angiogenesis. 1997;1(1):23-35.
McCowen et al., "Fumagillin (H-3), a New Antibiotic with Amebicidal Properties" Science. Feb. 23, 1951;113(2930):202-3.
Milkowski et al., "TNP-470" Antiangiogenic Agents in Cancer Therapy, Chapter 22 pp. 385-398, 1999.
Miller et al., "Nutritional Phases in Prader-Willi Syndrome," Am. J. Med. Genet. A. 155A(5): 1040-1049 (2011).
Molina et al. "Potential Efficacy of Fumagillin in Intestinal Microsporidiosis Due to Enterocytozoon Bieneusi in Patients with HIV Infection: Results of a Drug Screening Study" AIDS. Nov. 1997;11(13):1603-10.
Molina et al. "Fumagillin Treatment of Intestinal Microsporidiosis" N Engl J Med. Jun. 20, 2002;346(25):1963-9.
Molina, et al. "Trial of Oral Fumagillin for the Treatment of Intestinal Microsporidiosis in Patients with HIV Infection" AIDS. Jul. 7, 2000;14(10):1341-8.
Mosteller, R.D., "Simplified Calculation of Body-surface Area," N. Engl .J. Med., 317(17):1098 (Oct. 22, 1987).
Myung et al. "The identification of in vitro metabolites of CKD-732 by liquid chromatography/tandem mass spectrometry" Rapid Commun Mass Spectrom. 2002;16(21):2048-53.
Naganuma et al. "Metronomic doxifluridine chemotherapy combined with the anti-angiogenic agent TNP-470 inhibits the growth of human uterine carcinosarcoma xenografts" Cancer Sci. Aug. 2011;102(8):1545-52. doi: 10.1111/j.1349-7006.2011.01998.x. Epub Jul. 3, 2011.
National Task Force on the Prevention and Treatment of Obesity "Very low-calorie diets. National Task Force on the Prevention and Treatment of Obesity, National Institutes of Health" JAMA Aug. 25, 1993;270(8):967-74.
Noel et al. "Increased Risk of Acute Pancreatitis and Biliary Disease Observed in Patients with Type 2 Diabetes"Diabetes Care. May 2009;32(5):834-8. doi: 10.2337/dc08-1755. Epub Feb. 10, 2009.
Pagliarulo et al. "Gallstone disease and related risk factors in a large cohort of diabetic patients" Dig. Liver Dis., Feb;36(2):130-134 (2004).
Picoul et al., "Progress in fumagillin synthesis," Pure Appl. Chem. 75(2-3): 235-249 (2003).
Rhee et al., "Angiogenesis inhibitor attenuates parathyroid hormone-induced anabolic effect" Biomed Pharmacother. Jan;63(1):63-68 (2009).
Rupnick et al., "Adipose Tissue Mass Can be Regulated Through the Vasculature," Proc. Natl. Acad. Sci. U.S.A. Aug. 6;99(16):10730-10735 (2002).
Seneca et al., "Amebiasis: a review. II. Laboratory diagnosis, differential diagnosis and therapy," Am. J. Dig. Dis. Jul;1(7):310-322 (1956).
Sheppard et al., "3-Amino-2-Hydroxyamides and Related Compounds as Inhibitors of Methionine Aminopeptidase-2", Bioorg. Med. Chem Lett., Feb. 23;14(4):865-868 (2004).

(56) References Cited

OTHER PUBLICATIONS

Shin et al., "A Phase I Pharmacokinetic and Pharmacodynamic Study of CKD-732, an Antiangiogenic Agent, in Patients with Refractory Solid Cancer," Invest New Drugs Oct;28(5):650-658 (2010).

Shin et al., "A Phase lb pharmacokinetic study of the antiangiogenic agent CKD-732 used in combination with capecitabine and oxaliplatin (XELOX) in metastatic colorectal cancer patients who progressed on irinotecan-based chemotherapy," Invest. New Drugs, Apr;30(2):672-680 (2012).

Srikumar et al., "Structural insights on Brugia malayi transglutaminase with cinnamoyl derivatives—a molecular docking approach," International Journal of Pharma and Bio Sciences 3(3):998-1006 (2012).

Towbin et al., "Proteomics-based target identification: bengamides as a new class of methionine aminopeptidase inhibitors," J. Biol. Chem. 278(52):52964-52971 (2003).

Vedantham et al., "Studies towards the synthesis of methionine aminopeptidase inhibitors: diversification utilizing a ROMP-derived coupling reagent", J Comb Chem. Mar.-Apr.;10(2):195-203 (2008).

Wang et al. "Lead optimization of methionine aminopeptidase-2 (MetAP2) inhibitors containing sulfonamides of 5,6-disubstituted anthranilic acids", Bioorg Med Chem Lett. May 15, 2007;17(10):2817-22. Epub Feb. 25, 2007.

Wang et al. "Tumor Suppression by a Rationally Designed Reversible Inhibitor of Methionine Aminopeptidase-2", Cancer Res. 63:7861-7869, 2003.

Wang et al., "Discovery of inhibitors of *Escherichia coli* methionine aminopeptidase with the Fe(II)-form selectivity and antibacterial activity", J Med Chem. Oct. 9, 2008;51(19):6110-20.

Weinsier et al., "Gallstone Formation and Weight Loss" Obes Res. Jan;1(1):51-56 (1993).

Weinsier et al., "Medically Safe Rate of Weight Loss for the Treatment of Obesity: A Guideline Based on Risk of Gallstone Formation" Am. J. Med. Feb;98(2):115-117 (1995).

Winter et al., "Endothelial anb3 Integrin-Targeted Fumagillin Nanoparticles Inhibit Angiogenesis in Atherosclerosis," Arterioscler Thromb Vasc. Biol., Sep;26(9):2103-2109 (2006).

Written Opinion for International Application No. PCT/US2009/066816, dated Apr. 8, 2010, 3 pages.

Written Opinion for International Application No. PCT/US2011/060127, dated May 10, 2013, 4 pages.

Written Opinion for International Application No. PCT/US2011/062320, dated May 29, 2013, 5 pages.

Yanai et al., "Antitumor Activity of a Medium-chain Triglyceride Solution of the Angiogenesis Inhibitor TNP-470 (AGM-1470) when Administered via the Hepatic Artery to Rats Bearing Walker 256 Carcinosarcoma in the Liver," J. Pharmacol. Exp. Ther. Dec;271(3):1267-1273 (1994).

Yanai et al., "Antitumor Effect of Arterial Administration of a Medium-Chain Triglyceride Solutionof an Angiogenesis Inhibitor, TNP-470, in Rabbits Bearing VX-2 Carcinoma," Pharm Res., May;12(5):653-657 (1995).

Zhang et al., "Angiogenesis Inhibitors Specific for Methionine Aminopeptidase 2 as Drugs for Malaria and Leishmaniasis," J. Biomed. Sci., 9(1):34-40 (Jan.-Feb. 2002).

Arico-Muendel et al., "Carbamate Analogs of Fumagillin as Potent, Targeted Inhibitors of Methionine Aminopeptidase-2," J. Med. Chem., 52:8047-8056 (2009).

International Search Report and Written Opinion for International Application No. PCT/US2016/046511, dated Oct. 21, 2016, 12 pages.

International Search Report and Written Opinion for International Application No. PCT/US2016/046515, dated Jun. 10, 2016, 9 pages.

U.S. Appl. No. 15/399,071, "Fumagillol Compounds and Methods of Making and Using Same," filed Jan. 5, 2017.

U.S. Appl. No. 15/596,512, "Fumagillol Heterocyclic Compounds and Methods of Making and Using Same," filed May 16, 2017.

FUMAGILLOL SPIROCYCLIC COMPOUNDS AND FUSED BICYCLIC COMPOUNDS AND METHODS OF MAKING AND USING SAME

CROSS REFERENCE TO RELATED APPLICATIONS

This application is a continuation of International Patent Application Number PCT/US2016/046515, filed Aug. 11, 2016, which claims the benefit of, and priority to, Chinese Patent Application Number 201510490559.1, filed Aug. 11, 2015, and U.S. Provisional Patent Application No. 62/210,102, filed Aug. 26, 2015, the contents of each of which are hereby incorporated by reference in their entirety.

BACKGROUND

Over 1.1 billion people worldwide are reported to be overweight. Obesity is estimated to affect over 90 million people in the United States alone. Twenty-five percent of the population in the United States over the age of twenty is considered clinically obese. While being overweight or obese presents problems (for example restriction of mobility, discomfort in tight spaces such as theater or airplane seats, social difficulties, etc.), these conditions, in particular clinical obesity, affect other aspects of health, i.e., diseases and other adverse health conditions associated with, exacerbated by, or precipitated by being overweight or obese. The estimated mortality from obesity-related conditions in the United States is over 300,000 annually (O'Brien et al. Amer J Surgery (2002) 184:4S-8S; and Hill et al. (1998) Science, 280:1371).

There is no curative treatment for being overweight or obese. Traditional pharmacotherapies for treating an overweight or obese subject, such as serotonin and noradrenergic re-uptake inhibitors, noradrenergic re-uptake inhibitors, selective serotonin re-uptake inhibitors, intestinal lipase inhibitors, or surgeries such as stomach stapling or gastric banding, have been shown to provide minimal short-term benefits or significant rates of relapse, and have further shown harmful side-effects to patients.

MetAP2 encodes a protein that functions at least in part by enzymatically removing the amino terminal methionine residue from certain newly translated proteins such as glyceraldehyde-3-phosphate dehydrogenase (Warder et al. (2008) J. Proteome Res. 7:4807). Increased expression of the MetAP2 gene has been historically associated with various forms of cancer. Molecules inhibiting the enzymatic activity of MetAP2 have been identified and have been explored for their utility in the treatment of various tumor types (Wang et al. (2003) Cancer Res. 63:7861) and infectious diseases such as microsporidiosis, leishmaniasis, and malaria (Zhang et al. (2002) J. Biomed. Sci. 9:34). Notably, inhibition of MetAP2 activity in obese and obese-diabetic animals leads to a reduction in body weight in part by increasing the oxidation of fat and in part by reducing the consumption of food (Rupnick et al. (2002) Proc. Natl. Acad. Sci. USA 99:10730).

Such MetAP2 inhibitors may be useful as well for patients with excess adiposity and conditions related to adiposity including type 2 diabetes, hepatic steatosis, and cardiovascular disease (via e.g. ameliorating insulin resistance, reducing hepatic lipid content, and reducing cardiac workload). Accordingly, compounds capable of modulating MetAP2 are needed to address the treatment of obesity and related diseases as well as other ailments favorably responsive to MetAP2 modulator treatment.

SUMMARY

The present disclosure provides, for example, compounds which may be modulators of MetAP2, and their use as medicinal agents, processes for their preparation, and pharmaceutical compositions containing them as an active ingredient both alone or in combination with other agents, as well as provides for their use as medicaments and/or in the manufacture of medicaments for the inhibition of MetAP2 activity in warm-blooded animals such as humans. In particular this disclosure relates to compounds useful for the treatment of obesity, type 2 diabetes, and other obesity-associated conditions. Also provided are pharmaceutical compositions comprising at least one disclosed compound and a pharmaceutically acceptable carrier.

For example, provided herein are compounds represented by Formula I or Formula Ia and pharmaceutically acceptable salts, stereoisomers, esters, and prodrugs thereof:

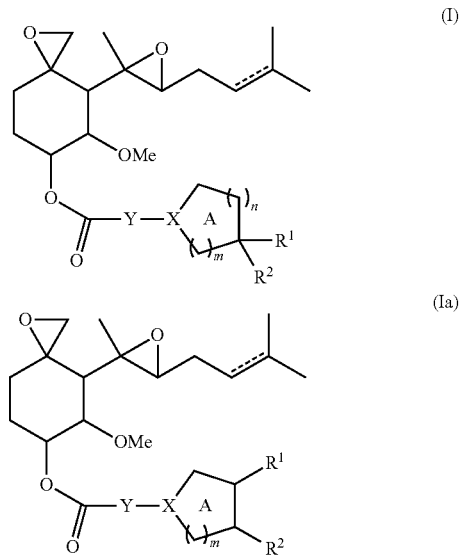

wherein:

⫽ is a single or double bond; and A, X, Y, m, n, $R^1$, and $R^2$ are described below.

Also provided herein is a pharmaceutically acceptable composition comprising a disclosed compound (e.g., of Formula I or Ia) and a pharmaceutically acceptable excipient.

Methods of treating and/or controlling obesity are contemplated herein, comprising administering to a patient in need thereof an effective amount of a disclosed compound (e.g., of Formula I or Ia). In an embodiment, a method of inducing weight loss in a patient in need thereof is provided, comprising administering to said patient an effective amount of a disclosed compound (e.g., of Formula I or Ia). In another embodiment, a method of substantially preventing weight gain in a patient in need thereof is provided comprising administering to said patient an effective amount of a disclosed compound (e.g., of Formula I or Ia).

DETAILED DESCRIPTION

The features and other details of the disclosure will now be more particularly described. Before further description of the present disclosure, certain terms employed in the specification, examples and appended claims are collected here. These definitions should be read in light of the remainder of the disclosure and as understood by a person of skill in the art. Unless defined otherwise, all technical and scientific terms used herein have the same meaning as commonly understood by a person of ordinary skill in the art.

Definitions

"Treating" includes any effect, e.g., lessening, reducing, modulating, or eliminating, that results in the improvement of the condition, disease, disorder and the like.

The term "alkenyl" as used herein refers to an unsaturated straight or branched hydrocarbon having at least one carbon-carbon double bond. Exemplary alkenyl groups include, but are not limited to, a straight or branched group of 2-6 or 3-4 carbon atoms, referred to herein as $C_{2-6}$alkenyl, and $C_{3-4}$alkenyl, respectively. Exemplary alkenyl groups include, but are not limited to, vinyl, allyl, butenyl, pentenyl, etc.

The term "alkoxy" as used herein refers to a straight or branched alkyl group attached to oxygen (alkyl-O—). Exemplary alkoxy groups include, but are not limited to, alkoxy groups of 1-6 or 2-6 carbon atoms, referred to herein as $C_{1-6}$alkoxy, and $C_{2-6}$alkoxy, respectively. Exemplary alkoxy groups include, but are not limited to methoxy, ethoxy, isopropoxy, etc.

The term "alkoxyalkyl" as used herein refers to a straight or branched alkyl group attached to oxygen, attached to a second straight or branched alkyl group (alkyl-O-alkyl-). Exemplary alkoxyalkyl groups include, but are not limited to, alkoxyalkyl groups in which each of the alkyl groups independently contains 1-6 carbon atoms, referred to herein as $C_{1-6}$alkoxy-$C_{1-6}$alkyl. Exemplary alkoxyalkyl groups include, but are not limited to methoxymethyl, 2-methoxyethyl, 1-methoxyethyl, 2-methoxypropyl, ethoxymethyl, 2-isopropoxyethyl etc.

The term "alkyoxycarbonyl" as used herein refers to a straight or branched alkyl group attached to oxygen, attached to a carbonyl group (alkyl-O—C(O)—). Exemplary alkoxycarbonyl groups include, but are not limited to, alkoxycarbonyl groups of 1-6 carbon atoms, referred to herein as $C_{1-6}$alkoxycarbonyl. Exemplary alkoxycarbonyl groups include, but are not limited to, methoxycarbonyl, ethoxycarbonyl, t-butoxycarbonyl, etc.

The term "alkenyloxy" used herein refers to a straight or branched alkenyl group attached to oxygen (alkenyl-O—). Exemplary alkenyloxy groups include, but are not limited to, groups with an alkenyl group of 3-6 carbon atoms, referred to herein as $C_{3-6}$alkenyloxy. Exemplary "alkenyloxy" groups include, but are not limited to allyloxy, butenyloxy, etc.

The term "alkynyloxy" used herein refers to a straight or branched alkynyl group attached to oxygen (alkynyl-O). Exemplary alkynyloxy groups include, but are not limited to, groups with an alkynyl group of 3-6 carbon atoms, referred to herein as $C_{3-6}$alkynyloxy. Exemplary alkynyloxy groups include, but are not limited to, propynyloxy, butynyloxy, etc.

The term "alkyl" as used herein refers to a saturated straight or branched hydrocarbon. Exemplary alkyl groups include, but are not limited to, straight or branched hydrocarbons of 1-6, 1-4, or 1-3 carbon atoms, referred to herein as $C_{1-6}$alkyl, $C_{1-4}$alkyl, and $C_{1-3}$alkyl, respectively. Exemplary alkyl groups include, but are not limited to, methyl, ethyl, propyl, isopropyl, 2-methyl-1-butyl, 3-methyl-2-butyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, etc.

The term "alkylcarbonyl" as used herein refers to a straight or branched alkyl group attached to a carbonyl group (alkyl-C(O)—). Exemplary alkylcarbonyl groups include, but are not limited to, alkylcarbonyl groups of 1-6 atoms, referred to herein as $C_{1-6}$alkylcarbonyl groups. Exemplary alkylcarbonyl groups include, but are not limited to, acetyl, propanoyl, isopropanoyl, butanoyl, etc.

The term "alkynyl" as used herein refers to an unsaturated straight or branched hydrocarbon having at least one carbon-carbon triple bond. Exemplary alkynyl groups include, but are not limited to, straight or branched groups of 2-6, or 3-6 carbon atoms, referred to herein as $C_{2-6}$alkynyl, and $C_{3-6}$alkynyl, respectively. Exemplary alkynyl groups include, but are not limited to, ethynyl, propynyl, butynyl, pentynyl, hexynyl, methylpropynyl, etc.

The term "carbonyl" as used herein refers to the radical —C(O)—.

The term "cyano" as used herein refers to the radical —CN.

The term "cycloalkoxy" as used herein refers to a cycloalkyl group attached to oxygen (cycloalkyl-O—). Exemplary cycloalkoxy groups include, but are not limited to, cycloalkoxy groups of 3-6 carbon atoms, referred to herein as $C_{3-6}$cycloalkoxy groups. Exemplary cycloalkoxy groups include, but are not limited to, cyclopropoxy, cyclobutoxy, cyclohexyloxy, etc The terms "cycloalkyl" or a "carbocyclic group" as used herein refers to a saturated or partially unsaturated hydrocarbon group of, for example, 3-6, or 4-6 carbons, referred to herein as $C_{3-6}$cycloalkyl or $C_{4-6}$cycloalkyl, respectively. Exemplary cycloalkyl groups include, but are not limited to, cyclohexyl, cyclopentyl, cyclopentenyl, cyclobutyl or cyclopropyl.

The terms "halo" or "halogen" as used herein refer to F, Cl, Br, or I.

The terms "heteroaryl" or "heteroaromatic group" as used herein refers to a monocyclic aromatic 5-6 membered ring system containing one or more heteroatoms, for example one to three heteroatoms, such as nitrogen, oxygen, and sulfur. Where possible, said heteroaryl ring may be linked to the adjacent radical though carbon or nitrogen. Examples of heteroaryl rings include but are not limited to furan, thiophene, pyrrole, thiazole, oxazole, isothiazole, isoxazole, imidazole, pyrazole, triazole, pyridine or pyrimidine etc.

The terms "heterocyclyl" or "heterocyclic group" are art-recognized and refer to e.g. saturated or partially unsaturated, 4-10 membered ring structures, or e.g. 4-6 membered saturated ring structures, including bridged or fused rings, and whose ring structures include one to three heteroatoms, such as nitrogen, oxygen, and sulfur. Where possible, heterocyclyl rings may be linked to the adjacent radical through carbon or nitrogen. Examples of heterocyclyl groups include, but are not limited to, pyrrolidine, piperidine, morpholine, thiomorpholine, piperazine, oxetane, azetidine, tetrahydrofuran or dihydrofuran etc.

The term "heterocyclyloxy" as used herein refers to a heterocyclyl group attached to oxygen (heterocyclyl-O—).

The term "heteroaryloxy" as used herein refers to a heteroaryl group attached to oxygen (heteroaryl-O—).

The terms "hydroxy" and "hydroxyl" as used herein refers to the radical —OH.

The term "oxo" as used herein refers to the radical =O.

"Pharmaceutically or pharmacologically acceptable" include molecular entities and compositions that do not produce an adverse, allergic or other untoward reaction when administered to an animal, or a human, as appropriate.

For human administration, preparations should meet sterility, pyrogenicity, and general safety and purity standards as required by FDA Office of Biologics standards.

The term "pharmaceutically acceptable carrier" or "pharmaceutically acceptable excipient" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

The term "pharmaceutical composition" as used herein refers to a composition comprising at least one compound as disclosed herein formulated together with one or more pharmaceutically acceptable carriers.

"Individual," "patient," or "subject" are used interchangeably and include any animal, including mammals, preferably mice, rats, other rodents, rabbits, dogs, cats, swine, cattle, sheep, horses, or primates, and most preferably humans. The compounds of the present disclosure can be administered to a mammal, such as a human, but can also be administered to other mammals such as an animal in need of veterinary treatment, e.g., domestic animals (e.g., dogs, cats, and the like), farm animals (e.g., cows, sheep, pigs, horses, and the like) and laboratory animals (e.g., rats, mice, guinea pigs, and the like). The mammal treated in the methods of the present disclosure is desirably a mammal in which treatment of obesity or weight loss is desired. "Modulation" includes antagonism (e.g., inhibition), agonism, partial antagonism and/or partial agonism.

In the present specification, the term "therapeutically effective amount" means the amount of the subject compound that will elicit the biological or medical response of a tissue, system or animal, (e.g. mammal or human) that is being sought by the researcher, veterinarian, medical doctor or other clinician. The compounds of the present disclosure are administered in therapeutically effective amounts to treat a disease. Alternatively, a therapeutically effective amount of a compound is the quantity required to achieve a desired therapeutic and/or prophylactic effect, such as an amount which results in weight loss.

The term "pharmaceutically acceptable salt(s)" as used herein refers to salts of acidic or basic groups that may be present in compounds used in the compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including, but not limited to, malate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that are acidic in nature are capable of forming base salts with various pharmacologically acceptable cations. Examples of such salts include alkali metal or alkaline earth metal salts, particularly calcium, magnesium, sodium, lithium, zinc, potassium, and iron salts. Compounds included in the present compositions that include a basic or acidic moiety may also form pharmaceutically acceptable salts with various amino acids. The compounds of the disclosure may contain both acidic and basic groups; for example, one amino and one carboxylic acid group. In such a case, the compound can exist as an acid addition salt, a zwitterion, or a base salt.

The compounds of the disclosure may contain one or more chiral centers and, therefore, exist as stereoisomers. The term "stereoisomers" when used herein consist of all enantiomers or diastereomers. These compounds may be designated by the symbols "(+)," "(−)," "R" or "S," depending on the configuration of substituents around the stereogenic carbon atom, but the skilled artisan will recognize that a structure may denote a chiral center implicitly. The present disclosure encompasses various stereoisomers of these compounds and mixtures thereof. Mixtures of enantiomers or diastereomers may be designated "(±)" in nomenclature, but the skilled artisan will recognize that a structure may denote a chiral center implicitly.

The compounds of the disclosure may contain one or more double bonds and, therefore, exist as geometric isomers resulting from the arrangement of substituents around a carbon-carbon double bond. The symbol ⚊ denotes a bond that may be a single, double or triple bond as described herein. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers. Substituents around a carbon-carbon double bond alternatively can be referred to as "cis" or "trans," where "cis" represents substituents on the same side of the double bond and "trans" represents substituents on opposite sides of the double bond.

Compounds of the disclosure may contain a carbocyclic or heterocyclic ring and therefore, exist as geometric isomers resulting from the arrangement of substituents around the ring. The arrangement of substituents around a carbocyclic or heterocyclic ring are designated as being in the "Z" or "E" configuration wherein the terms "Z" and "E" are used in accordance with IUPAC standards. Unless otherwise specified, structures depicting carbocyclic or heterocyclic rings encompass both "Z" and "E" isomers. Substituents around a carbocyclic or heterocyclic rings may also be referred to as "cis" or "trans", where the term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

Individual enantiomers and diasteriomers of compounds of the present disclosure can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, (3) direct separation of the mixture of optical enantiomers on chiral liquid chromatographic columns or (4) kinetic resolution using stereoselective chemical or enzymatic reagents. Racemic mixtures can also be resolved into their component enantiomers by well known methods, such as chiral-phase liquid chromatography or crystallizing the compound in a chiral solvent. Stereoselective syntheses, a chemical or enzymatic reaction in which a single reactant forms an unequal mixture of stereoisomers during the creation of a new stereocenter or during the transformation of a pre-existing one, are well known in the art. Stereoselective syntheses encompass both enantio- and diastereoselective transformations, and may involve the use of chiral auxiliaries. For examples, see Carreira and Kvaerno, *Classics in Stereoselective Synthesis*, Wiley-VCH: Weinheim, 2009.

The compounds disclosed herein can exist in solvated as well as unsolvated forms with pharmaceutically acceptable solvents such as water, ethanol, and the like, and it is intended that the present disclosure embrace both solvated and unsolvated forms. In one embodiment, the compound is amorphous. In one embodiment, the compound is a single polymorph. In another embodiment, the compound is a mixture of polymorphs. In another embodiment, the compound is in a crystalline form.

The present disclosure also embraces isotopically labeled compounds of the disclosure which are identical to those recited herein, except that one or more atoms are replaced by an atom having an atomic mass or mass number different from the atomic mass or mass number usually found in nature. Examples of isotopes that can be incorporated into compounds of the present disclosure include isotopes of hydrogen, carbon, nitrogen, oxygen, phosphorus, sulfur, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. For example, a compound of the disclosure may have one or more H atom replaced with deuterium.

Certain isotopically-labeled disclosed compounds (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labeled compounds of the present disclosure can generally be prepared by following procedures analogous to those disclosed in the examples herein by substituting an isotopically labeled reagent for a non-isotopically labeled reagent.

The term "prodrug" refers to compounds that are transformed in vivo to yield a disclosed compound or a pharmaceutically acceptable salt, hydrate or solvate of the compound. The transformation may occur by various mechanisms (such as by esterase, amidase, phosphatase, oxidative and or reductive metabolism) in various locations (such as in the intestinal lumen or upon transit of the intestine, blood or liver). Prodrugs are well known in the art (for example, see Rautio, Kumpulainen, et al, Nature Reviews Drug Discovery 2008, 7, 255). For example, if a compound of the present disclosure or a pharmaceutically acceptable salt, hydrate or solvate of the compound contains a carboxylic acid functional group, a prodrug can comprise an ester formed by the replacement of the hydrogen atom of the acid group with a group such as $(C_{1-8})$alkyl, $(C_{2-12})$ alkylcarbonyloxymethyl, 1-(alkylcarbonyloxy)ethyl having from 4 to 9 carbon atoms, 1-methyl-1-(alkylcarbonyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_{1-2})$alkylamino$(C_{2-3})$ alkyl (such as 0-dimethylaminoethyl), carbamoyl-$(C_{1-2})$ alkyl, N,N-di$(C_{1-2})$alkylcarbamoyl-$(C_{1-2})$alkyl and piperidino-, pyrrolidino- or morpholino$(C_{2-3})$alkyl.

Similarly, if a disclosed compound contains an alcohol functional group, a prodrug can be formed by the replacement of the hydrogen atom of the alcohol group with a group such as $(C_{1-6})$alkylcarbonyloxymethyl, 1-$((C_{1-6})$alkylcarbonyloxy)ethyl, 1-methyl-1-$((C_{1-6})$alkylcarbonyloxy)ethyl $(C_{1-6})$alkoxycarbonyloxymethyl, N—$(C_{1-6})$alkoxycarbonylaminomethyl, succinoyl, $(C_{1-6})$alkylcarbonyl, α-amino $(C_{1-4})$alkylcarbonyl, arylalkylcarbonyl and α-aminoalkylcarbonyl, or α-aminoalkylcarbonyl-α-aminoalkylcarbonyl, where each α-aminoalkylcarbonyl group is independently selected from the naturally occurring L-amino acids, P(O) $(OH)_2$, —$P(O)(O(C_{1-6})$alkyl$)_2$ or glycosyl (the radical resulting from the removal of a hydroxyl group of the hemiacetal form of a carbohydrate).

If a compound of the present disclosure incorporates an amine functional group, a prodrug can be formed, for example, by creation of an amide or carbamate, an N-alkylcarbonyloxyalkyl derivative, an (oxodioxolenyl)methyl derivative, an N-Mannich base, imine or enamine. In addition, a secondary amine can be metabolically cleaved to generate a bioactive primary amine, or a tertiary amine can metabolically cleaved to generate a bioactive primary or secondary amine. For examples, see Simplicio, et al., *Molecules* 2008, 13, 519 and references therein.

I. Fumagillol Compounds

In one aspect, the present disclosure provides compounds of Formula I or Ia:

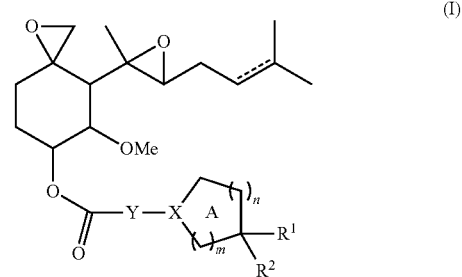

(I)

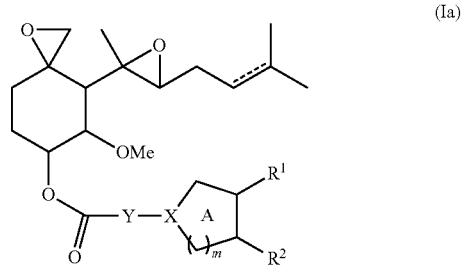

(Ia)

wherein:

⫽ is a single or double bond;

Y is a bond or $NR^a$;

X is N or $CR^N$; wherein X is N when Y is a bond and X is $CR^N$ when Y is $NR^a$;

n is 0 or 1;

m is 1 or 2;

Ring A may be optionally substituted by one or two substituents each independently selected from the group consisting of halogen, hydroxyl, $C_{1-3}$alkyl and $C_{1-3}$alkoxy, wherein $C_{1-3}$alkyl and $C_{1-3}$alkoxy may optionally be substituted by one or more fluorine atoms or a substituent selected from the group consisting of cyano, hydroxyl, and N(R$^a$R$^b$);

R$^1$ and R$^2$, together with the carbon or carbons to which they are attached, form a 4-6 membered saturated heterocyclic ring B having one or two heteroatoms selected from the group consisting of O, S(O)$_w$ (wherein w is 0, 1 or 2) and NR$^h$ or form a 3-6 membered saturated carbocyclic ring B; wherein the heterocyclic or carbocyclic ring B may optionally be substituted on a free carbon by one or two substituents each independently selected from the group consisting of halogen, hydroxyl, oxo, C$_{1-3}$alkyl, C$_{1-3}$alkoxy, —C(O)—NR$^i$R$^j$, —C(O)—N(R$^a$)—C$_{1-6}$alkylene-NR$^i$R$^j$, —C$_{1-6}$alkylene-NR$^i$R$^j$, —C$_{1-6}$alkylene-O—C(O)—NR$^i$R$^j$, and —O—C(O)—NR$^i$R$^j$; wherein C$_{1-3}$alkyl, C$_{1-3}$alkoxy, —C(O)—NR$^i$R$^j$, —C(O)—N(R$^a$)—C$_{1-6}$alkylene-NR$^i$R$^j$, —C$_{1-6}$alkylene-NR$^i$R$^j$, —C$_{1-6}$alkylene-O—C(O)—NR$^i$R$^j$ and —O—C(O)—NR$^i$R$^j$ may optionally be substituted by one or more fluorine atoms or a group selected from cyano, hydroxyl, or N(R$^a$R$^b$);

R$^i$ and R$^j$ are selected independently for each occurrence from the group consisting of hydrogen, C$_{1-6}$alkyl, C$_{2-6}$alkenyl, C$_{3-6}$cycloalkyl, heterocyclyl and heterocyclylcarbonyl; wherein C$_{1-6}$alkyl, C$_{2-6}$alkenyl and C$_{3-6}$cycloalkyl may be optionally substituted by one or more substituents independently selected from the group consisting of fluorine, hydroxyl, cyano, R$^a$R$^b$N—, R$^a$R$^b$N-carbonyl- and C$_{1-3}$alkoxy; and wherein heterocyclyl and heterocyclylcarbonyl may be optionally substituted by one or more substituents independently selected from the group consisting of C$_{1-6}$alkyl, C$_{2-6}$alkenyl, C$_{2-6}$alkynyl, C$_{3-6}$cycloalkyl, C$_{1-6}$alkoxy, halo-C$_{1-6}$-alkyl, hydroxyl-C$_{1-6}$-alkyl, R$^a$R$^b$N—C$_{1-6}$alkyl- and C$_{1-6}$-alkoxy-C$_{1-6}$-alkyl; and wherein if said heterocyclyl or heterocyclylcarbonyl contains a —NH moiety that nitrogen may optionally be substituted by one or more groups independently selected from the group consisting of C$_{1-6}$alkyl, C$_{3-6}$alkenyl, C$_{3-6}$alkynyl, C$_{3-6}$cycloalkyl, C$_{1-6}$alkyl-S(O)$_2$— and C$_{1-6}$-alkylcarbonyl;

or R$^i$ and R$^j$ taken together with the nitrogen to which they are attached form a 4-9 membered heterocyclic ring, which may have an additional heteroatom selected from the group consisting of N, O, and S(O)$_w$ (wherein w is 0, 1 or 2); wherein the heterocyclic ring may be optionally substituted on carbon by one, two, or more substituents selected from the group consisting of halogen, hydroxyl, oxo, cyano, C$_{1-6}$alkyl, C$_{1-6}$alkoxy, R$^a$R$^b$N—, R$^a$R$^b$N—SO$_2$— and R$^a$R$^b$N-carbonyl-; wherein said C$_{1-6}$alkyl and C$_{1-6}$alkoxy may optionally be substituted the group consisting of fluorine, hydroxyl, and cyano; and wherein if said heterocyclic ring contains a —NH moiety that nitrogen may optionally be substituted by a substituent selected from the group consisting of hydrogen, C$_{1-6}$alkyl, C$_{3-6}$alkenyl, C$_{3-6}$alkynyl, C$_{3-6}$cycloalkyl, C$_{1-6}$alkyl-S(O)$_2$—, C$_{1-6}$alkylcarbonyl-, C$_{1-6}$alkoxycarbonyl-, R$^i$R$^j$N-carbonyl- and R$^i$R$^j$N—SO$_2$—; wherein C$_{1-6}$alkyl, C$_{3-6}$alkenyl, C$_{3-6}$alkynyl, C$_{3-6}$cycloalkyl, C$_{1-6}$alkyl-S(O)$_2$—, C$_{1-6}$alkylcarbonyl-, and C$_{1-6}$alkoxycarbonyl- may optionally be substituted by one or more substituents selected from the group consisting of fluorine, hydroxyl, and cyano;

R$^h$ is independently selected for each occurrence from the group consisting of hydrogen, C$_{1-6}$alkyl, C$_{3-6}$alkenyl, C$_{3-6}$alkynyl, C$_{3-6}$cycloalkyl, C$_{1-6}$alkyl-S(O)$_2$—, C$_{1-6}$alkylcarbonyl-, C$_{1-6}$alkoxycarbonyl-, R$^i$R$^j$N-carbonyl- and R$^i$R$^j$N—SO$_2$—; wherein C$_{1-6}$alkyl, C$_{3-6}$alkenyl, C$_{3-6}$alkynyl, C$_{3-6}$cycloalkyl, C$_{1-6}$alkyl-S(O)$_2$—, C$_{1-6}$alkylcarbonyl-, and C$_{1-6}$alkoxycarbonyl- may optionally be substituted by one or more substituents selected from R$^P$;

R$^P$ is independently selected, for each occurrence, from the group consisting of halogen, hydroxyl, cyano, C$_{1-6}$alkoxy, R$^i$R$^j$N—, R$^i$R$^j$N-carbonyl-, R$^i$R$^j$N—SO$_2$—, and R$^i$R$^j$N-carbonyl-N(R$^a$)—;

R$^N$ is selected from the group consisting of hydrogen, halogen, hydroxyl, and C$_{1-6}$alkyl; and R$^a$ and R$^b$ are independently selected, for each occurrence, from the group consisting of hydrogen and C$_{1-4}$alkyl; wherein C$_{1-4}$alkyl may optionally be substituted by one or more substituents selected from the group consisting of halogen, cyano, oxo, and hydroxyl;

and pharmaceutically acceptable salts, stereoisomers, esters, and prodrugs thereof.

In certain embodiments, X may be N and Y may be a bond.

In certain other embodiments, X may be CR$^N$ and Y may be NR$^a$. For example, X may be CH and Y may be NH.

In certain embodiments, R$^1$ and R$^2$, together with the carbon or carbons to which they are attached, may form a 4, 5, or 6-membered saturated heterocyclic ring B having one oxygen.

In another embodiment, R$^1$ and R$^2$, together with the carbon or carbons to which they are attached, may form a 4, 5, or 6-membered saturated heterocyclic ring B having one NR$^g$.

In a further embodiment, R$^1$ and R$^2$, together with the carbon or carbons to which they are attached, may form a 4, 5, or 6-membered saturated heterocyclic ring B having one S(O)$_2$.

In a further embodiment, R$^1$ and R$^2$, together with the carbon or carbons to which they are attached, may form a 4, 5, or 6-membered saturated carbocyclic ring B.

In certain embodiments, a disclosed compound may represented by Formula I.

In an embodiment, n may be 0 and m may be 1. In another embodiment, n may be 1 and m may be 1. In a further embodiment, n may be 1 and m may be 2.

In certain embodiments, a disclosed compound may represented by Formula Ia. For example, m may be 1.

In certain embodiments, a disclosed compound may be represented by:

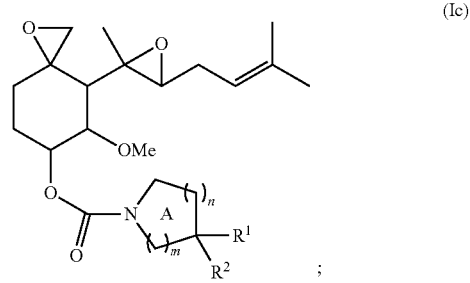

(Ic)

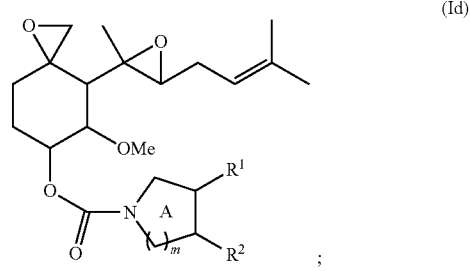

(Id)

In certain embodiments, A and B may be selected from the group consisting of:

wherein $X^{11}$ is selected from the group consisting of $C(R^{11}R^{22})$, $NR^h$, O, and $S(O)_2$; and $R^{11}$ and $R^{22}$ are independently selected from the group consisting of hydrogen, halogen, —C(O)—$NR^iR^j$, —C(O)—N($R^a$)—$C_{1-6}$alkylene-$NR^iR^j$, —$C_{1-6}$alkylene-$NR^iR^j$, —$C_{1-6}$alkylene-O—C(O)—$NR^iR^j$, and —O—C(O)—$NR^iR^j$.

For example, A and B may be selected from the group consisting of:

-continued

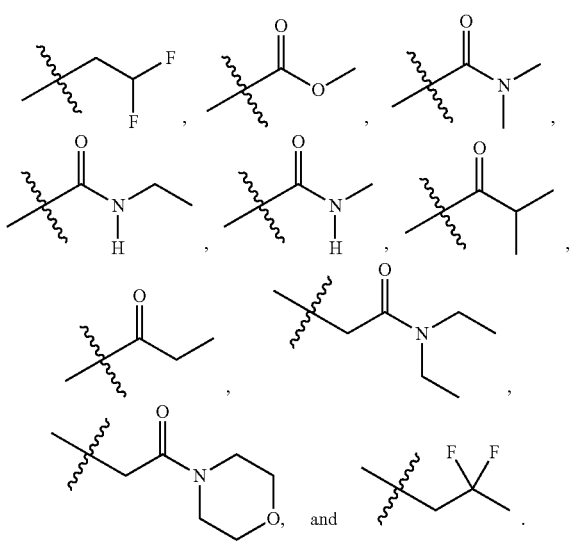

In certain embodiments, $R^h$ may be selected from the group consisting of hydrogen, $C_{1-3}$alkyl optionally substituted by one or more fluorine atoms, —C(O)—O—$C_{1-3}$alkyl, —C(O)—NR$^i$R$^j$, —C(O)—$C_{1-3}$alkyl, and —$C_{1-3}$alkylene-C(O)—NR$^i$R$^j$. For example, R$^i$ and R$^j$ may be independently selected from the group consisting of hydrogen and $C_{1-3}$alkyl; or R$^i$ and R$^j$ taken together with the nitrogen to which they are attached may form a 4-6 membered heterocyclic ring, which may have an additional heteroatom selected from the group consisting of NH, O, and S(O)$_w$ (wherein w is 0, 1 or 2).

For example, $R^h$ may be selected from the group consisting of hydrogen, methyl, In certain embodiments, $R^{11}$ and $R^{22}$ may be hydrogen. In certain other embodiments, $R^{11}$ and $R^{22}$ may be fluorine atoms.

In certain embodiments, one of $R^1$ or $R^{22}$ may be hydrogen and the other may be selected from the group consisting of —C(O)—NR$^i$R$^j$, —C(O)—NH—CH$_2$—CH$_2$—NR$^i$R$^j$, —C(O)—NMe-CH$_2$—CH$_2$—NR$^i$R$^j$, —CH$_2$—NR$^i$R$^j$, —CH$_2$—O—C(O)—NR$^i$R$^j$, and —O—C(O)—NR$^i$R$^j$. For example, R$^i$ and R$^j$ may be independently selected from the group consisting of hydrogen and $C_{1-3}$alkyl, or R$^i$ and R$^j$ taken together with the nitrogen to which they are attached may form a 4-6 membered heterocyclic ring, which may have an additional heteroatom selected from the group consisting of N and O; wherein the heterocyclic ring may be optionally substituted on carbon by one, two, or more fluorine atoms; and wherein if said heterocyclic ring contains a —NH moiety that nitrogen may be optionally substituted by $C_{1-3}$alkyl; wherein $C_{1-3}$alkyl may optionally be substituted by one or more fluorine atoms.

For example, one of $R^{11}$ or $R^{22}$ may be hydrogen and the other may be selected from the group consisting of:

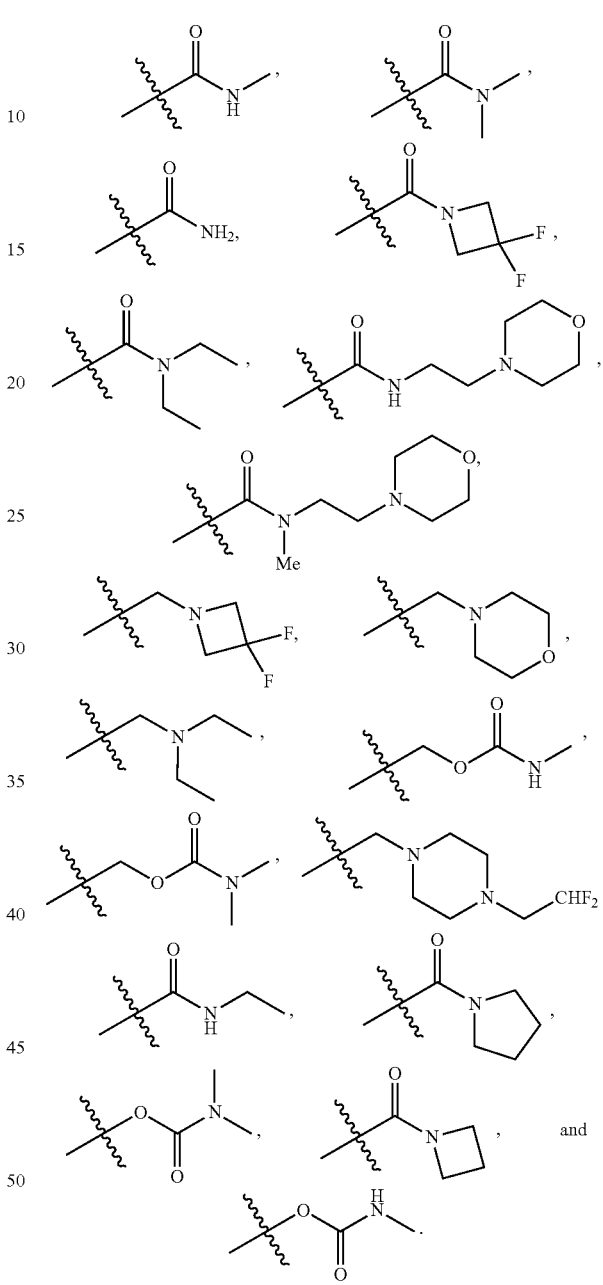

Also provided herein are compounds that may be selected from the group consisting of: (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-oxa-9-azaspiro[5.5]undecane-9-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 2-oxa-6-azaspiro[3.3]heptane-6-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 7-oxa-2-azaspiro[3.5]nonane-2-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 2-oxa-6-azaspiro[3.4]octane-6-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 2-oxa-7-azaspiro[3.5]nonane-7-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 6-oxa-2-azaspiro[3.4]octane-2-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl (7-methyl-7-azaspiro[3.5]nonan-2-yl)carbamate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 7-methyl-2,7-diazaspiro[3.5]nonane-2-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 7-(2,2-difluoroethyl)-2,7-diazaspiro[3.5]nonane-2-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl (2-methyl-2-azaspiro[3.3]heptan-6-yl)carbamate; (3R,4S,5S,6R)-5-methoxy-4-((2R,3R)-2-methyl-3-(3-methylbut-2-en-1-yl)oxiran-2-yl)-1-oxaspiro[2.5]octan-6-yl (6-methyl-6-azaspiro[3.4]octan-2-yl)carbamate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 6-methyl-2,6-diazaspiro[3.3]heptane-2-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl (3aR,6aS)-tetrahydro-1H-furo[3,4-c]pyrrole-5(3H)-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 9-(2,2-difluoroethyl)-3,9-diazaspiro[5.5]undecane-3-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 2-(2,2-difluoroethyl)-2,6-diazaspiro[3.4]octane-6-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 8-(2,2-difluoroethyl)-2,8-diazaspiro[4.5]decane-2-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 6-(2,2-difluoroethyl)-2,6-diazaspiro[3.4]octane-2-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 6-(2,2-difluoroethyl)-2,6-diazaspiro[3.3]heptane-2-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl (3aR,6aS)-5-(2,2-difluoroethyl)hexahydropyrrolo[3,4-c]pyrrole-2(1H)-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 5-methylhexahydropyrrolo[3,4-c]pyrrole-2(1H)-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-azabicyclo[3.1.0]hexane-3-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 6,6-difluoro-3-azabicyclo[3.1.0]hexane-3-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 2-thia-6-azaspiro[3.3]heptane-6-carboxylate 2,2-dioxide; (3R,4S,5S,6R)-5-methoxy-4-((2R,3R)-2-methyl-3-(3-methylbut-2-en-1-yl)oxiran-2-yl)-1-oxaspiro[2.5]octan-6-yl 2-oxa-8-azaspiro[4.5]decane-8-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 7-oxo-2,6-diazaspiro[3.4]octane-2-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 8-methyl-2,8-diazaspiro[4.5]decane-2-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 8-oxa-2-azaspiro[4.5]decane-2-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 9-methyl-3,9-diazaspiro[5.5]undecane-3-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-oxo-2,8-diazaspiro[4.5]decane-8-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 8-oxo-3,9-diazaspiro[5.5]undecane-3-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 9-methyl-8-oxo-3,9-diazaspiro[5.5]undecane-3-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl (1R,5S,6R)-6-(methylcarbamoyl)-3-azabicyclo[3.1.0]hexane-3-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl (1R,5S,6R)-6-(dimethylcarbamoyl)-3-azabicyclo[3.1.0]hexane-3-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl (1R,5S,6R)-6-carbamoyl-3-azabicyclo[3.1.0]hexane-3-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl (1R,5S,6R)-6-(3,3-difluoroazetidine-1-carbonyl)-3-azabicyclo[3.1.0]hexane-3-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl (1R,5S,6R)-6-(diethylcarbamoyl)-3-azabicyclo[3.1.0]hexane-3-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl (1R,5S,6R)-6-((2-morpholinoethyl)carbamoyl)-3-azabicyclo[3.1.0]hexane-3-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl (1R,5S,6R)-6-(methyl(2-morpholinoethyl)carbamoyl)-3-azabicyclo[3.1.0]hexane-3-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl (1R,5S,6S)-6-((3,3-difluoroazetidin-1-yl)methyl)-3-azabicyclo[3.1.0]hexane-3-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl (1R,5S,6S)-6-(morpholinomethyl)-3-azabicyclo[3.1.0]hexane-3-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl (1R,5S,6S)-6-((diethylamino)methyl)-3-azabicyclo[3.1.0]hexane-3-carboxylate; 2-((3R,4S,5S,6R)-5-methoxy-4-((2R,3R)-2-methyl-3-(3-methylbut-2-en-1-yl)oxiran-2-yl)-1-oxaspiro[2.5]octan-6-yl) 5-methyl (3aR,6aS)-tetrahydropyrrolo[3,4-c]pyrrole-2,5(1H,3H)-dicarboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl (3aR,6aS)-5-(dimethylcarbamoyl)hexahydropyrrolo[3,4-c]pyrrole-2(1H)-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl (3 aR,6aS)-5-(ethylcarbamoyl)hexahydropyrrolo[3,4-c]pyrrole-2(1H)-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl (3aR,6aS)-5-(methylcarbamoyl)hexahydropyrrolo[3,4-c]pyrrole-2(1H)-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl (3aR,6aS)-5-isobutyrylhexahydropyrrolo[3, 4-c]pyrrole-2(1H)-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl (3aR,6aS)-5-propionylhexahydropyrrolo[3,4-c]pyrrole-2(1H)-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl (3aR,6aS)-5-(2-(diethylamino)-2-oxoethyl)hexahydropyrrolo[3,4-c]pyrrole-2(1H)-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl (3aR,6aS)-5-(2-morpholino-2-oxoethyl)hexahydropyrrolo[3,4-c]pyrrole-2(1H)-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl (1R,5S,6R)-6-(((methylcarbamoyl)oxy)methyl)-3-azabicyclo[3.1.0]hexane-3-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl (1R,5S,6R)-6-(((dimethylcarbamoyl)oxy)methyl)-3-azabicyclo[3.1.0]hexane-3-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 6-(morpholinomethyl)-2-azaspiro[3.3]heptane-2-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl (3aR,6aS)-5-(2,2-difluoropropyl)hexahydropyrrolo[3,4-c]pyrrole-2(1H)-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 6-((4-(2,2-difluoroethyl)piperazin-1-yl)methyl)-2-azaspiro[3.3]heptane-2-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl (3aR,6aS)-5-(morpholinomethyl)hexahydrocyclopenta[c]pyrrole-2(1H)-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl (1R,5S,6R)-6-(ethylcarbamoyl)-3-azabicyclo[3.1.0]hexane-3-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl (1R,5S,6R)-6-(pyrrolidine-1-carbonyl)-3-azabicyclo[3.1.0]hexane-3-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl (3aR,5S,6aS)-5-((dimethylcarbamoyl)oxy)hexahydrocyclopenta[c]pyrrole-2(1H)-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl (1R,5S,6R)-6-(azetidine-1-carbonyl)-3-azabicyclo[3.1.0]hexane-3-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl (3aR,6aS)-5-((diethylamino)methyl)hexahydrocyclopenta[c]pyrrole-2(1H)-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl (3aR,6aS)-5 (((methylcarbamoyl)oxy)methyl)hexahydrocyclopenta[c] pyrrole-2(1H)-carboxylate; and a pharmaceutically acceptable salt or stereoisomer thereof.

Procedures for making compounds described herein are provided below in the working examples and may be supplemented or substituted by procedures known to those of skill in the art. In the reactions described below, it may be necessary to protect reactive functional groups (such as hydroxyl, amino, thio or carboxyl groups) to avoid their unwanted participation in the reactions. The incorporation of such groups, and the methods required to introduce and remove them, are known to those skilled in the art (for example, see Greene, Wuts, Protective Groups in Organic Synthesis. 2nd Ed. (1999)). The deprotection step may be the final step in the synthesis such that the removal of protecting groups affords compounds of Formula I or Ia, as disclosed herein. Starting materials used in the working examples can be purchased or prepared by methods described in the chemical literature, or by adaptations thereof, using methods known by those skilled in the art. The order in which the steps are performed can vary depending on the groups introduced and the reagents used, but would be apparent to those skilled in the art.

Compounds of Formula I or Ia, or any of the intermediates described herein, can be further derivatised by using one or more standard synthetic methods known to those skilled in the art. Such methods can involve substitution, oxidation or reduction reactions. These methods can also be used to obtain or modify compounds of Formula I or Ia or any preceding intermediates by modifying, introducing or removing appropriate functional groups. Particular substitution approaches include alkylation, arylation, heteroarylation, acylation, thioacylation, halogenation, sulfonylation, nitration, formylation, hydrolysis and coupling procedures. These procedures can be used to introduce a functional group onto the parent molecule (such as the nitration or sulfonylation of aromatic rings) or to couple two molecules together (for example to couple an amine to a carboxylic acid to afford an amide; or to form a carbon-carbon bond between two heterocycles). For example, alcohol or phenol groups can be converted to ether groups by coupling a phenol with an alcohol in a solvent (such as tetrahydrofuran) in the presence of a phosphine (such as triphenylphosphine) and a dehydrating agent (such as diethyl, diisopropyl or dimethyl azodicarboxylate). Alternatively, ether groups can be prepared by deprotonation of an alcohol, using a suitable base (such as sodium hydride) followed by the addition of an alkylating agent (such as an alkyl halide or an alkyl sulfonate).

In another example, a primary or secondary amine can be alkylated using a reductive alkylation procedure. For example, the amine can be treated with an aldehyde and a borohydride (such as sodium triacetoxyborohydride, or sodium cyanoborohydride in a solvent (such as a halogenated hydrocarbon, for example dichloromethane, or an alcohol, for example ethanol) and, where necessary, in the presence of an acid (such as acetic acid).

In another example, hydroxy groups (including phenolic OH groups) can be converted into leaving groups, such as halogen atoms or sulfonyloxy groups (such as alkylsulfonyloxy, for example trifluoromethanesulfonyloxy, or aryl sulfonyloxy, for example p-toluenesulfonyloxy) using conditions known to those skilled in the art. For example, an aliphatic alcohol can be reacted with thionyl chloride in a halogenated hydrocarbon (such as dichloromethane) to afford the corresponding alkyl chloride. A base (such as triethylamine) can also be used in the reaction.

In another example, ester groups can be converted to the corresponding carboxylic acid by acid- or base-catalysed hydrolysis depending on the nature of the ester group. Acid catalysed hydrolysis can be achieved by treatment with an organic or inorganic acid (such as trifluoroacetic acid in an aqueous solvent, or a mineral acid such as hydrochloric acid in a solvent such as dioxane). Base catalysed hydrolysis can be achieved by treatment with an alkali metal hydroxide (such as lithium hydroxide in an aqueous alcohol, for example methanol).

In another example, aromatic halogen substituents in the compounds may be subjected to halogen-metal exchange by treatment with a base (such as a lithium base, for example n-butyl or t-butyl lithium) optionally at a low temperature (such as −78° C.) in a solvent (such as tetrahydrofuran) and the mixture may then be quenched with an electrophile to introduce a desired substituent. Thus, for example, a formyl group can be introduced by using dimethylformamide as the electrophile. Aromatic halogen substituents can also be subjected to palladium catalysed reactions to introduce groups such as carboxylic acids, esters, cyano or amino substituents.

In another example, an aryl, or heteroaryl ring substituted with an appropriate leaving group (such as a halogen or sulfonyl ester, for example a triflate) can undergo a palladium catalysed coupling reaction with a wide variety of substrates to form a carbon-carbon bond. For example, a Heck reaction can be used to couple such a ring system to an alkene (which may, or may not, be further substituted) by treatment with an organopalladium complex (such as tetrakis(triphenylphosphine)palladium(0), palladium (II) acetate or palladium (II) chloride) in the presence of a ligand (such as a phosphine, for example triphenylphosphine) in the presence of a base (such as potassium carbonate or a tertiary amine, for example, triethylamine), in an appropriate solvent (such as tetrahydrofuran or DMF), under appropriate conditions (such as heating to, for example, 50-120° C.). In another example, a Sonogashira reaction can be used to couple such a ring system to an alkyne (which may, or may not be further substituted) by treatment with a palladium complex (such as tetrakis(triphenylphosphine)palladium(0)) and a halide salt of copper (I) (such as copper (I) iodide), in the presence of a base (such as a potassium carbonate or a tertiary amine, for example, triethylamine), in an appropriate solvent (such as tetrahydrofuran or dimethylformamide), under appropriate conditions (such as heating to, for example, 50-120° C.). In another example, a Stille reaction can be used to couple such a ring system to an alkene, by treatment with an organotin compound (such as an alkynyltin or alkenyltin reagent, for example an alkenyltributylstannane) in the presence of a palladium complex (such as tetrakis(triphenylphosphine)palladium(0)), with, or without the presence of a salt (such as a copper (I) halide), in an appropriate solvent (such as dioxane or dimethylformamide), under appropriate conditions (such as heating to, for example, 50-120° C.).

Particular oxidation approaches include dehydrogenations and aromatisation, decarboxylation and the addition of oxygen to certain functional groups. For example, aldehyde groups can be prepared by oxidation of the corresponding alcohol using conditions well known to those skilled in the art. For example, an alcohol can be treated with an oxidising agent (such as Dess-Martin periodinane) in a solvent (such as a halogenated hydrocarbon, for example dichloromethane). Alternative oxidising conditions can be used, such as treatment with oxalyl chloride and an activating amount of dimethylsulfoxide and subsequent quenching by the addition of an amine (such as triethylamine). Such a reaction can be carried out in an appropriate solvent (such as a halogenated hydrocarbon, for example dichloromethane) and under appropriate conditions (such as cooling below room temperature, for example to −78° C. followed by warming to room temperature). In another example, sulfur atoms can be oxidised to the corresponding sulfoxide or sulfone using an oxidising agent (such as a peroxy acid, for example 3-chloroperoxybenzoic acid) in an inert solvent (such as a halogenated hydrocarbon, for example dichloromethane) at around ambient temperature.

Particular reduction approaches include the removal of oxygen atoms from particular functional groups or saturation (or partial saturation) of unsaturated compounds including aromatic or heteroaromatic rings. For example, primary alcohols can be generated from the corresponding ester or aldehyde by reduction, using a metal hydride (such as lithium aluminium hydride or sodium borohydride in a solvent such as methanol). Alternatively, —CH$_2$OH groups can be generated from the corresponding carboxylic acid by reduction, using a metal hydride (such as lithium aluminium hydride in a solvent such as tetrahydrofuran). In another example, a nitro group may be reduced to an amine by catalytic hydrogenation in the presence of a metal catalyst (such as palladium on a solid support such as carbon) in a solvent (such as an ether, for example tetrahydrofuran, or an alcohol, such as methanol), or by chemical reduction using a metal (such as zinc, tin or iron) in the presence of an acid (such as acetic acid or hydrochloric acid). In a further example an amine can be obtained by reduction of a nitrile, for example by catalytic hydrogenation in the presence of a metal catalyst (such as palladium on a solid support such as carbon), or Raney nickel in a solvent (such as tetrahydrofuran) and under suitable conditions (such as cooling to below room temperature, for example to −78° C., or heating, for example to reflux).

Salts of compounds of Formula I or Ia can be prepared by the reaction of a compound of Formula I or Ia with an appropriate acid or base in a suitable solvent, or mixture of solvents (such as an ether, for example, diethyl ether, or an alcohol, for example ethanol, or an aqueous solvent) using conventional procedures. Salts of compound of Formula I or Ia can be exchanged for other salts by treatment using conventional ion-exchange chromatography procedures.

Where it is desired to obtain a particular enantiomer of a compound of Formula I or Ia, this may be produced from a corresponding mixture of enantiomers by employing any suitable conventional procedure for resolving enantiomers. For example, diastereomeric derivatives (such as salts) can be produced by reaction of a mixture of enantiomers of a compound of Formula I or Ia (such a racemate) and an appropriate chiral compound (such as a chiral base). The diastereomers can then be separated by any conventional means such as crystallisation, and the desired enantiomer recovered (such as by treatment with an acid in the instance where the diastereomer is a salt). Alternatively, a racemic mixture of esters can be resolved by kinetic hydrolysis using a variety of biocatalysts (for example, see Patel Steroselective Biocatalysts, Marcel Decker; New York 2000).

In another resolution process a racemate of compounds of Formula I or Ia can be separated using chiral High Performance Liquid Chromatography. Alternatively, a particular enantiomer can be obtained by using an appropriate chiral intermediate in one of the processes described above. Chromatography, recrystallisation and other conventional separation procedures may also be used with intermediates or final products where it is desired to obtain a particular geometric isomer of the present disclosure.

II. Methods

Another aspect of the present disclosure provides methods of modulating the activity of MetAP2. Such methods comprise exposing said receptor to a compound described herein. In some embodiments, the compound utilized by one or more of the foregoing methods is one of the generic, subgeneric, or specific compounds described herein, such as a compound of Formula I or Ia. The ability of compounds described herein to modulate or inhibit MetAP2 can be evaluated by procedures known in the art and/or described herein. Another aspect of the present disclosure provides methods of treating a disease associated with expression or activity of MetAP2 in a patient.

In certain embodiments, the present disclosure provides a method of treating and/or controlling obesity, comprising administering to a patient in need thereof an effective amount of a disclosed compound.

In certain embodiments, the present disclosure provides a method of inducing weight loss in a patient in need thereof, comprising administering to said patient an effective amount of a disclosed compound.

In certain embodiments, the present disclosure provides a method of substantially preventing weight gain in a patient in need thereof, comprising administering to said patient an effective amount of a disclosed compound.

In certain embodiments, the patient is a human.

In certain embodiments, the patient is a cat or dog.

In certain embodiments, the patient has a body mass index greater than or equal to about 30 kg/m$^2$ before the administration.

In certain embodiments, administering a disclosed compound may comprise subcutaneous administration. In certain embodiments, administering a disclosed compound may comprise intravenous administration.

Provided methods of treatment may include administering a disclosed compound once, twice, or three times daily; about every other day (e.g. every 2 days); twice weekly (e.g. every 3 days, every 4 days, every 5 days, every 6 days, or e.g. administered with an interval of about 2 to about 3 days between doses); once weekly; three times weekly; every other week; twice monthly; once a month; every other month; or even less often.

In certain embodiments, a method disclosed herein further comprises administering said compound in an amount sufficient to establish inhibition of intracellular MetAP2 effective to increase thioredoxin production in the patient and to induce multi organ stimulation of anti-obesity processes in the subject.

In certain embodiments, the method comprises administering said compound in an amount insufficient to reduce angiogenesis in the patient.

Other contemplated methods of treatment include method of treating or ameliorating an obesity-related condition or co-morbidity, by administering a compound disclosed herein to a subject. For example, contemplated herein are methods for treating type 2 diabetes in a patient in need thereof.

Exemplary co-morbidities include cardiac disorders, endocrine disorders, respiratory disorders, hepatic disorders, skeletal disorders, psychiatric disorders, metabolic disorders, and reproductive disorders.

Exemplary cardiac disorders include hypertension, dyslipidemia, ischemic heart disease, cardiomyopathy, cardiac infarction, stroke, venous thromboembolic disease and pulmonary hypertension. Exemplary endocrine disorders include type 2 diabetes and latent autoimmune diabetes in adults. Exemplary respiratory disorders include obesity-hypoventilation syndrome, asthma, and obstructive sleep apnea. An exemplary hepatic disorder is nonalcoholic fatty liver disease. Exemplary skeletal disorders include back pain and osteoarthritis of weight-bearing joints. Exemplary metabolic disorders include Prader-Willi Syndrome and polycystic ovary syndrome. Exemplary reproductive disorders include sexual dysfunction, erectile dysfunction, infertility, obstetric complications, and fetal abnormalities. Exemplary psychiatric disorders include weight-associated depression and anxiety.

In particular, in certain embodiments, the present disclosure provides a method of treating one of more of the above medical indications comprising administering to a subject in need thereof a therapeutically effective amount of a compound described herein, such as a compound of Formula I or Ia.

Obesity or reference to "overweight" refers to an excess of fat in proportion to lean body mass. Excess fat accumulation is associated with increase in size (hypertrophy) as well as number (hyperplasia) of adipose tissue cells. Obesity is variously measured in terms of absolute weight, weight: height ratio, distribution of subcutaneous fat, and societal and esthetic norms. A common measure of body fat is Body Mass Index (BMI). The BMI refers to the ratio of body weight (expressed in kilograms) to the square of height (expressed in meters). Body mass index may be accurately calculated using either of the formulas: weight(kg)/height$^2$ (m$^2$) (SI) or 703×weight(lb)/height$^2$(in$^2$) (US).

In accordance with the U.S. Centers for Disease Control and Prevention (CDC), an overweight adult has a BMI of 25 kg/m$^2$ to 29.9 kg/m$^2$, and an obese adult has a BMI of 30 kg/m$^2$ or greater. A BMI of 40 kg/m$^2$ or greater is indicative of morbid obesity or extreme obesity. Obesity can also refer to patients with a waist circumference of about 102 cm for males and about 88 cm for females. For children, the definitions of overweight and obese take into account age and gender effects on body fat. Patients with differing genetic background may be considered "obese" at a level differing from the general guidelines, above.

The compounds of the present disclosure also are useful for reducing the risk of secondary outcomes of obesity, such as reducing the risk of left ventricular hypertrophy. Methods for treating patients at risk of obesity, such as those patients who are overweight, but not obese, e.g. with a BMI of between about 25 and 30 kg/m$^2$, are also contemplated. In certain embodiments, a patient is a human.

BMI does not account for the fact that excess adipose can occur selectively in different parts of the body, and development of adipose tissue can be more dangerous to health in some parts of the body rather than in other parts of the body. For example, "central obesity", typically associated with an "apple-shaped" body, results from excess adiposity especially in the abdominal region, including belly fat and visceral fat, and carries higher risk of co-morbidity than "peripheral obesity", which is typically associated with a "pear-shaped" body resulting from excess adiposity especially on the hips. Measurement of waist/hip circumference ratio (WHR) can be used as an indicator of central obesity. A minimum WHR indicative of central obesity has been variously set, and a centrally obese adult typically has a WHR of about 0.85 or greater if female and about 0.9 or greater if male.

Methods of determining whether a subject is overweight or obese that account for the ratio of excess adipose tissue to lean body mass involve obtaining a body composition of the subject. Body composition can be obtained by measuring the thickness of subcutaneous fat in multiple places on the body, such as the abdominal area, the subscapular region, arms, buttocks and thighs. These measurements are then used to estimate total body fat with a margin of error of approximately four percentage points. Another method is bioelectrical impedance analysis (BIA), which uses the resistance of electrical flow through the body to estimate body fat. Another method is using a large tank of water to measure body buoyancy. Increased body fat will result in greater buoyancy, while greater muscle mass will result in a tendency to sink.

In another aspect, the present disclosure provides methods for treating an overweight or obese subject involving determining a level of at least one biomarker related to being overweight or obese in the subject, and administering an effective amount of a disclosed compound to achieve a target level in the subject. Exemplary biomarkers include body weight, Body Mass Index (BMI), Waist/Hip ratio WHR, plasma adipokines, and a combination of two or more thereof.

In certain embodiments, the compound utilized by one or more of the foregoing methods is one of the generic, subgeneric, or specific compounds described herein, such as a compound of Formula I or Ia.

The compounds of the present disclosure may be administered to patients (animals and humans) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors which those skilled in the art will recognize, with the appropriate dosage ultimately being at the discretion of the attendant physician. For treating clinical conditions and diseases noted above, a compound of this present disclosure may be administered orally, subcutaneously, topically, parenterally, by inhalation spray or rectally in dosage unit formulations containing conventional non-toxic pharmaceutically acceptable carriers, adjuvants and vehicles. Parenteral administration may include subcutaneous injections, intravenous or intramuscular injections or infusion techniques.

Treatment can be continued for as long or as short a period as desired. A suitable treatment period can be, for example, at least about one week, at least about two weeks, at least about one month, at least about six months, at least about 1 year, or indefinitely. A treatment period can terminate when a desired result, for example a weight loss target, is achieved. A treatment regimen can include a corrective phase, during which dose sufficient to provide reduction of weight is administered, and can be followed by a maintenance phase, during which a e.g. a lower dose sufficient to prevent weight gain is administered. A suitable maintenance dose is likely to be found in the lower parts of the dose ranges provided herein, but corrective and maintenance doses can be readily established for individual subjects by those of skill in the art without undue experimentation, based on the disclosure herein. Maintenance doses can be employed to maintain body weight in subjects whose body weight has been previously controlled by other means, including diet and exercise, bariatric procedures such as bypass or banding surgeries, or treatments employing other pharmacological agents.

III. Pharmaceutical Compositions and Kits

Another aspect of the present disclosure provides pharmaceutical compositions comprising compounds as disclosed herein formulated together with a pharmaceutically acceptable carrier. In particular, the present disclosure provides pharmaceutical compositions comprising compounds as disclosed herein formulated together with one or more pharmaceutically acceptable carriers. These formulations include those suitable for oral, rectal, topical, buccal, parenteral (e.g., subcutaneous, intramuscular, intradermal, or intravenous) rectal, vaginal, or aerosol administration, although the most suitable form of administration in any given case will depend on the degree and severity of the condition being treated and on the nature of the particular compound being used. For example, disclosed compositions may be formulated as a unit dose, and/or may be formulated for oral or subcutaneous administration.

Exemplary pharmaceutical compositions of this disclosure may be used in the form of a pharmaceutical preparation, for example, in solid, semisolid or liquid form, which contains one or more disclosed compounds, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The active object compound is included in the pharmaceutical composition in an amount sufficient to produce the desired effect upon the process or condition of the disease.

For preparing solid compositions such as tablets, the principal active ingredient may be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a disclosed compound, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the subject composition moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art.

Compositions for inhalation or insufflation include solutions and suspensions in pharmaceutically acceptable, aqueous or organic solvents, or mixtures thereof, and powders. Liquid dosage forms for oral administration include pharmaceutically acceptable emulsions, microemulsions, solutions, suspensions, syrups and elixirs. In addition to the subject composition, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, cyclodextrins and mixtures thereof.

Suspensions, in addition to the subject composition, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing a subject composition with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent.

Dosage forms for transdermal administration of a subject composition include powders, sprays, ointments, pastes, creams, lotions, gels, solutions, patches and inhalants. The active component may be mixed under sterile conditions with a pharmaceutically acceptable carrier, and with any preservatives, buffers, or propellants which may be required.

The ointments, pastes, creams and gels may contain, in addition to a subject composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to a subject composition, excipients such as lactose, talc, silicic acid, aluminum hydroxide, calcium silicates and polyamide powder, or mixtures of these substances. Sprays may additionally contain customary propellants, such as chlorofluorohydrocarbons and volatile unsubstituted hydrocarbons, such as butane and propane.

Compositions and compounds of the present disclosure may alternatively be administered by aerosol. This is accomplished by preparing an aqueous aerosol, liposomal preparation or solid particles containing the compound. A non-aqueous (e.g., fluorocarbon propellant) suspension could be used. Sonic nebulizers may be used because they minimize exposing the agent to shear, which may result in degradation of the compounds contained in the subject compositions. Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Pharmaceutical compositions of this disclosure suitable for parenteral administration comprise a subject composition in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions of the present disclosure include water, ethanol, polyols (such as glycerol, propylene glycol, polyethylene glycol, and the like), and suitable mixtures thereof, vegetable oils, such as olive oil, and injectable organic esters, such as ethyl oleate and cyclodextrins. Proper fluidity may be maintained, for example, by the use of coating materials, such as lecithin, by the maintenance of the required particle size in the case of dispersions, and by the use of surfactants In another aspect, the present disclosure provides enteral pharmaceutical formulations including a disclosed compound and an enteric material; and a pharmaceutically acceptable carrier or excipient thereof. Enteric materials refer to polymers that are substantially insoluble in the acidic environment of the stomach, and that are predominantly soluble in intestinal fluids at specific pHs. The small intestine is the part of the gastrointestinal tract (gut) between the stomach and the large intestine, and includes the duodenum, jejunum, and ileum. The pH of the duodenum is about 5.5, the pH of the jejunum is about 6.5 and the pH of the distal ileum is about 7.5. Accordingly, enteric materials are not soluble, for example, until a pH of about 5.0, of about 5.2, of about 5.4, of about 5.6, of about 5.8, of about 6.0, of about 6.2, of about 6.4, of about 6.6, of about 6.8, of about 7.0, of about 7.2, of about 7.4, of about 7.6, of about 7.8, of about 8.0, of about 8.2, of about 8.4, of about 8.6, of about 8.8, of about 9.0, of about 9.2, of about 9.4, of about 9.6, of about 9.8, or of about 10.0. Exemplary enteric materials include cellulose acetate phthalate (CAP), hydroxypropyl methylcellulose phthalate (HPMCP), polyvinyl acetate phthalate (PVAP), hydroxypropyl methylcellulose acetate succinate (HPMCAS), cellulose acetate trimellitate, hydroxypropyl methylcellulose succinate, cellulose acetate succinate, cellulose acetate hexahydrophthalate, cellulose propionate phthalate, cellulose acetate maleate, cellulose acetate butyrate, cellulose acetate propionate, copolymer of methylmethacrylic acid and methyl methacrylate, copolymer of methyl acrylate, methylmethacrylate and methacrylic acid, copolymer of methylvinyl ether and maleic anhydride (Gantrez ES series), ethyl methyacrylate-methylmethacrylate-chlorotrimethylammonium ethyl acrylate copolymer, natural resins such as zein, shellac and copal collophorium, and several commercially available enteric dispersion systems (e. g., Eudragit L30D55, Eudragit FS30D, Eudragit L100, Eudragit S100, Kollicoat EMM30D, Estacryl 30D, Coateric, and Aquateric). The solubility of each of the above materials is either known or is readily determinable in vitro. The foregoing is a list of possible materials, but one of skill in the art with the benefit of the disclosure would recognize that it is not comprehensive and that there are other enteric materials that would meet the objectives of the present invention.

Advantageously, the present disclosure also provides kits for use by e.g. a consumer in need of weight loss. Such kits include a suitable dosage form such as those described above and instructions describing the method of using such dosage form to mediate, reduce or prevent inflammation. The instructions would direct the consumer or medical personnel to administer the dosage form according to administration modes known to those skilled in the art. Such kits could advantageously be packaged and sold in single or multiple kit units. An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc. . . . Second Week, Monday, Tuesday, . . ." etc. Other variations of memory aids will be readily apparent. A "daily dose" can be a single tablet or capsule or several pills or capsules to be taken on a given day. Also, a daily dose of a first compound can consist of one tablet or capsule while a daily dose of the second compound can consist of several tablets or capsules and vice versa. The memory aid should reflect this.

Also contemplated herein are methods and compositions that include a second active agent, or administering a second active agent. For example, in addition to being overweight or obese, a subject or patient can further have overweight- or obesity-related co-morbidities, i.e., diseases and other adverse health conditions associated with, exacerbated by, or precipitated by being overweight or obese. Contemplated herein are disclosed compounds in combination with at least one other agent that has previously been shown to treat these overweight- or obesity-related conditions.

For example, Type II diabetes has been associated with obesity. Certain complications of Type II diabetes, e.g., disability and premature death, can be prevented, ameliorated, or eliminated by sustained weight loss (Astrup, A. Pub Health Nutr (2001) 4:499-5 15). Agents administered to treat Type II diabetes include sulfonylureas (e.g., Chlorpropamide, Glipizide, Glyburide, Glimepiride); meglitinides (e.g., Repaglinide and Nateglinide); biguanides (e.g., Metformin); thiazolidinediones (Rosiglitazone, Troglitazone, and Pioglitazone); dipeptidylpeptidase-4 inhibitors (e.g., Sitagliptin, Vildagliptin, and Saxagliptin); glucagon-like peptide-1 mimetics (e.g., Exenatide and Liraglutide); and alpha-glucosidase inhibitors (e.g., Acarbose and Miglitol).

Cardiac disorders and conditions, for example hypertension, dyslipidemia, ischemic heart disease, cardiomyopathy, cardiac infarction, stroke, venous thromboembolic disease and pulmonary hypertension, have been linked to overweight or obesity. For example, hypertension has been linked to obesity because excess adipose tissue secretes substances that are acted on by the kidneys, resulting in hypertension. Additionally, with obesity there are generally higher amounts of insulin produced (because of the excess adipose tissue) and this excess insulin also elevates blood pressure. A major treatment option of hypertension is weight loss. Agents administered to treat hypertension include Chlorthalidone; Hydrochlorothiazide; Indapamide, Metolazone; loop diuretics (e.g., Bumetanide, Ethacrynic acid, Furosemide, Lasix, Torsemide); potassium-sparing agents (e.g., Amiloride hydrochloride, benzamil, Spironolactone, and Triamterene); peripheral agents (e.g., Reserpine); central alpha-agonists (e.g., Clonidine hydrochloride, Guanabenz acetate, Guanfacine hydrochloride, and Methyldopa); alpha-blockers (e.g., Doxazosin mesylate, Prazosin hydrochloride, and Terazosin hydrochloride); beta-blockers (e.g., Acebutolol, Atenolol, Betaxolol, Bisoprolol fumarate, Carteolol hydrochloride, Metoprolol tartrate, Metoprolol succinate, Nadolol, Penbutolol sulfate, Pindolol, Propranolol hydrochloride, and Timolol maleate); combined alpha- and beta-blockers (e.g., Carvedilol and Labetalol hydrochloride); direct vasodilators (e.g., Hydralazine hydrochloride and Minoxidil); calcium antagonists (e.g., Diltiazem hydrochloride and Verapamil hydrochloride); dihydropyridines (e.g., Amlodipine besylate, Felodipine, Isradipine, Nicardipine, Nifedipine, and Nisoldipine); ACE inhibitors (benazepril hydrochloride, Captopril, Enalapril maleate, Fosinopril sodium, Lisinopril, Moexipril, Quinapril hydrochloride, Ramipril, Trandolapril); Angiotensin II receptor blockers (e.g., Losartan potassium, Valsartan, and Irbesartan); Renin inhibitors (e.g., Aliskiren); and combinations thereof. These compounds are administered in regimens and at dosages known in the art.

Carr et al. (The Journal of Clinical Endocrinology & Metabolism (2004) Vol. 89, No. 6 2601-2607) discusses a link between being overweight or obese and dyslipidemia. Dyslipidemia is typically treated with statins. Statins, HMG-CoA reductase inhibitors, slow down production of cholesterol in a subject and/or remove cholesterol buildup from arteries. Statins include mevastatin, lovastatin, pravastatin, simvastatin, velostatin, dihydrocompactin, fluvastatin, atorvastatin, dalvastatin, carvastatin, crilvastatin, bevastatin, cefvastatin, rosuvastatin, pitavastatin, and glenvastatin. These compounds are administered in regimens and at dosages known in the art. Eckel (Circulation (1997) 96:3248-3250) discusses a link between being overweight or obese and ischemic heart disease. Agents administered to treat ischemic heart disease include statins, nitrates (e.g., Isosorbide Dinitrate and Isosorbide Mononitrate), beta-blockers, and calcium channel antagonists. These compounds are administered in regimens and at dosages known in the art.

Wong et al. (Nature Clinical Practice Cardiovascular Medicine (2007) 4:436-443) discusses a link between being overweight or obese and cardiomyopathy. Agents administered to treat cardiomyopathy include inotropic agents (e.g., Digoxin), diuretics (e.g., Furosemide), ACE inhibitors, calcium antagonists, anti-arrhythmic agents (e.g., Sotolol, Amiodarone and Disopyramide), and beta-blockers. These compounds are administered in regimens and at dosages known in the art. Yusef et al. (Lancet (2005) 366(9497): 1640-1649) discusses a link between being overweight or obese and cardiac infarction. Agents administered to treat cardiac infarction include ACE inhibitors, Angiotensin II receptor blockers, direct vasodilators, beta blockers, anti-arrhythmic agents and thrombolytic agents (e.g., Alteplase, Retaplase, Tenecteplase, Anistreplase, and Urokinase). These compounds are administered in regimens and at dosages known in the art.

Suk et al. (Stroke (2003) 34:1586-1592) discusses a link between being overweight or obese and strokes. Agents administered to treat strokes include anti-platelet agents (e.g., Aspirin, Clopidogrel, Dipyridamole, and Ticlopidine), anticoagulant agents (e.g., Heparin), and thrombolytic agents. Stein et al. (The American Journal of Medicine (2005) 18(9):978-980) discusses a link between being overweight or obese and venous thromboembolic disease. Agents administered to treat venous thromboembolic disease include anti-platelet agents, anticoagulant agents, and thrombolytic agents. Sztrymf et al. (Rev Pneumol Clin (2002) 58(2): 104-10) discusses a link between being overweight or obese and pulmonary hypertension. Agents administered to treat pulmonary hypertension include inotropic agents, anticoagulant agents, diuretics, potassium (e.g., K-dur), vasodilators (e.g., Nifedipine and Diltiazem), Bosentan, Epoprostenol, and Sildenafil. Respiratory disorders and conditions such as obesity-hypoventilation syndrome, asthma, and obstructive sleep apnea, have been linked to being overweight or obese. Elamin (Chest (2004) 125:1972-1974) discusses a link between being overweight or obese and asthma. Agents administered to treat asthma include bronchodilators, anti-inflammatory agents, leukotriene blockers, and anti-Ige agents. Particular asthma agents include Zafirlukast, Flunisolide, Triamcinolone, Beclomethasone, Terbutaline, Fluticasone, Formoterol, Beclomethasone, Salmeterol, Theophylline, and Xopenex.

Kessler et al. (Eur Respir J (1996) 9:787-794) discusses a link between being overweight or obese and obstructive sleep apnea. Agents administered to treat sleep apnea include Modafinil and amphetamines.

Hepatic disorders and conditions, such as nonalcoholic fatty liver disease, have been linked to being overweight or obese. Tolman et al. (Ther Clin Risk Manag (2007) 6:1153-1163) discusses a link between being overweight or obese and nonalcoholic fatty liver disease. Agents administered to treat nonalcoholic fatty liver disease include antioxidants (e.g., Vitamins E and C), insulin sensitizers (Metformin, Pioglitazone, Rosiglitazone, and Betaine), hepatoprotectants, and lipid-lowering agents.

Skeletal disorders and conditions, such as, back pain and osteoarthritis of weight-bearing joints, have been linked to being overweight or obese. van Saase (J Rheumatol (1988) 15(7):1152-1158) discusses a link between being overweight or obese and osteoarthritis of weight-bearing joints. Agents administered to treat osteoarthritis of weight-bearing joints include Acetaminophen, non-steroidal anti-inflammatory agents (e.g., Ibuprofen, Etodolac, Oxaprozin, Naproxen, Diclofenac, and Nabumetone), COX-2 inhibitors (e.g., Celecoxib), steroids, supplements (e.g. glucosamine and chondroitin sulfate), and artificial joint fluid.

Metabolic disorders and conditions, for example, Prader-Willi Syndrome and polycystic ovary syndrome, have been linked to being overweight or obese. Agents administered to treat Prader-Willi Syndrome include human growth hormone (HGH), somatropin, and weight loss agents (e.g., Orlistat, Sibutramine, Methamphetamine, lonamin, Phentermine, Bupropion, Diethylpropion, Phendimetrazine, Benzphetermine, and Topamax).

Hoeger (Obstetrics and Gynecology Clinics of North America (2001) 28(1):85-97) discusses a link between being overweight or obese and polycystic ovary syndrome. Agents administered to treat polycystic ovary syndrome include insulin-sensitizers, combinations of synthetic estrogen and progesterone, Spironolactone, Eflornithine, and Clomiphene. Reproductive disorders and conditions such as sexual dysfunction, erectile dysfunction, infertility, obstetric complications, and fetal abnormalities, have been linked to being overweight or obese. Larsen et al. (Int J Obes (Lond) (2007) 8:1189-1198) discusses a link between being overweight or obese and sexual dysfunction. Chung et al. (Eur Urol (1999) 36(1):68-70) discusses a link between being overweight or obese and erectile dysfunction. Agents administered to treat erectile dysfunction include phosphodiesterase inhibitors (e.g., Tadalafil, Sildenafil citrate, and Vardenafil), prostaglandin E analogs (e.g., Alprostadil), alkaloids (e.g., Yohimbine), and testosterone. Pasquali et al. (Hum Reprod (1997) 1:82-87) discusses a link between being overweight or obese and infertility. Agents administered to treat infertility include Clomiphene, Clomiphene citrate, Bromocriptine, Gonadotropin-releasing Hormone (GnRH), GnRH agonist, GnRH antagonist, Tamoxifen/nolvadex, gonadotropins, Human Chorionic Gonadotropin (HCG), Human Menopausal Gonadotropin (HmG), progesterone, recombinant follicle stimulating hormone (FSH), Urofollitropin, Heparin, Follitropin alfa, and Follitropin beta.

Weiss et al. (American Journal of Obstetrics and Gynecology (2004) 190(4):1091-1097) discusses a link between being overweight or obese and obstetric complications. Agents administered to treat obstetric complications include Bupivacaine hydrochloride, Dinoprostone PGE2, Meperidine HCl, Ferro-folic-500/iberet-folic-500, Meperidine, Methylergonovine maleate, Ropivacaine HCl, Nalbuphine HCl, Oxymorphone HCl, Oxytocin, Dinoprostone, Ritodrine, Scopolamine hydrobromide, Sufentanil citrate, and Oxytocic.

Psychiatric disorders and conditions, for example, weight-associated depression and anxiety, have been linked to being overweight or obese. Dixson et al. (Arch Intern Med (2003) 163:2058-2065) discusses a link between being overweight or obese and depression. Agents administered to treat depression include serotonin reuptake inhibitors (e.g., Fluoxetine, Escitalopram, Citalopram, Paroxetine, Sertraline, and Venlafaxine); tricyclic antidepressants (e.g., Amitriptyline, Amoxapine, Clomipramine, Desipramine, Dosulepin hydrochloride, Doxepin, Imipramine, Iprindole, Lofepramine, Nortriptyline, Opipramol, Protriptyline, and Trimipramine); monoamine oxidase inhibitors (e.g., Isocarboxazid, Moclobemide, Phenelzine, Tranylcypromine, Selegiline, Rasagiline, Nialamide, Iproniazid, Iproclozide, Toloxatone, Linezolid, Dienolide kavapyrone desmethoxyyangonin, and Dextroamphetamine); psychostimulants (e.g., Amphetamine, Methamphetamine, Methylphenidate, and Arecoline); antipsychotics (e.g., Butyrophenones, Phenothiazines, Thioxanthenes, Clozapine, Olanzapine, Risperidone, Quetiapine, Ziprasidone, Amisulpride, Paliperidone, Symbyax, Tetrabenazine, and Cannabidiol); and mood stabilizers (e.g., Lithium carbonate, Valproic acid, Divalproex sodium, Sodium valproate, Lamotrigine, Carbamazepine, Gabapentin, Oxcarbazepine, and Topiramate).

Simon et al. (Archives of General Psychiatry (2006) 63(7):824-830) discusses a link between being overweight or obese and anxiety. Agents administered to treat anxiety include serotonin reuptake inhibitors, mood stabilizers, benzodiazepines (e.g., Alprazolam, Clonazepam, Diazepam, and Lorazepam), tricyclic antidepressants, monoamine oxidase inhibitors, and beta-blockers.

Another aspect of the present disclosure provides methods for facilitating and maintaining weight loss in a subject involving administering to the subject an amount of a disclosed compound effective to result in weight loss in the subject; and optionally administering a therapeutically effective amount of a different weight loss agent to maintain a reduced weight in the subject. Weight loss agents include serotonin and noradrenergic re-uptake inhibitors; noradrenergic re-uptake inhibitors; selective serotonin re-uptake inhibitors; and intestinal lipase inhibitors. Particular weight loss agents include orlistat, sibutramine, methamphetamine, ionamin, phentermine, bupropion, diethylpropion, phendimetrazine, benzphetermine, bromocriptine, lorcaserin, topiramate, or agents acting to modulate food intake by blocking ghrelin action, inhibiting diacylglycerol acyltransferase 1 (DGAT1) activity, inhibiting stearoyl CoA desaturase 1 (SCD1) activity, inhibiting neuropeptide Y receptor 1 function, activating neuropeptide Y receptor 2 or 4 function, or inhibiting activity of sodium-glucose cotransporters 1 or 2. These compounds are administered in regimens and at dosages known in the art.

EXAMPLES

The compounds described herein can be prepared in a number of ways based on the teachings contained herein and synthetic procedures known in the art. In the description of the synthetic methods described below, it is to be understood that all proposed reaction conditions, including choice of solvent, reaction atmosphere, reaction temperature, duration of the experiment and workup procedures, can be chosen to be the conditions standard for that reaction, unless otherwise indicated. It is understood by one skilled in the art of organic synthesis that the functionality present on various portions of the molecule should be compatible with the reagents and reactions proposed. Substituents not compatible with the reaction conditions will be apparent to one skilled in the art, and alternate methods are therefore indicated. The starting materials for the examples are either commercially available or are readily prepared by standard methods from known materials.

At least some of the compounds identified as "Intermediates" herein are contemplated as compounds of the present disclosure.

Example A

General Procedures

All reagents were purchased from commercial suppliers (Sigma-Aldrich, Alfa, Across etc.) and used without further purification unless otherwise stated. THF was continuously refluxed and freshly distilled from sodium and benzophenone under nitrogen, and dichloromethane was continuously refluxed and freshly distilled from $CaH_2$ under nitrogen.

Reactions were monitored by TLC on silica gel 60 HSGF254 percolated plates (0.15-0.2 mm SiO2) and visualized using UV light (254 nm or 365 nm) and/or staining with phosphomolybdic acid ethanol solution (10 g in 100 mL ethanol) and subsequent heating or monitored by LCMS.

LCMS were performed on SHIMADZU LCMS-2010EV (Chromolith SpeedROD, RP-18e, 50×4.6 mm, mobile phase: Solvent A: $CH_3CN/H_2O/HCOOH=10/90/0.05$, Solvent B: $CH_3CN/H_2O/HCOOH=90/10/0.05$, 0.8 min@ 10% B, 2.7 min gradient (10-95% B), then 0.8 min@95% B, Flow rate: 3 mL/min, temperature: 40° C.).

Preparative HPLC were performed either on Method A: SHIMADZU LC-8A (Column: YMC Pack ODS-A (150*30 mm, 10 μm)) or Method B: LC-6AD (Column: Shim=Pack PREP-ODS-H (250*20 mm, 10 μm)) with UV detection which were controlled by LC solution Chemstation software. $H_2O$ (0.1% HCOOH) and MeOH (MeCN) as mobile phase at the indicated flow rate.

Analytical HPLC were performed on SHIMADZU LC-2010A (Chromolith SpeedROD, RP-18e, 50×4.6 mm, mobile phase: Solvent A: $CH_3CN/H_2O/HCOOH=10/90/0.05$, Solvent B: $CH_3CN/H_2O/HCOOH=90/10/0.05$, 0.8 min@ 10% B, 2.7 min gradient (10-95% B), then 0.8 min@95% B, Flow rate: 3 mL/min, temperature: 40° C.).

Chiral HPLC were performed on SHIMADZU LC-2010A (Chiral column, mobile phase: Solvent A: hexane (or containing 0.1% diethylamine), Solvent B: Ethanol or Isopropanol; Flow rate: 0.8 mL/min, temperature: 30° C.).

$^1$H spectra were recorded on Bruker Avance II 400 MHz, Chemical shifts (δ) are reported in ppm relative to tetramethylsilane (δ=0.000 ppm), and the spectra were calibrated to the residual solvent signal of chloroform (δ=7.26), Dimethyl sulfoxide (δ=2.50), or methanol (δ=3.30). Data for $^1$H-NMR spectra are reported as follows: chemical shift (multiplicity, number of hydrogens). Abbreviations are as follows: s (singlet), d (doublet), t (triplet), q (quartet), quint (quintet), m (multiple), br (broad).

| Abbreviations: | |
|---|---|
| Ac | Acetyl |
| AcOH; HOAc | acetic acid |
| aq. | Aqueous |
| Bs | Benzenesulfonyl |
| Cbz | Benzyloxycarbonyl |
| CDI | Carbonyldimidazole |
| DCM | Dichloromethane |
| DEAD | Diethyl azodicarboxylate |
| DIPEA | Ethyldiisopropylamine |
| DMA | Dimethyl acetamide |
| DMF | Dimethyl formamide |
| EDCI/EDC | 3-(ethyliminomethyleneamino)-N,N-dimethylpropan-1-amine |
| EtOH | Ethanol |
| eq(s). | equivalent(s) |
| EtOAc | ethyl acetate |
| Et | Ethyl |
| FA | Formic acid |
| $Et_3N$ | Triethylamine |
| hr | hour(s) |
| HATU | (Dimethylamino)-N,N-dimethyl(3H-[1,2,3]triazolo[4,5-b]pyridin-3-yloxy)methaniminium hexafluorophosphate |
| HOBt | 1-Hydroxybenzotriazole |
| HPLC | High pressure liquid chromatography |
| LAH | Lithium Aluminum Hydride |
| LCMS; LC-MS | liquid chromatography mass spectrometry |
| m-CPBA | m-Chloroperoxybenzoic acid |
| MeOH | Methanol |
| mg | milligram(s) |
| min | Minute(s) |
| mL; ml | milliliter(s) |
| NCS | N-Chlorosuccinimide |
| NMe | N-methyl |
| NMO | N-methylmorpholine-N-oxide |
| NMP | N-methylpyrrolidinone |
| NMR | Nuclear magnetic resonance |
| $Pd(dppf)Cl_2$ | (1,1'-bis(diphenylphosphino)ferrocene) palladium (II) dichloride |
| PE | Petroleum Ether |
| Ph | Phenyl |
| PTSA | p-Toluenesulfonic acid |
| r.t./RT | Room temperature |
| S. | Saturated |
| SEMCl | 2-(Trimethylsilyl)ethoxymethyl chloride |
| TBAF | Tetrabutylammonium fluoride |
| TEA | Triethylamine |
| THF | Tetrahydrofuran |
| THP | Tetrahydropyran |
| TFA | Trifluoroacetic acid |
| TMSCN | Trimethylsilyl cyanide |

Abbreviations:

| | |
|---|---|
| TMSOTf | Trimethylsilyl Triflate |
| THF | Tetrahydrofuran |
| TLC | Thin layer chromatography |
| Ts | Tosyl (4-methylbenzene-1-sulfonyl) |

Preparation of Intermediates

Intermediate 1

(3R,4S,5S,6R)-5-methoxy-4-((2R,3R)-2-methyl-3-(3-methylbut-2-en-1-yl)oxiran-2-yl)-1-oxaspiro[2.5]octan-6-yl (4-nitrophenyl) carbonate

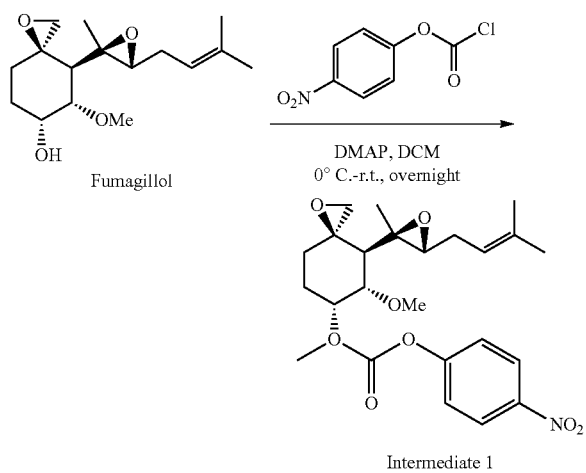

Intermediate 1

Fumagillol (40 g, 0.142 mol) and DMAP (34.6 g, 0.283 mol) were dissolved in anhydrous DCM (480 mL) with stirring at 0° C. A solution of p-nitrophenyl chloroformate (48.65 g, 0.241 mol) in DCM (250 mL) was added dropwise to the mixture above for 1 hr, and the temperature was kept below 0° C. After addition was complete, the mixture was stirred at room temperature for 16 hrs. The mixture was diluted with DCM (500 mL), washed sequentially with a 10% aq. solution of citric acid, saturated aq. $K_2CO_3$ and brine. The organic layer was dried, concentrated and purified by silica gel chromatography (PE:EtOAc=20:1 to PE:EtOAc:DCM=5:1:1). The crude product was washed with PE/EtOAc (100 mL/30 mL) twice, hot EtOH (200 mL, ~70 m° C.), dried under vacuum at r.t. to give (3R,4S,5S,6R)-5-methoxy-4-((2R,3R)-2-methyl-3-(3-methylbut-2-en-1-yl)oxiran-2-yl)-1-oxaspiro[2.5]octan-6-yl (4-nitrophenyl) carbonate as a white solid (47.9 g, 75.4% yield). LC-MS: m/z=448 [M+H]$^+$. $^1$H-NMR (400 MHz, CDCl$_3$) (8.39-8.23 (m, 2H), 7.53-7.34 (m, 2H), 5.63 (d, J=2.8 Hz, 1H), 5.23 (t, J=7.4 Hz, 1H), 3.74 (dd, J=11.3, 2.6 Hz, 1H), 3.03 (d, J=4.2 Hz, 1H), 2.69-2.53 (m, 2H), 2.50-2.33 (m, 1H), 2.27-1.90 (m, 5H), 1.77 (s, 3H), 1.68 (s, 3H), 1.37-1.06 (m, 4H).

Procedures for preparation of additional intermediates and compounds of the present disclosure are described in the following examples.

Intermediate 2

7-methyl-7-azaspiro[3.5]nonan-2-amine

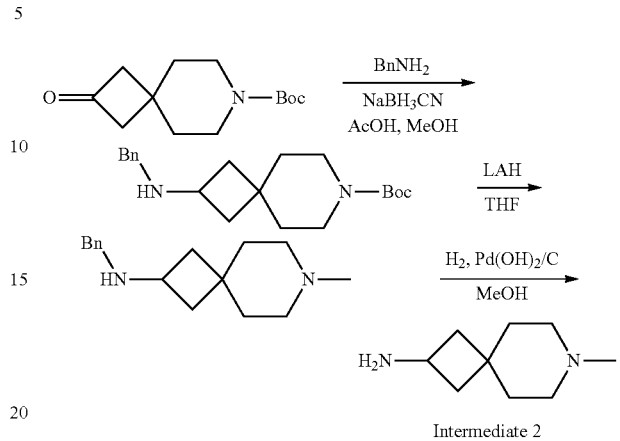

Intermediate 2

Step 1: tert-butyl 2-(benzylamino)-7-azaspiro[3.5]nonane-7-carboxylate

To a solution of tert-butyl 2-oxo-7-azaspiro[3.5]nonane-7-carboxylate (1.2 g, 5.02 mmol) in methanol (20 mL) was added benzylamine (0.73 mL, 6.28 mmol) and acetic acid (0.83 mL, 21.3 mmol) at 0° C. After addition was complete, the mixture was stirred at 0° C. for 20 mins. Sodium cyanoborohydride (327 mg, 5.02 mmol) was added in portions, and the reaction was stirred at 0° C. for 3 hrs. The reaction was quenched by the addition of aqueous sodium hydroxide (20% wt). Then the mixture was diluted with water and extracted with EtOAc (30 mL×2). The combined organic layers were washed with brine, dried over anhydrous Na$_2$SO$_4$ and concentrated under reduced pressure to give a residue, which was purified by silica gel chromatography (PE:EtOAc=3:1) to give tert-butyl 2-(benzylamino)-7-azaspiro[3.5]nonane-7-carboxylate (1.2 g, 72.2% yield) as a yellow solid. LC-MS: m/z=331 [M+H]$^+$.

Step 2: N-benzyl-7-methyl-7-azaspiro[3.5]nonan-2-amine

To a suspension of lithium aluminium hydride (206 mg, 5.43 mmol) in THF (7 mL) was added a solution of tert-butyl 2-(benzylamino)-7-azaspiro[3.5]nonane-7-carboxylate (600 mg, 1.81 mmol) in THF (3 mL) drop-wise at 0° C. The reaction was stirred at 75° C. for 45 mins. The reaction was quenched by the addition of water (0.3 mL), aqueous sodium hydroxide (0.3 mL, 15% wt) and water (0.6 mL). The solids were removed through filtration and washed with THF. The filtrate was dried over anhydrous Na$_2$SO$_4$ and concentrated under reduced pressure to give N-benzyl-7-methyl-7-azaspiro[3.5]nonan-2-amine (405 mg, 91.3% yield) as a colorless oil. LC-MS: m/z=245 [M+H]$^+$.

Step 3: 7-methyl-7-azaspiro[3.5]nonan-2-amine

A solution of N-benzyl-7-methyl-7-azaspiro[3.5]nonan-2-amine (350 mg, 1.43 mmol) in methanol (10 mL) was degassed under N$_2$ atmosphere three times, and Pd(OH)$_2$ on carbon (130 mg) was added. The mixture was degassed with N$_2$ again and stirred under a H$_2$ atmosphere at room temperature overnight. The mixture was filtered through Celite, and the filtrate was concentrated to give 7-methyl-7-azaspiro[3.5]nonan-2-amine (190 mg, 85.5% yield) as a colorless oil. LC-MS: m/z=155 [M+H]$^+$.

Intermediate 3

7-methyl-2,7-diazaspiro[3.5]nonan, trifluoroacetate

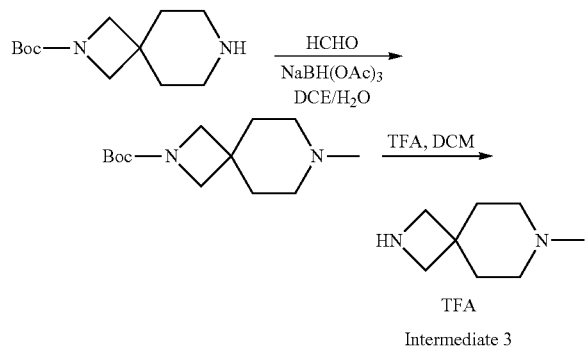

Intermediate 3

Step 1: tert-butyl 3-(2-morpholinoethyl)azetidine-1-carboxylate

To a solution of tert-butyl 2,7-diazaspiro[3.5]nonane-2-carboxylate (600 mg, 2.65 mmol) in DCE (10 mL) was added an aqueous solution of formaldehyde (37 percent w/w, 238 mg, 3.98 mmol). After the reaction was stirred at room temperature for 10 min, sodium triacetoxyborohydride (1.69 g, 7.95 mmol) was added and the mixture was stirred for another 3 hrs. After the solvent was removed, the residue was dissolved in EtOAc and washed with brine. The EtOAc layer was dried and concentrated to give a residue, which was purified by silica gel chromatography (DCM:MeOH=100:1 to 10:1) to give tert-butyl 3-(2-morpholinoethyl)azetidine-1-carboxylate (410 mg, 64.35% yield) as a white solid. LC-MS: m/z=185 [M+H]$^+$

Step 2: 7-methyl-2,7-diazaspiro[3.5]nonan, trifluoroacetate

To a solution of tert-butyl 3-(2-morpholinoethyl)azetidine-1-carboxylate (400 mg, 1.66 mmol) in DCM (5 mL) was added TFA (2.5 mL) drop-wise at 0° C. The reaction was stirred room temperature for 1 hr. The mixture was concentrated under reduced pressure to give 7-methyl-2,7-diazaspiro[3.5]nonane trifluoroacetate (390 mg, 96.1% yield) as a yellow syrup, which was directly used to the next reaction without purification. LC-MS: m/z=141 [M+H]$^+$.

Intermediate 4

7-(2,2-difluoroethyl)-2,7-diazaspiro[3.5]nonane trifluoroacetate

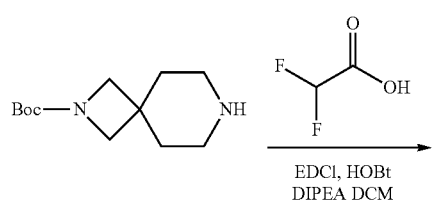

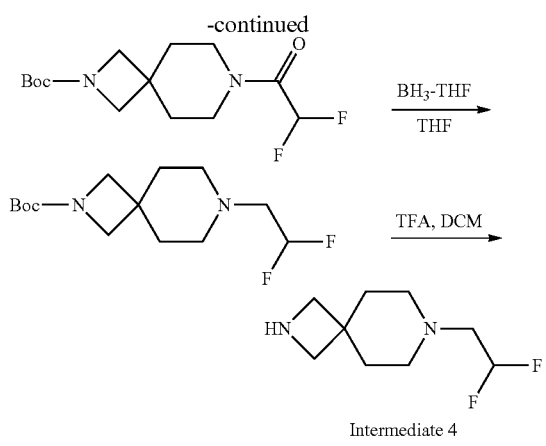

Intermediate 4

Step 1: tert-butyl 7-(2,2-difluoroacetyl)-2,7-diazaspiro[3.5]nonane-2-carboxylate To a solution of 2,2-difluoroacetic acid (424.3 mg, 4.42 mmol) in DCM (10 mL) was added HOBt (358.0 mg, 2.65 mmol) and 1-(3-dimethylaminopropyl)-3-ethylcarbodiimide hydrochloride (635.0 mg, 3.31 mmol) in portions at 0° C. The mixture was stirred at 0° C. for 30 min, and DIPEA (1.14 g, 12.04 mmol) was added drop-wise. Then tert-butyl 2,7-diazaspiro[3.5]nonane-2-carboxylate (500.0 mg, 2.21 mmol) was added drop-wise at 0° C. The reaction was then stirred at room temperature for 2 hrs. The mixture was then concentrated to dryness while keeping the temperature below 30° C. The residue was suspended in ice-water, and the slurry was stirred for 10 min. The mixture was then filtered, and the filter cake was washed with water, followed by cold EtOH. The filter cake was then dried under vacuum to give a crude product, which was recrystallized with ethanol to give tert-butyl 7-(2,2-difluoroacetyl)-2,7-diazaspiro[3.5]nonane-2-carboxylate (560 mg, 83.3% yield) as a white solid. LC-MS: m/z 305 [M+H]$^+$.

Step 2: tert-butyl 7-(2,2-difluoroethyl)-2,7-diazaspiro[3.5]nonane-2-carboxylate To a solution of tert-butyl 7-(2,2-difluoroacetyl)-2,7-diazaspiro[3.5]nonane-2-carboxylate (560 mg, 1.84 mmol) in THF (anhydrous, 50 mL) was added a solution of borane-tetrahydrofuran complex (6.0 mL, 6.0 mmol, 1M in THF) dropwise at −10° C. over 10 min. The reaction was stirred at room temperature overnight. To the reaction mixture was then added MeOH (20 mL) dropwise at 0° C. After the mixture was stirred at room temperature for 30 min it was concentrated under vacuum. The residue was dissolved in EtOH/water (9 mL/1 mL) and stirred at reflux overnight. The mixture was concentrated under vacuum to give a residue, which was purified by silica gel column chromatography (DCM:methanol=100:1 to 40:1) to give tert-butyl 7-(2,2-difluoroethyl)-2,7-diazaspiro[3.5]nonane-2-carboxylate (470 mg, 89.0% yield) as a colorless oil. LC-MS: m/z 291 [M+H−56]$^+$.

Step 3: 7-(2,2-difluoroethyl)-2,7-diazaspiro[3.5]nonane trifluoroacetate

To a mixture of tert-butyl 7-(2,2-difluoroethyl)-2,7-diazaspiro[3.5]nonane-2-carboxylate (470 mg, 1.62 mmol) in DCM (5 mL) was added TFA (2.0 mL) drop-wise at 0° C.

The reaction was stirred at room temperature for 1 hr. The mixture was concentrated under reduced pressure to give 7-(2,2-difluoroethyl)-2,7-diazaspiro[3.5]nonane trifluoroacetate (400 mg, 95.1% yield) as a yellow syrup, which was directly used to next step without purification. LC-MS: m/z 191 [M+H]⁺.

Intermediate 5

2-methyl-2-azaspiro[3.3]heptan-6-amine

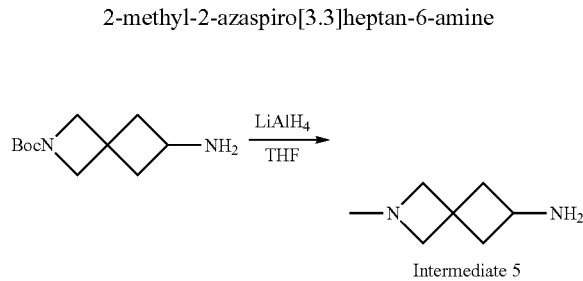

Intermediate 5

Step 1: 2-methyl-2-azaspiro[3.3]heptan-6-amine

To a solution of tert-butyl 6-amino-2-azaspiro[3.3]heptane-2-carboxylate (500 mg, 2.35 mmol) in THF (anhydrous, 5 mL) was added lithium aluminium hydride (268.8 mg, 7.07 mmol) in portions at 0° C. The mixture was heated to 65° C. overnight. The mixture was quenched by aqueous sodium hydroxide solution (0.3 mL, 15% wt) and water (0.3 mL). The slurry was filtered and the filter cake was washed with dichloromethane twice, the combined filtrates was dried over anhydrous Na₂SO₄ and concentrated to give (R)-(1-methylpyrrolidin-2-yl)methanol (290.2 mg, 97.6% yield) as a yellow oil. LC-MS: m/z 127 [M+H]⁺.

Intermediate 6

6-methyl-6-azaspiro[3.4]octan-2-amine

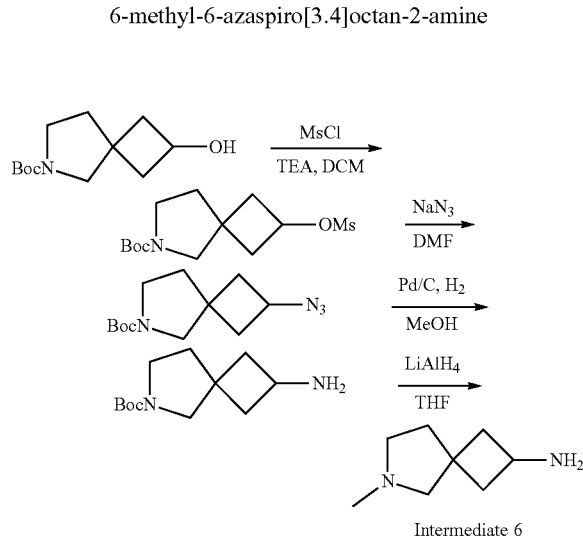

Intermediate 6

Step 1: tert-butyl 2-((methylsulfonyl)oxy)-6-azaspiro[3.4]octane-6-carboxylate

To a solution of tert-butyl 2-hydroxy-6-azaspiro[3.4]octane-6-carboxylate (1 g, 4.41 mmol) in dichloromethane (10 mL) was added triethylamine (1.22 mL, 8.82 mmol) followed by methanesulfonyl chloride (0.5 mL, 6.62 mmol) drop-wise at 0° C. The reaction was stirred at room temperature overnight. The mixture was diluted with dichloromethane and washed with brine, dried over anhydrous Na₂SO₄ and concentrated. The residue was purified by silica gel column chromatography (petroleum ether:ethyl acetate=3:1) to give the titled compound (1.3 g, 97.1% yield) as a colorless oil. LC-MS: m/z 250 [M+H−56]⁺.

Step 2: tert-butyl 2-azido-6-azaspiro[3.4]octane-6-carboxylate

To a solution of tert-butyl 2-((methylsulfonyl)oxy)-6-azaspiro[3.4]octane-6-carboxylate (1.3 g, 4.24 mmol) in DMF (15 mL) was added sodium azide (414 mg, 6.37 mmol) in portions at 0° C. The mixture was stirred at 80° C. overnight. The mixture was diluted with diethyl ether and washed with brine, dried over Na₂SO₄ and concentrated to give 1-(azidomethyl)-4-methoxybenzene (1.02 g, 93.4% yield) as a yellow oil, which was used in next step without further purification.

Step 3: tert-butyl 2-amino-6-azaspiro[3.4]octane-6-carboxylate

A solution of tert-butyl 2-azido-6-azaspiro[3.4]octane-6-carboxylate (1 g, 3.96 mmol) in MeOH (20 mL) was degassed under N₂ atmosphere for three times, then Pd/C (100 mg, 10% wt) was added in one portion. The mixture was stirred under H₂ atmosphere at room temperature overnight. The mixture was filtered through a pad of celite and the filtrate was concentrated under vacuum to give tert-butyl 2-amino-6-azaspiro[3.4]octane-6-carboxylate (420 mg, 46.7% yield) as a colorless oil. LC-MS: m/z 227 [M+H]⁺.

Step 4: 6-methyl-6-azaspiro[3.4]octan-2-amine

To a solution of tert-butyl 2-amino-6-azaspiro[3.4]octane-6-carboxylate (420 mg, 1.85 mmol) in THF (anhydrous, 10 mL) was added lithium aluminium hydride (211 mg, 5.57 mmol) in portions at 0° C. The mixture was heated to 65° C. overnight. The mixture was quenched by aqueous sodium hydroxide solution (0.3 mL, 15% wt) and water (0.3 mL). The slurry was filtered and the filter cake was washed with dichloromethane twice, the combined filtrates was dried over anhydrous Na₂SO₄ and concentrated to give 6-methyl-6-azaspiro[3.4]octan-2-amine (250 mg, 96.1% yield) as a colorless oil. LC-MS: m/z 141 [M+H]⁺.

Intermediate 7

2-methyl-2,6-diazaspiro[3.3]heptanes oxalate

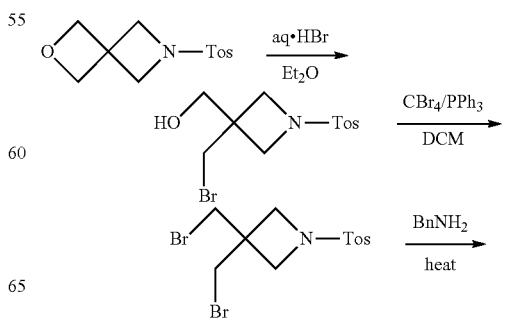

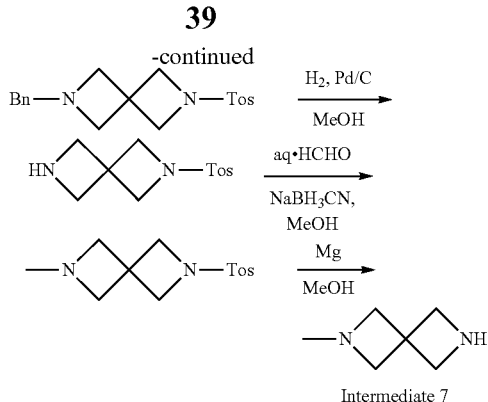

Intermediate 7

Step 1:
(3-(bromomethyl)-1-tosylazetidin-3-yl)methanol

To a mixture of 6-tosyl-2-oxa-6-azaspiro[3.3]heptane (3.0 g, 11.84 mmol) in Et$_2$O (30 mL) was added aq. HBr (4.50 mL, 33.16 mmol, 40%) dropwise at 0° C. The reaction was warmed to room temperature and stirred for 1 hr. The mixture was diluted with ethyl acetate and washed with water, brine, dried over Na$_2$SO$_4$ and concentrated. The residue was purified by silica gel column chromatography (petroleum ether:ethyl acetate=5:1 to 1:1) to give (3-(bromomethyl)-1-tosylazetidin-3-yl)methanol (3.4 g, 84.8% yield) as a white solid. LC-MS: m/z=336 [M+H]$^+$.

Step 2: 3,3-bis(bromomethyl)-1-tosylazetidine

To a mixture of (3-(bromomethyl)-1-tosylazetidin-3-yl)methanol (3.3 g, 9.87 mmol) and CBr$_4$ (5.57 g, 16.78 mmol) in dichloromethane (50 mL) was added PPh$_3$ (4.40 g, 16.78 mmol) at 0° C. under N$_2$. The reaction was stirred at room temperature overnight. The mixture was diluted with dichloromethane, washed with water, brine, dried over anhydrous Na$_2$SO$_4$ and concentrated. The residue was purified by silica gel column chromatography (petroleum ether:ethyl acetate=50:1 to 3:1) to give 3,3-bis(bromomethyl)-1-tosylazetidine (2.1 g, 53.5% yield) as a yellow solid. LC-MS: m/z=397 [M+H]$^+$.

Step 3: 2-benzyl-6-tosyl-2,6-diazaspiro[3.3]heptane

To a mixture of 3,3-bis(bromomethyl)-1-tosylazetidine (1.6 g, 4.03 mmol) in acetonitrile (20 mL) was added benzylamine (1.10 mL, 10.07 mmol) and DIPEA (4.16 mL, 24.17 mmol) drop-wise. The reaction was stirred at reflux overnight. The mixture was concentrated and the residue was dissolved in dichloromethane. The dichloromethane solution was washed with water, brine, dried over Na$_2$SO$_4$ and concentrated. The residue was purified by silica gel column chromatography (petroleum ether:ethyl acetate=5:1 to 2:1) to give 2-benzyl-6-tosyl-2,6-diazaspiro[3.3]heptane (1.2 g, 87.0% yield) as a yellow solid. LC-MS: m/z=343 [M+H]$^+$.

Step 4: 2-tosyl-2,6-diazaspiro[3.3]heptane

To a solution of 2-benzyl-6-tosyl-2,6-diazaspiro[3.3]heptane (1.2 g, 3.50 mmol) in degassed methanol (20 mL) was added Pd/C (120 mg, 10% wt) under N$_2$ atmosphere. The mixture was degassed again and stirred under a H$_2$ atmosphere for 1.5 hrs. The mixture was filtered through Celite, and the filtrate was concentrated under reduced pressure to give 2-tosyl-2,6-diazaspiro[3.3]heptane (880 mg, 99.5% yield) as a white solid. LC-MS: m/z=253 [M+H]$^+$.

Step 5: 2-methyl-6-tosyl-2,6-diazaspiro[3.3]heptane

To a solution of 2-tosyl-2,6-diazaspiro[3.3]heptane (850 g, 3.37 mmol) in methanol (20 mL) was added aqueous HCHO (5.57 mL, 20.21 mmol) followed by sodium cyanoborohydride (2.54 g, 40.42 mmol) in portions at 0° C. The reaction was stirred at room temperature for 1 hr. The reaction mixture was then quenched with saturated aqueous sodium bicarbonate and diluted with ethyl acetate. The organic layer was washed with brine, dried over Na$_2$SO$_4$ and concentrated. The residue was purified by silica gel column chromatography (dichloromethane:methanol=100:0 to 30:1) to give 2-methyl-6-tosyl-2,6-diazaspiro[3.3]heptane (620 mg, 69.1% yield) as a yellow solid. LC-MS: m/z=267 [M+H]$^+$.

Step 6: 2-methyl-2,6-diazaspiro[3.3]heptanes oxalate

To a solution of 2-methyl-6-tosyl-2,6-diazaspiro[3.3]heptane (600 mg, 2.25 mmol) in methanol (30 mL) was added Mg (432.5 mg, 18.02 mmol). The reaction was sonicated for 2 hrs and stirred at reflux overnight. The reaction mixture was concentrated and Na$_2$SO$_4$·10H$_2$O (6.0 g) and ethanol (5 mL) were added. After the mixture was stirred at room temperature for 1 hr, it was filtered and the filtrate was dried over Na$_2$SO$_4$ and concentrated. To the residue was added oxalic acid (101.4 mg, 1.13 mmol) and ethanol (1 mL). The reaction mixture was stirred at room temperature and a yellow precipitate was formed. The solid was filtered and dried to give 2-methyl-2,6-diazaspiro[3.3]heptane oxalic acid salt (300 mg, 65.8% yield) as a yellow solid. LC-MS: m/z=113 [M+H]$^+$.

Intermediate 8

(3aR,6aS)-hexahydro-1H-furo[3,4-c]pyrrole

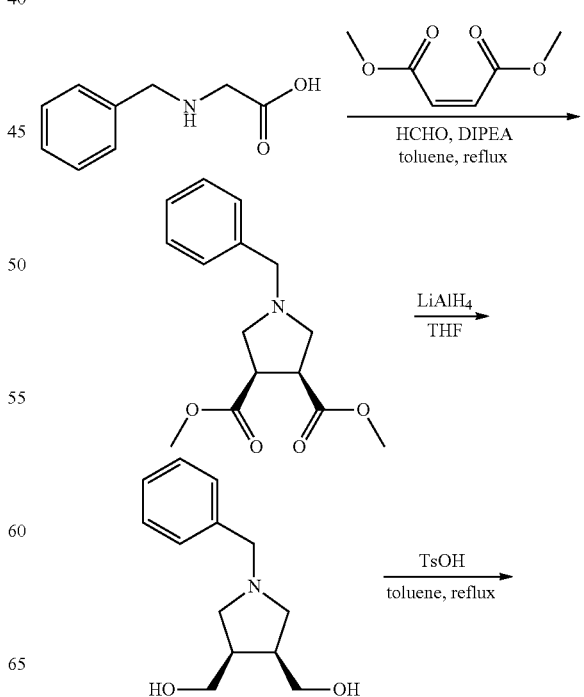

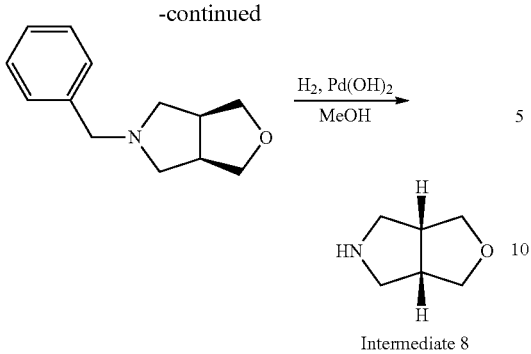

Step 1: (3R,4S)-dimethyl 1-benzylpyrrolidine-3,4-dicarboxylate

To a solution of 2-(benzylamino)acetic acid (5 g, 30.3 mmol) in toluene (30 ml) was added dimethyl maleate (2.90 g, 20.3 mmol), paraformaldehyde (5.45 g, 60.6 mmol) and DIPEA (3.5 ml, 30.3 mmol). The reaction was stirred at reflux overnight. The reaction mixture was diluted with EtOAc and washed with water and brine. The organic layer was dried over anhydrous $Na_2SO_4$ and concentrated under reduced pressure to give a residue, which was purified by silica gel column chromatography (petroleum ether: EtOAc=1:1) to give (3R,4S)-dimethyl 1-benzylpyrrolidine-3,4-dicarboxylate (3 g, 35.8% yield) as a yellow oil. LC-MS: m/z 278 [M+H]$^+$.

Step 2: ((3R,4S)-1-benzylpyrrolidine-3,4-diyl)dimethanol

To a slurry of lithium aluminium hydride (1.0 g, 26.3 mmol) in THF (anhydrous, 15 mL) was added a solution of (3R,4S)-dimethyl 1-benzylpyrrolidine-3,4-dicarboxylate (2.43 g, 8.7 mmol) in THF (anhydrous, 15 mL) dropwise at 0° C. over 30 min. The reaction was stirred at room temperature overnight. The reaction was quenched with water (1 mL), aqueous NaOH solution (1 mL, 15% wt) and water (3 mL) successively. The slurry was filtered and the cake was washed with EtOAc twice. The combined filtrate was dried with anhydrous $Na_2SO_4$ and concentrated to give ((3R,4S)-1-benzylpyrrolidine-3,4-diyl)dimethanol (1.8 g, 94.7% yield) as a yellow oil. LC-MS: m/z 222 [M+H]$^+$.

Step 3: (3aR,6aS)-5-benzylhexahydro-1H-furo[3,4-c]pyrrole

To a solution of ((3R,4S)-1-benzylpyrrolidine-3,4-diyl) dimethanol (1.3 g, 5.9 mmol) in toluene (15 ml) was added p-toluenesulfonic acid (1.3 g, 7.0 mmol). The resulting mixture was heated under a Dean Stark trap at 120° C. for 20 hrs. The reaction mixture was diluted with EtOAc and washed with water and brine. The organic layer was dried over anhydrous $Na_2SO_4$ and concentrated under reduced pressure to give a residue, which was purified by silica gel column chromatography (petroleum ether:ethyl acetate=5:1) to give (3aR,6aS)-5-benzylhexahydro-1H-furo[3,4-c]pyrrole (800 mg, 67.2% yield) as a yellow oil. LC-MS: m/z 204 [M+H]$^+$.

Step 4: (3aR,6aS)-hexahydro-1H-furo[3,4-c]pyrrole

A solution of (3aR,6aS)-5-benzylhexahydro-1H-furo[3,4-c]pyrrole (500 mg, 2.46 mmol) in ethanol (10 mL) was degassed with $N_2$ for three times and Pd(OH)$_2$/C (60 mg, 10% wt) was added. The mixture was degassed again and stirred under $H_2$ atmosphere at room temperature for 16 hrs. The mixture was filtered and the filtrate was concentrated under reduced pressure to give (3aR,6aS)-hexahydro-1H-furo[3,4-c]pyrrole (270 mg, 96.7% yield) as a yellow oil. LC-MS: m/z 114 [M+H]$^+$.

Intermediate 9

3-(2,2-difluoroethyl)-3,9-diazaspiro[5.5]undecane

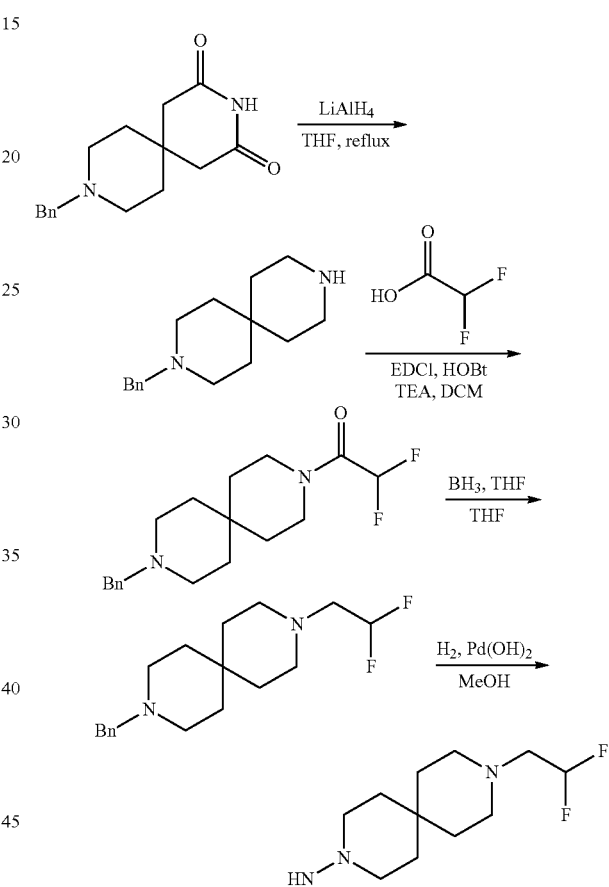

Step 1: 3-benzyl-3,9-diazaspiro[5.5]undecane

To a suspension of LiAlH$_4$ (314 mg, 8.26 mmol) in anhydrous THF (1 mL) was added 9-benzyl-3,9-diazaspiro [5.5]undecane-2,4-dione (750 mg, 2.75 mmol) in portions at −10° C. under a $N_2$ atmosphere. The resulting mixture was stirred at 70° C. overnight. The reaction was quenched by addition of NaSO$_4$.10H$_2$O at 0° C. Ater stirred for 30 min, the mixture was filtered and the filtrate was concentrated under reduced pressure. The residue was diluted with EtAOc and washed with brine, dried over anhydrous $Na_2SO_4$ and concentrated under reduced pressure to give 3-benzyl-3,9-diazaspiro[5.5]undecane (600 mg, 89.2% yield) as a yellow oil, which was directly used to next step without purification. LC-MS m/z: 245 [M+H]$^+$.

Step 2: 1-(9-benzyl-3,9-diazaspiro[5.5]undecan-3-yl)-2,2-difluoroethanone

To a solution of (R)-2-(1-(tert-butoxycarbonyl)pyrrolidin-3-yl)acetic acid (600 mg, 2.46 mmol) in DCM (25 mL) was sequentially added 1-(3-dimethylaminopropyl)-3-ethylcarbodiimide hydrochloride (458 mg, 2.95 mmol) and 1-hydroxybenzotriazole (380 mg, 2.95 mmol), and then DIPEA (1.70 mL, 9.82 mmol) was added drop-wise. The mixture was stirred for 10 min and 2,2-difluoroacetic acid (283 mg, 2.95 mmol) was added. The reaction was stirred at room temperature overnight. The reaction was diluted with DCM (50 mL×2) and washed with water (50 mL), brine (50 mL), dried over $Na_2SO_4$ and concentrated. The residue was purified by silica gel column chromatography (DCM:MeOH=100:1 to 50:1 to give 1-(9-benzyl-3,9-diazaspiro[5.5]undecan-3-yl)-2,2-difluoroethanone (750 mg, 94.8% yield) as a colorless oil. LC-MS m/z: 323 [M+H−56]$^+$.

Step 3: 3-benzyl-9-(2,2-difluoroethyl)-3,9-diazaspiro[5.5]undecane

To a solution of 1-(9-benzyl-3,9-diazaspiro[5.5]undecan-3-yl)-2,2-difluoroethanone (750 mg, 2.33 mmol) in THF (anhydrous, 20 mL) was added a solution of borane-tetrahydrofuran complex (9.31 mL, 9.31 mmol, 1M in THF) dropwise at −10° C. over 30 min. The reaction was stirred at room temperature overnight. After the reaction mixture was cooled to 0° C., MeOH (10 mL) was added drop-wise, and resulting mixture was stirred at room temperature for 30 min. The mixture was then concentrated under vacuum to give a yellow reside, which was dissolved in EtOH/$H_2O$ (9 mL/1 mL) and stirred at reflux overnight. The resulting mixture was concentrated under vacuum. The residue was purified by silica gel column chromatography (petroleum ether:ethyl acetate=5:1) to give 3-benzyl-9-(2,2-difluoroethyl)-3,9-diazaspiro[5.5]undecane (400 mg, 55.8% yield) as a colorless oil. LC-MS m/z: 309 [M+H]$^+$.

Step 4: 3-(2,2-difluoroethyl)-3,9-diazaspiro[5.5]undecane

A solution of 3-benzyl-9-(2,2-difluoroethyl)-3,9-diazaspiro[5.5]undecane (400 mg, 1.3 mmol) in MeOH (10 mL) was degassed three times under $N_2$ atmosphere, Pd(OH)$_2$ (40 mg, 10% wt) and a drop of acetic acid was added. The mixture was degassed again and stirred under $H_2$ atmosphere at room temperature overnight. The reaction was filtered through Celite, and the filtrate was concentrated to give 3-(2,2-difluoroethyl)-3,9-diazaspiro[5.5]undecane (300 mg, crude) as a colorless oil. LC-MS m/z: 219 [M+H]$^+$.

Intermediate 10

2-(2,2-difluoroethyl)-2,6-diazaspiro[3.4]octane

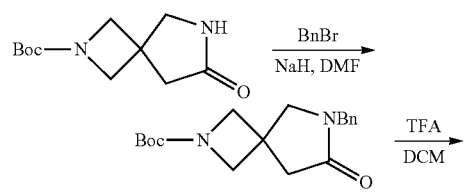

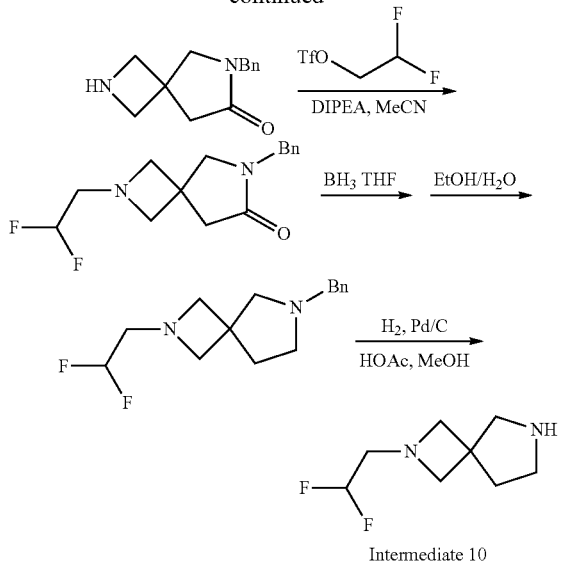

Intermediate 10

Step 1: tert-butyl 6-benzyl-7-oxo-2,6-diazaspiro[3.4]octane-2-carboxylate

To a solution of tert-butyl 7-oxo-2,6-diazaspiro[3.4]octane-2-carboxylate (2.3 g, 10.16 mmol) in DMF (15 mL) was added NaH (813.2 mg, 20.33 mmol, 60% dispersion in mineral oil) in portions at 0° C. After the mixture was stirred at 0° C. for 30 min, benzylbromide (1.45 mL, 12.20 mmol) was added dropwise. The reaction was then stirred at room temperature overnight. The reaction was quenched with ice water and extracted with EtOAc (50 mL×2). The combined organic layers were dried over $Na_2SO_4$, filtered and concentrated. The residue was purified by silica gel column chromatography (petroleum ether:EtOAc=5:1 to 1:2) to give tert-butyl 6-benzyl-7-oxo-2,6-diazaspiro[3.4]octane-2-carboxylate (2.9 g, 90.1% yield) as a colorless oil. LC-MS m/z: 317 [M+H]$^+$.

Step 2: 6-benzyl-2,6-diazaspiro[3.4]octan-7-one

To a mixture of tert-butyl 6-benzyl-7-oxo-2,6-diazaspiro[3.4]octane-2-carboxylate (900 mg, 2.84 mmol) in DCM (2 mL) was added trifluoroacetic acid (2 mL) dropwise at 0° C. The reaction was stirred at room temperature for 1 hr. The mixture was concentrated under reduced pressure to give 6-benzyl-2,6-diazaspiro[3.4]octan-7-one trifluoroacetate (610 mg, 99.1% yield) as a yellow syrup, which was directly used to the next reaction without purification. LC-MS m/z: 217 [M+H]$^+$.

Step 3: 6-benzyl-2-(2,2-difluoroethyl)-2,6-diazaspiro[3.4]octan-7-one

To a solution of 6-benzyl-2,6-diazaspiro[3.4]octan-7-one (900.0 mg, 4.16 mmol) in acetonitrile (10 mL) was added DIPEA (1.21 mL, 7.01 mmol) and 2,2-difluoroethyl trifluoromethanesulfonate (500 mg, 2.34 mmol). The reaction was stirred at room temperature overnight. The mixture was then concentrated and the residue was dissolved in EtOAc (50 mL). The solution was washed with water (50 mL×2), dried and concentrated. The residue was purified by silica gel column chromatography (DCM:MeOH=100:1 to 50:1) to give 6-benzyl-2-(2,2-difluoroethyl)-2,6-diazaspiro[3.4]octan-7-one (600 mg, 91.7% yield) as a brown oil. LC-MS m/z: 281 [M+H]+.

Step 4: 6-benzyl-2-(2,2-difluoroethyl)-2,6-diazaspiro[3.4]octane

To a solution of 6-benzyl-2-(2,2-difluoroethyl)-2,6-diazaspiro[3.4]octan-7-one (600 mg, 2.14 mmol) in dry THF (10 mL) was added a solution of borane-tetrahydrofuran complex (8.56 mL, 8.56 mmol, 1M in THF) dropwise at −10° C. over 10 min. The reaction was stirred at room temperature overnight. The reaction mixture was cooled to 0° C., MeOH (10 mL) was added dropwise, and resulting mixture was stirred at room temperature for 30 min. The mixture was then concentrated and the residue was dissolved in EtOH/water (9 mL/1 mL) and stirred at reflux overnight. The resulting mixture was concentrated under vacuum and the residue was purified by silica gel column chromatography (DCM:MeOH=100:0 to 30:1) to give 6-benzyl-2-(2,2-difluoroethyl)-2,6-diazaspiro[3.4]octane (450 mg, 78.9% yield) as a colorless oil. LC-MS m/z: 267 [M+H]+.

Step 5: 2-(2,2-difluoroethyl)-2,6-diazaspiro[3.4]octane

To a solution of 6-benzyl-2-(2,2-difluoroethyl)-2,6-diazaspiro[3.4]octane (450 mg, 1.69 mmol) in MeOH (10 mL) was added three drops of acetic acid and Pd/C (45 mg, 10% wt). The resulting mixture was degassed and stirred under a H2 atmosphere at room temperature for 5 hrs. The mixture was filtered through a pad of Celite. The filtrate was concentrated under reduced pressure to give 2-(2,2-difluoroethyl)-2,6-diazaspiro[3.4]octane (290 mg, 97.3% yield) as a colorless oil. LC-MS m/z: 177 [M+H]+.

The following intermediate was prepared according to procedures similar to that described for Intermediate 10 by using appropriate starting materials.

| Intermediate # | Structure | LC-MS |
|---|---|---|
| 11 | 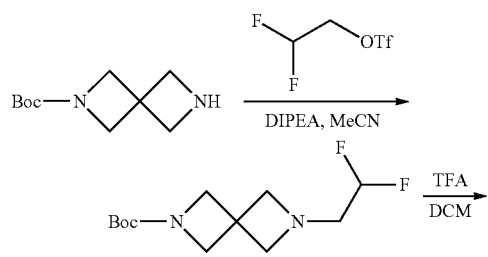 | 205 [M + H]+ |
| 12 | 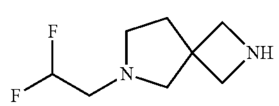 | 177 [M + H]+ |

Intermediate 13

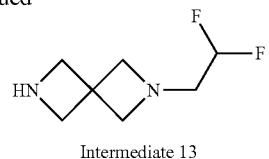

Intermediate 13

Step 1: tert-butyl 6-(2,2-difluoroethyl)-2,6-diazaspiro[3.3]heptane-2-carboxylate To a solution of tert-butyl 2,6-diazaspiro[3.3]heptane-2-carboxylate (400 mg, 2.02 mmol) in MeCN (5 mL) was added DIPEA (782 mg, 6.06 mmol) and 2,2-difluoroethyl trifluoromethanesulfonate (563 mg, 2.63 mmol) at 0° C. The resulting mixture was stirred at room temperature overnight. The mixture was concentrated, and the residue was partitioned between DCM (20 mL) and water (10 mL). The organic layer was dried over anhydrous Na2SO4 and concentrated. The residue was purified by silica gel column chromatography (DCM:MeOH=50:1 to 20:1) to give tert-butyl 6-(2,2-difluoroethyl)-2,6-diazaspiro[3.3]heptane-2-carboxylate (230 mg, 43.9% yield) as a colourless oil. LC-MS m/z: 263 [M+H]+.

Step 2: 2-(2,2-difluoroethyl)-2,6-diazaspiro[3.3]heptane trifluoroacetate

To a solution of tert-butyl 6-(2,2-difluoroethyl)-2,6-diazaspiro[3.3]heptane-2-carboxylate (300 mg 1.14 mmol) in DCM (4 mL) was added TFA (2 mL) dropwise at 0° C. The reaction was then stirred at room temperature for 2 hrs. The resulting mixture was concentrated under vacuum to give a residue, which was co-evaporated with toluene (1 mL×2) to give 2-(2,2-difluoroethyl)-2,6-diazaspiro[3.3]heptane trifluoroacetate (400 mg, 100% yield) as a brown oil, which was directly used to the next reaction without purification. LC-MS m/z: 163 [M+H]+.

Intermediate 14

(1R,5S,6r)-N-methyl-3-azabicyclo[3.1.0]hexane-6-carboxamide

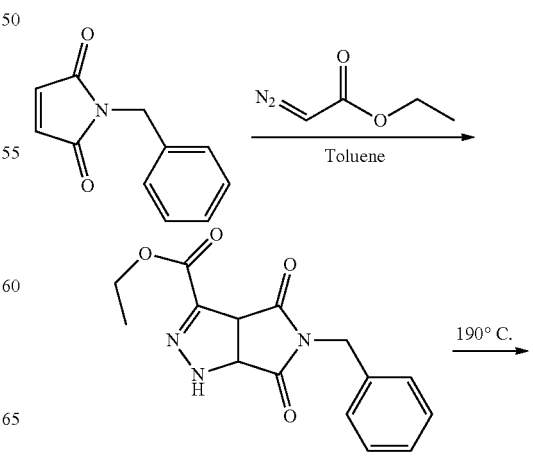

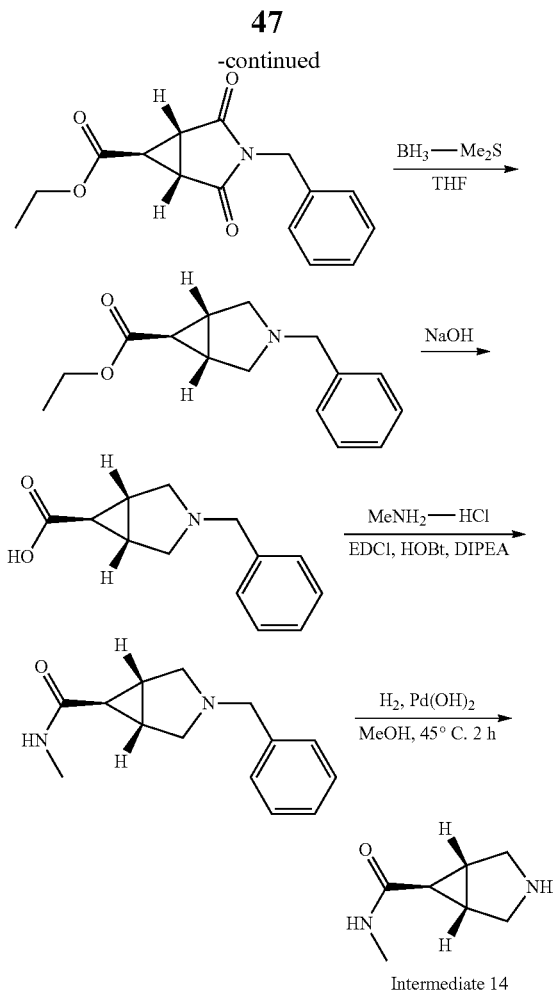

Intermediate 14

Step 1: ethyl 5-benzyl-4,6-dioxo-1,3a,4,5,6,6a-hexahydropyrrolo[3,4-c]pyrazole-3-carboxylate To a solution of 1-benzyl-1H-pyrrole-2,5-dione (15.0 g, 80.13 mmol) in toluene (80 mL) was added ethyl 2-diazoacetate (10.16 g, 80.13 mmol, 90% solution in DCM). The resulting mixture was stirred at 100° C. for 5 hrs. The mixture was concentrated under vacuum to give a yellow reside, which was diluted with EtOAc (100 mL), washed with brine (30 mL×2). The combined aqueous layers were back-extracted with EtOAc (30 mL×2). The combined organic layers was dried over $Na_2SO_4$ and concentrated. The residue was purified by silica gel column chromatography (petroleum ether:ethyl acetate=100:1-20:1) to give the titled compound (15.2 g, 62.96% yield) as a white solid. LC-MS m/z: 302 [M+H]$^+$.

Step 2: (1R,5S,6r)-ethyl 3-benzyl-2,4-dioxo-3-azabicyclo[3.1.0]hexane-6-carboxylate Ethyl 5-benzyl-4,6-dioxo-1,3a,4,5,6,6a-hexahydropyrrolo[3,4-c]pyrazole-3-carboxylate (8 g, 22.56 mmol) was slowly added to a flask which was heated to 190° C. The melted mixture was stirred at this temperature for 1 hour. The mixture was cooled to room temperature and diluted with ether. The solution was cooled in a dry ice acetone bath for about 2 hours. The precipitated solid was collected by filtration and washed small volume of ether to afford the titled compound (4.1 g, 56.5% yield) as a white solid. LC-MS m/z: 302 [M+H]$^+$. $^1$H NMR (400 MHz, CDCl$_3$) δ 7.28-7.19 (m, 5H), 4.44 (s, 2H), 4.11 (q, J=7.1 Hz, 2H), 2.80 (d, J=2.8 Hz, 2H), 2.20 (t, J=2.8 Hz, 1H), 1.17 (dt, J=7.0, 4.8 Hz, 3H).

Step 3: (1R,5S,6r)-ethyl 3-benzyl-3-azabicyclo[3.1.0]hexane-6-carboxylate

To a solution of (1R,5S,6r)-ethyl 3-benzyl-2,4-dioxo-3-azabicyclo[3.1.0]hexane-6-carboxylate (4.0 g, 14.64 mmol) in THF (50 mL) was added BH$_3$-Me$_2$S (2N solution in THF 30 mL, 60 mmol) dropwise at 0° C. over a period of 30 minutes. The resulting mixture was stirred at reflux for 6 hours. The reaction was cooled 0° C., quenched by adding aqueous NH$_4$Cl solution and, extracted with EtOAc. The combined organic layers were dried over anhydrous Na$_2$SO$_4$ and concentrated. The residue was purified by silica gel column chromatography (petroleum ether:ethyl acetate=50:1-10:1) to afford (1R,5S,6r)-ethyl 3-benzyl-3-azabicyclo[3.1.0]hexane-6-carboxylate (2.1 g, 58.5% yield) as a white solid. LC-MS m/z: 246 [M+H]$^+$.

Step 4: (1R,5S,6r)-3-benzyl-3-azabicyclo[3.1.0]hexane-6-carboxylic acid

To a stirred solution of (1R,5S,6r)-ethyl 3-benzyl-3-azabicyclo[3.1.0]hexane-6-carboxylate (2 g, 2.95 mmol) in 1,4-dioxane (10 mL) was added NaOH solution (10 mL, 2 N) in portions at 0° C. The reaction was stirred at room temperature for 16 hrs. The pH was adjusted to around 5 by progressively addition of aqueous 1N HCl solution. The mixture was then concentrated under vacuum to give (1R,5S,6r)-3-benzyl-3-azabicyclo[3.1.0]hexane-6-carboxylic acid (1.6 g, 90.33% yield) as a white solid. LC-MS m/z: 218 [M+H]$^+$.

Step 5: (1R,5S,6r)-3-benzyl-N-methyl-3-azabicyclo[3.1.0]hexane-6-carboxamide

To a stirred solution of (1R,5S,6r)-3-benzyl-3-azabicyclo[3.1.0]hexane-6-carboxylic acid (600 mg, 2.76 mmol) in DCM (10 mL) were sequentially added EDCI (794 mg, 4.14 mmol), HOBt (559 mg, 4.14 mmol), methylamine hydrochloride (373 mg, 5.52 mmol) and DIPEA (1.90 mL, 11.05 mmol). The reaction mixture was stirred at room temperature for 12 hrs, and then diluted with water and extracted with EtOAc. The organic layers were washed with brine, dried over Na$_2$SO$_4$, filtered and concentrated. The residue was purified by silica gel column chromatography (petroleum ether:ethyl acetate=10:1-1:1) to give (1R,5S,6r)-3-benzyl-N-methyl-3-azabicyclo[3.1.0]hexane-6-carboxamide (320 mg, 50.3% yield) as a yellow oil. LC-MS m/z: 231 [M+H]$^+$.

Step 6: (1R,5S,6r)-N-methyl-3-azabicyclo[3.1.0]hexane-6-carboxamide

To a solution of (1R,5S,6r)-3-benzyl-N-methyl-3-azabicyclo[3.1.0]hexane-6-carboxamide (320 mg, 1.39 mmol) in MeOH (10 mL) was added Pd(OH)₂ (390.26 mg, 0.139 mmol, 5% weight). The reaction mixture was stirred under hydrogen atmosphere at 45° C. for 2 hrs. The reaction mixture was filtered through a short pad of Celite and the filtrate was concentrated to afford (1R,5S,6r)-N-methyl-3-azabicyclo[3.1.0]hexane-6-carboxamide (190 mg 97.5% yield) as a yellow oil. LC-MS m/z: 141 [M+H]⁺.

The following intermediate was prepared according to procedures similar to that described for Intermediate 14 by using corresponding amines as starting materials.

| Intermediate # | Structure | LC-MS |
|---|---|---|
| 15 | 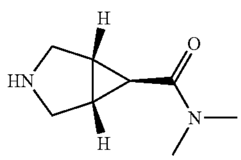 | 155 [M + H]+ |
| 16 | 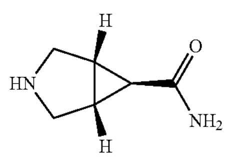 | 127 [M + H]⁺ |
| 17 | 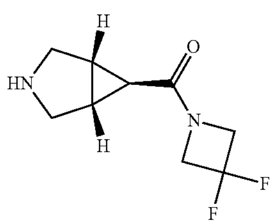 [SMILES: O=C([C@H]1[C@@H]2CNC[C@@H]21)N1CC(F)(F)C1] | 203 [M + H]⁺ |
| 18 | 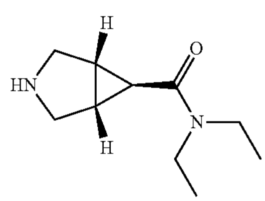 | 183 [M + H]⁺ |
| 19 | 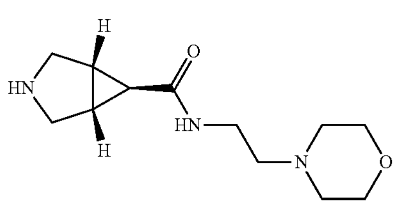 [SMILES: O=C(NCCN1CCOCC1)[C@H]1[C@@H]2CNC[C@@H]21] | 240 [M + H]⁺ |
| 20 | 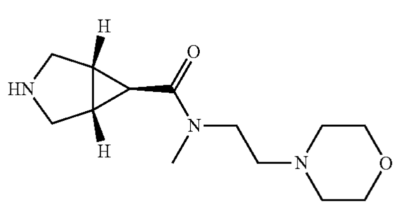 [SMILES: CN(CCN1CCOCC1)C(=O)[C@H]1[C@@H]2CNC[C@@H]21] | 254 [M + H]⁺ |

Intermediate 21

(1R,5S,6r)-6-((3,3-difluoroazetidin-1-yl)methyl)-3-azabicyclo[3.1.0]hexane

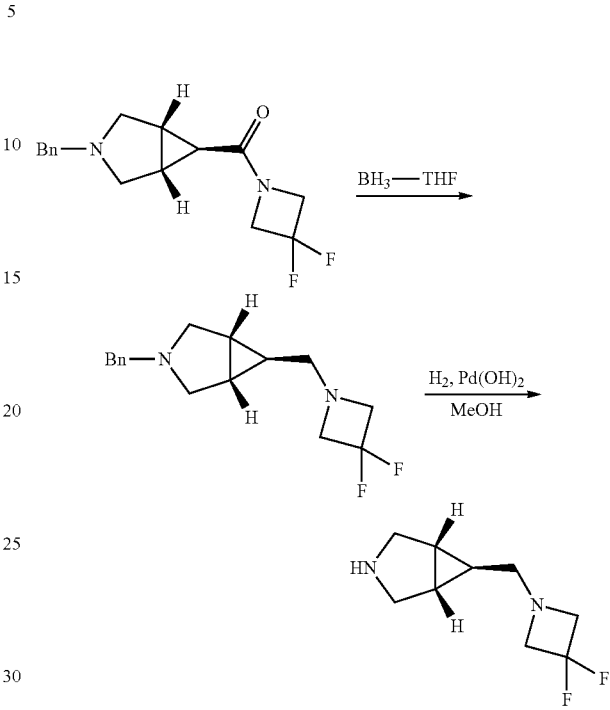

Intermediate 21

Step 1: ((1R,5S,6r)-3-benzyl-6-((3,3-difluoroazetidin-1-yl)methyl)-3-azabicyclo[3.1.0]hexane To a solution of ((1R,5S,6r)-3-benzyl-3-azabicyclo[3.1.0]hexan-6-yl)(3,3-difluoroazetidin-1-yl)methanone (610 mg, 2.0 mmol) in dry THF (10 mL) was added a solution of BH₃-THF (6 mL, 5.0 mmol, 1 M in THF) dropwise at −10° C. The resulting mixture was stirred at r.t. overnight. After it was cooled to 0-5° C., MeOH was added dropwise below 10° C., and the resulting mixture was stirred at r.t for 30 min. The mixture was concentrated under vacuum, and the residue was dissolved in EtOH/H₂O (8 mL/1 mL) and stirred at reflux overnight. The resulting mixture was concentrated under vacuum and the residue was purified by silica gel column chromatography (DCM:MeOH=150:0 to 50:1) to give ((1R,5S,6r)-3-benzyl-6-((3,3-difluoroazetidin-1-yl)methyl)-3-azabicyclo[3.1.0]hexane (420 mg, 73.1% yield) as a colorless oil. LC-MS m/z: 279 [M+H]⁺.

Step 2: (1R,5S,6r)-6-((3,3-difluoroazetidin-1-yl)methyl)-3-azabicyclo[3.1.0]hexane To a stirred solution of ((1R,5S,6r)-3-benzyl-6-((3,3-difluoroazetidin-1-yl)methyl)-3-azabicyclo[3.1.0]hexane (300 mg, 1.1 mmol) in MeOH (10 mL) was added Pd(OH)₂ on carbon (50 mg, 10% wt). The reaction mixture was degassed and stirred under a H₂ atmosphere at 45° C. for 2 hrs. The reaction mixture was cooled and and filtered through a small pad of Celite. The filtrate was concentrated under reduced pressure to give (1R,5S,6r)-6-((3,3-difluoroazetidin-1-yl)methyl)-3-azabicyclo[3.1.0]hexane (210 mg, 98.6% yield) as a yellow solid. LC-MS m/z: 189 [M+H]⁺.

The following intermediate was prepared according to procedures similar to that described for Intermediate 21 by using appropriate starting material.

| Intermediate # | Structure | LC-MS |
|---|---|---|
| 22 | 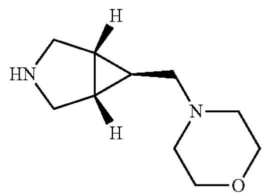 [SMILES: C1CN(C[C@H]2[C@@H]3CNC[C@@H]32)CCO1] | 183 [M + H]+ |
| 23 | 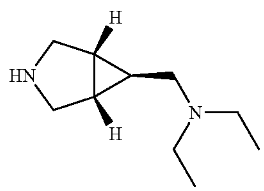 | 169 [M + H]+ |

Intermediate 24

(3aR,6aS)-methyl hexahydropyrrolo[3,4-c]pyrrole-2(1H)-carboxylate

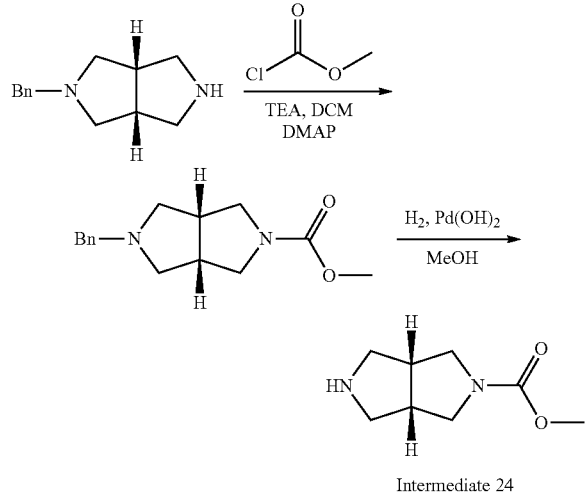

Intermediate 24

Step 1: (3aR,6aS)-methyl 5-benzylhexahydropyrrolo[3,4-c]pyrrole-2(1H)-carboxylate To a solution of (3aR,6aS)-2-benzyloctahydropyrrolo[3,4-c]pyrrole (500 mg, 2.5 mmol) in dry DCM (8 mL) was added TEA (0.9 mL, 7.5 mmol) and methyl chloroformate (310 mg, 2.75 mmol) at 0° C. After the resulting mixture was stirred at room temperature overnight, it was partitioned between buffer (pH 4.0, 20 mL) and DCM. The organic layer was dried over anhydrous $Na_2SO_4$, and concentrated. The residue was purified by silica gel column chromatography (DCM:MeOH=200:1) to give (3aR,6aS)-methyl 5-benzylhexahydropyrrolo[3,4-c]pyrrole-2(1H)-carboxylate (210 mg, 32.3% yield) as a colorless oil. LC-MS m/z: 261 [M+H]+.

Step 2: (3aR,6aS)-methyl hexahydropyrrolo[3,4-c]pyrrole-2(1H)-carboxylate

To a solution of (3aR,6aS)-methyl hexahydropyrrolo[3,4-c]pyrrole-2(1H)-carboxylate (210 mg, crude) in MeOH (5 mL) was added $Pd(OH)_2$ on carbon (50 mg, 10% wt) and a drop of HOAc. The mixture was degassed and stirred under a $H_2$ atmosphere at 45° C. overnight. The reaction mixture was filtered through a pad of Celite, and the filtrate was concentrated to give (3aR,6aS)-methyl hexahydropyrrolo[3,4-c]pyrrole-2(1H)-carboxylate (180 mg, 100% yield) as a light brown oil. LC-MS m/z: 171 [M+H]+.

Intermediate 25

(3aR,6aS)—N,N-dimethylhexahydropyrrolo[3,4-c]pyrrole-2(1H)-carboxamide

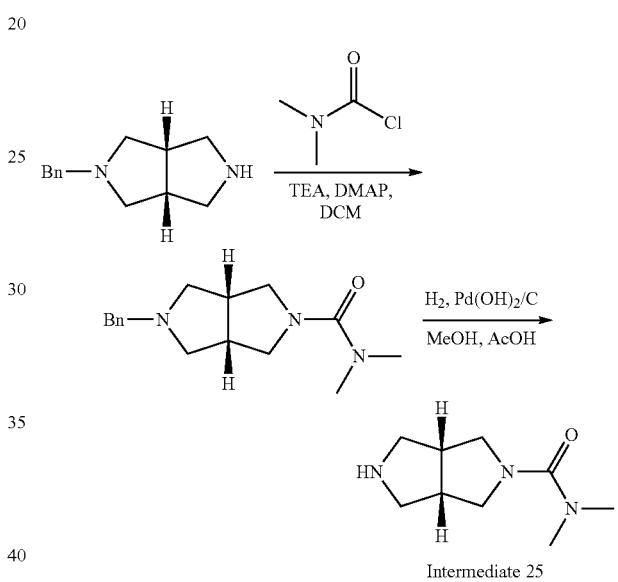

Intermediate 25

Step 1: (3aR,6aS)-5-benzyl-N,N-dimethylhexahydropyrrolo[3,4-c]pyrrole-2(1H)-carboxamide To a mixture of (3aR,6aS)-2-benzyloctahydropyrrolo[3,4-c]pyrrole (500 mg, 2.47 mmol) in dry DCM (5 mL) was added DMAP (30 mg, 0.24 mmol), TEA (623 mg, 6.17 mmol) and dimethylcarbamic chloride (317 mg, 2.96 mmol) at 0° C. The resulting mixture was stirred at room temperature overnight and concentrated. The residue was partitioned between EtOAc (20 mL) and water (10 mL). The organic layer was washed with water, dried over anhydrous $Na_2SO_4$, and concentrated. The residue was purified by silica gel column chromatography (DCM:MeOH=50:1) to give (3aR,6aS)-5-benzyl-N,N-dimethylhexahydropyrrolo[3,4-c]pyrrole-2(1H)-carboxamide (660 mg, 97.9% yield) as a colourless oil. LC-MS m/z: 274 [M+H]+.

Step 2: (3aR,6aS)—N,N-dimethylhexahydropyrrolo[3,4-c]pyrrole-2(1H)-carboxamide To a solution of (3aR,6aS)-5-benzyl-N,N-dimethylhexahydropyrrolo[3,4-c]pyrrole-2(1H)-carboxamide (500 mg 1.83 mmol) in MeOH (5 mL) was added a drop of AcOH and $Pd(OH)_2$ on carbon (50 mg, 10% wt) at 0° C. The reaction was degassed and stirred under a H₂ atmosphere at 45° C. overnight. The reaction mixture was cooled and filtered through a pad of Celite. The filtrate was concentrated to give (3aR,6aS)—N,N-dimethylhexahydropyrrolo[3,4-c]pyrrole-2(1H)-carboxamide (380 mg, 100% yield) as a colourless oil, which was directly used to the next reaction without purification. LC-MS m/z: 184 [M+H]⁺.

Intermediate 26

(3aR,6aS)—N-ethylhexahydropyrrolo[3,4-c]pyrrole-2(1H)-carboxamide

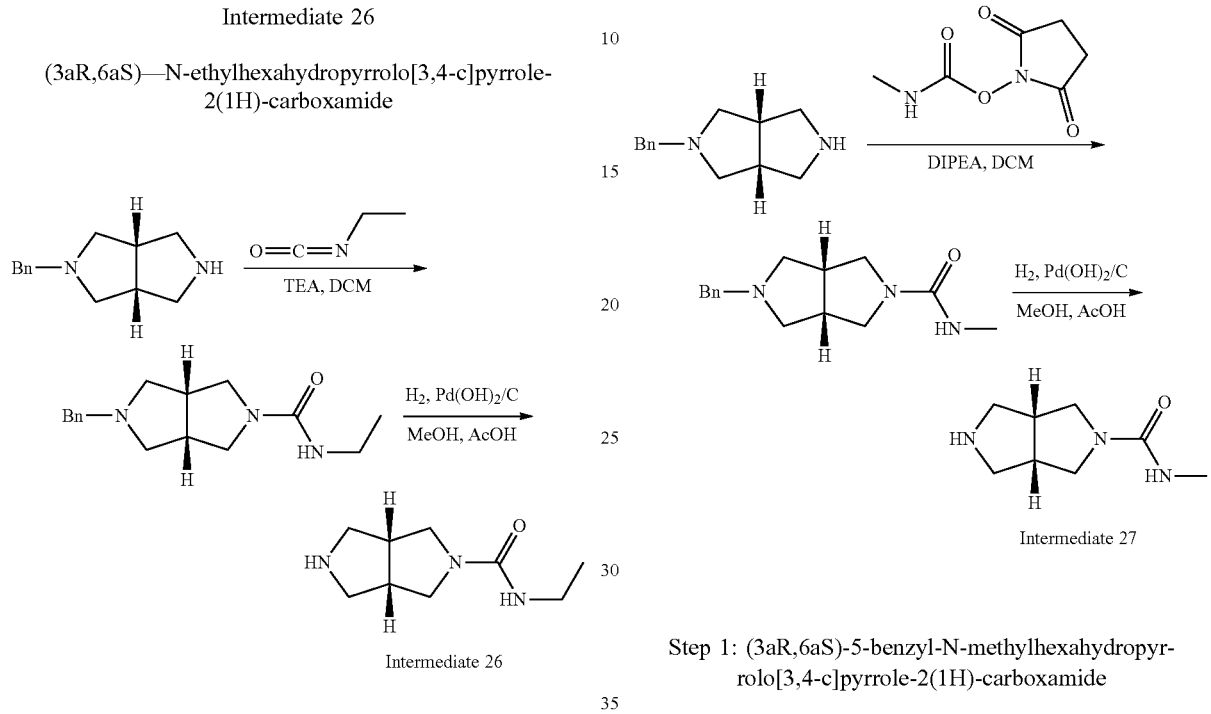

Intermediate 26

Step 1: (3aR,6aS)-5-benzyl-N-ethylhexahydropyrrolo[3,4-c]pyrrole-2(1H)-carboxamide To a solution of (3aR,6aS)-2-benzyloctahydropyrrolo[3,4-c]pyrrole (500 mg, 2.47 mmol) in DCM (5 mL) was added TEA (275 mg, 2.72 mmol) and ethyl isocyanate (184 mg, 2.59 mmol) at 0° C. The resulting mixture was stirred at room temperature overnight. The mixture was concentrated, and the residue was partitioned between EtOAc (20 mL) and water (10 mL). The organic layer was dried over anhydrous Na₂SO₄ and concentrated. The residue was purified by silica gel column chromatography (DCM:MeOH=50:1) to give (3aR,6aS)-5-benzyl-N-ethylhexahydropyrrolo[3,4-c]pyrrole-2(1H)-carboxamide (430 mg, 63.8% yield) as a colourless oil. LC-MS m/z: 274 [M+H]⁺.

Step 2: (3aR,6aS)—N-ethylhexahydropyrrolo[3,4-c]pyrrole-2(1H)-carboxamide

To a solution of (3aR,6aS)-5-benzyl-N-ethylhexahydropyrrolo[3,4-c]pyrrole-2(1H)-carboxamide (430 mg 1.57 mmol) in MeOH (5 mL) was added a drop of AcOH and Pd(OH)₂/C (43 mg, 10% wt) at 0° C. The reaction mixture was degassed and stirred under a H₂ atmosphere at 45° C. overnight. The resulting mixture was cooled and filtered through a pad of Celite. The filtrate was concentrated to give (3aR,6aS)—N-ethylhexahydropyrrolo[3,4-c]pyrrole-2(1H)-carboxamide (280 mg, 100% yield) as a colourless oil, which was directly used to the next reaction without purification. LC-MS m/z: 184 [M+H]⁺.

Intermediate 27

(3aR,6aS)—N-methylhexahydropyrrolo[3,4-c]pyrrole-2(1H)-carboxamide

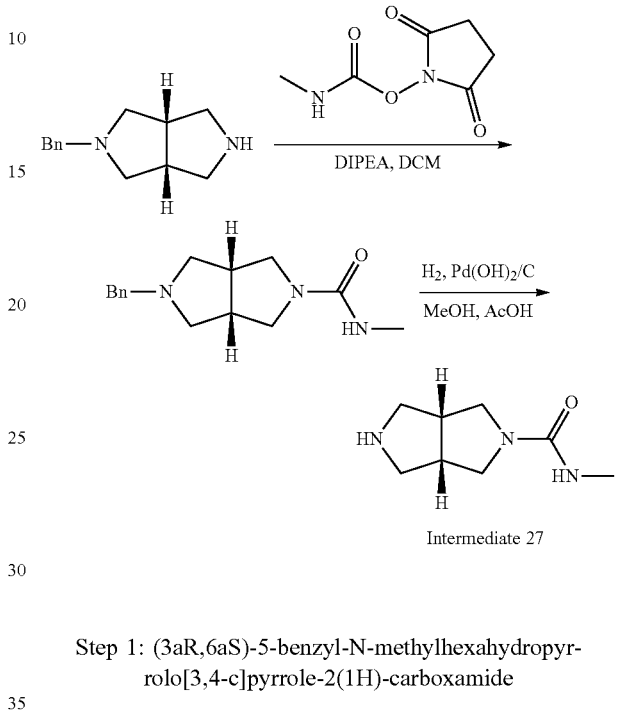

Intermediate 27

Step 1: (3aR,6aS)-5-benzyl-N-methylhexahydropyrrolo[3,4-c]pyrrole-2(1H)-carboxamide To a solution of (3aR,6aS)-2-benzyloctahydropyrrolo[3,4-c]pyrrole (500 mg, 2.47 mmol) in anhydrous DCM (5 mL) was added DIPEA (637 mg, 4.94 mmol) and 2,5-dioxopyrrolidin-1-yl methylcarbamate (850 mg, 494 mmol) at 0° C. The resulting mixture was stirred at room temperature overnight. The mixture was concentrated, and residue was partitioned between EtOAc (20 mL) and water (10 mL). The organic layer was washed with water (10 mL), dried over anhydrous Na₂SO₄ and concentrated. The residue was purified by silica gel column chromatography (DCM: MeOH=50:1) to give (3aR,6aS)-5-benzyl-N-methylhexahydropyrrolo[3,4-c]pyrrole-2(1H)-carboxamide (300 mg, 46.9% yield) as a colourless oil. LC-MS m/z: 260 [M+H]⁺.

Step 2: (3aR,6aS)—N-methylhexahydropyrrolo[3,4-c]pyrrole-2(1H)-carboxamide

To a solution of (3aR,6aS)-5-benzyl-N-methylhexahydropyrrolo[3,4-c]pyrrole-2(1H)-carboxamide (300 mg 1.16 mmol) in MeOH (5 mL) was added a drop of AcOH and Pd(OH)₂ on carbon (30 mg, 10% wt) at 0° C. The reaction was degassed and stirred under a H₂ atmosphere at 45° C. overnight. The resulting mixture was cooled and filtered through a pad of Celite. The filtrate was concentrated in vacuo to give (3aR,6aS)—N-methylhexahydropyrrolo[3,4-c]pyrrole-2(1H)-carboxamide (200 mg, 100% yield) as a colourless oil, which was directly used to the next reaction without purification. LC-MS m/z: 160 [M+H]⁺.

Intermediate 28

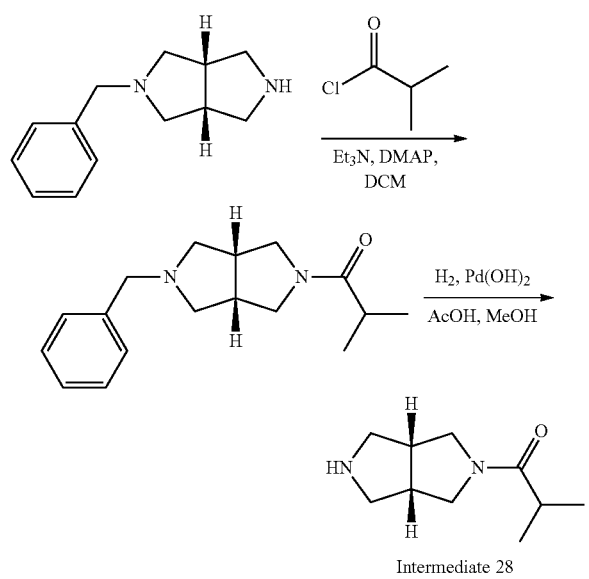

Step 1: 1-((3aR,6aS)-5-benzylhexahydropyrrolo[3,4-c]pyrrol-2(1H)-yl)-2-methylpropan-1-one To a solution of (3aR,6aS)-2-benzyloctahydropyrrolo[3,4-c]pyrrole (500 mg, 2.47 mmol) in anhydrous DCM (20 mL) was added TEA (0.86 mL, 6.18 mmol) and DMAP (50 mg) at 0° C. The mixture was stirred at 0° C. for 10 min and isobutyryl chloride (0.3 mL, 0.97 mmol) were added. After addition, the mixture was stirred at room temperature overnight. The reaction mixture was diluted with NH$_4$OAc buffer (pH 4.0, 20 mL) and extracted with DCM (20 mL×3). The combined organic layers were dried over anhydrous Na$_2$SO$_4$ and concentrated. The residue was purified by silica gel column chromatography (DCM:MeOH=100:1) to give 1-((3aR,6aS)-5-benzylhexahydropyrrolo[3,4-c]pyrrol-2(1H)-yl)-2-methylpropan-1-one (450 mg, 66.8% yield) as a colorless oil. LC-MS m/z: 273 [M+H]$^+$.

Step 2: 1-((3aR,6aS)-hexahydropyrrolo[3,4-c]pyrrol-2(1H)-yl)-2-methylpropan-1-one To a solution of 1-((3aR,6aS)-5-benzylhexahydropyrrolo[3,4-c]pyrrol-2(1H)-yl)-2-methylpropan-1-one (450 mg, 1.65 mmol) in MeOH (10 mL) was added Pd(OH)$_2$ on carbon (50 mg, 10% wt) and a drop of HOAc. The mixture was degassed and stirred under a H$_2$ atmosphere at 45° C. overnight. The reaction was filtered through a pad of Celite, and the filtrate was concentrated to give 1-((3aR,6aS)-hexahydropyrrolo[3,4-c]pyrrol-2(1H)-yl)-2-methylpropan-1-one (250 mg, 83.0% yield) as a light brown oil. LC-MS m/z: 183 [M+H]$^+$.

The following intermediate was prepared according to procedures similar to that described for Intermediate 28 by using appropriate starting material.

| Intermediate # | Structure | LC-MS |
|---|---|---|
| 29 | 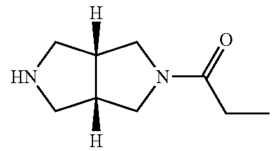 | 169 [M + H]$^+$ |

Intermediate 30

N,N-diethyl-2-((3aR,6aS)-hexahydropyrrolo[3,4-c]pyrrol-2(1H)-yl)acetamide

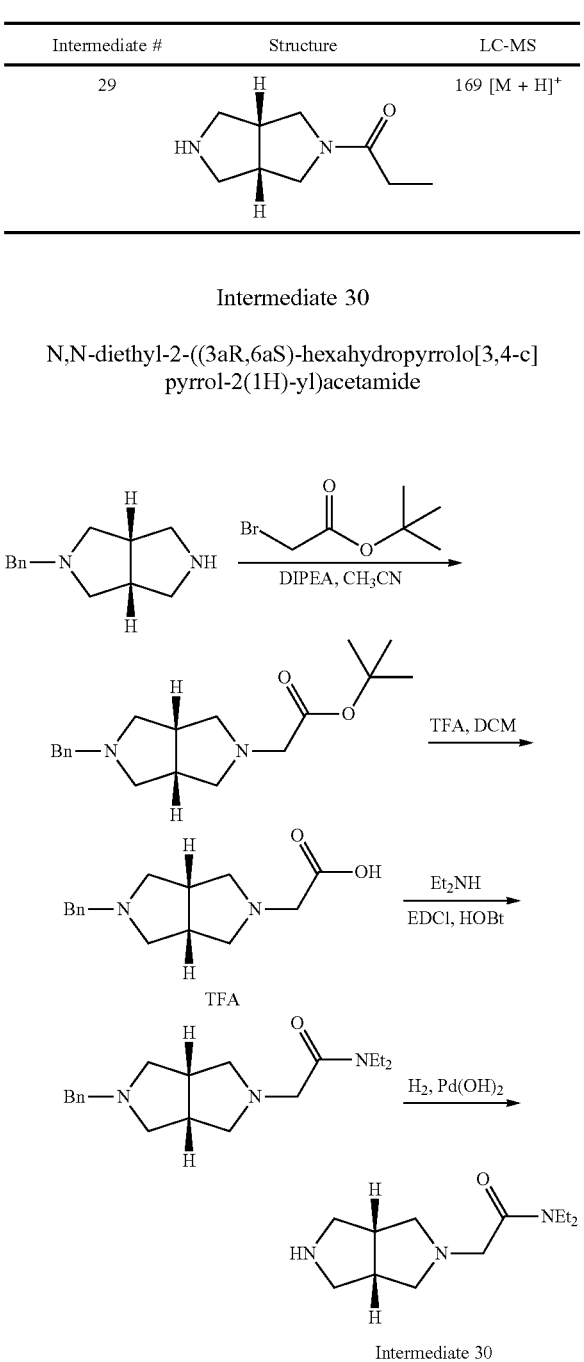

Step 1: (3aR,6aS)-methyl 5-benzylhexahydropyrrolo[3,4-c]pyrrole-2(1H)-carboxylate To a solution of (3aR,6aS)-2-benzyloctahydropyrrolo[3,4-c]pyrrole (1.2 g, 6.0 mmol) in acetonitrile (10 mL) was added DIPEA (3.1 mL, 18.0 mmol) and tert-butyl 2-bromoacetate (1.8 g 9.0 mmol) at 0° C. After addition, the mixture was stirred at room temperature overnight. The reaction mixture was concentrated and the residue was partitioned between DCM (50 mL) and water (15 mL). The organic layer was dried over Na$_2$SO$_4$, filtered, and concentrated. The residue was purified by silica gel column chromatography (DCM:MeOH=50:1 to give (3aR,6aS)-methyl 5-benzylhexahydropyrrolo[3,4-c]pyrrole-2(1H)-carboxylate (1.15 g, 57.1% yield) as a colorless oil. LC-MS m/z: 371 [M+H]+.

Step 2: tert-butyl 2-((3aR,6aS)-5-benzylhexahydropyrrolo[3,4-c]pyrrol-2(1H)-yl)acetic acid trifluoroacetate To a solution of (3aR,6aS)-methyl 5-benzylhexahydropyrrolo[3,4-c]pyrrole-2(1H)-carboxylate (1.15 g, 3.1 mmol) in DCM (8 mL) was added TFA (2 mL) dropwise at 0° C. The reaction was then stirred at rt overnight. The reaction mixture was concentrated to give 2-((3aR,6aS)-5-benzylhexahydropyrrolo[3,4-c]pyrrol-2(1H)-yl)acetic acid trifluoroacetate (2.7 g, 100% yield) as a yellow oil. LC-MS m/z: 261 [M+H]+.

Step 3: 2-((3aR,6aS)-5-benzylhexahydropyrrolo[3,4-c]pyrrol-2(1H)-yl)-N,N-diethylacetamide To a solution of 2-((3aR,6aS)-5-benzylhexahydropyrrolo[3,4-c]pyrrol-2(1H)-yl)acetic acid (1.3 g, 1.5 mmol) in DCM (10 mL) was added EDCI (520 mg 2.7 mmol) and HOBt (300 mg 2.2 mmol), diethylamine (401 mg, 5.4 mmol) and DIPEA (2.1 mL, 11.2 mmol). The resulting mixture was stirred at room temperature for 12 hrs, and then diluted with water and extracted with EtOAc. The organic layer was washed with brine, dried over Na2SO4, filtered and concentrated in vacuo. The residue was purified by silica gel column chromatography (DCM:MeOH=50:1) to give 2-((3aR,6aS)-5-benzylhexahydropyrrolo[3,4-c]pyrrol-2(1H)-yl)-N,N-diethylacetamide (420 mg, 88.7% yield) as a yellow oil. LC-MS m/z: 316 [M+H]+.

Step 4: N,N-diethyl-2-((3aR,6aS)-hexahydropyrrolo[3,4-c]pyrrol-2(1H)-yl)acetamide To a solution of 2-((3aR,6aS)-5-benzylhexahydropyrrolo[3,4-c]pyrrol-2(1H)-yl)-N,N-diethylacetamide (420 mg, 1.33 mmol) in MeOH (5 mL) was added Pd(OH)2 on carbon (50 mg, 10% wt.) and a drop of HOAc. The mixture was degassed and stirred under a H2 atmosphere at 45° C. overnight. The reaction was filtered through a pad of Celite, and the filtrate was concentrated to give N,N-diethyl-2-((3aR,6aS)-hexahydropyrrolo[3,4-c]pyrrol-2(1H)-yl)acetamide (280 mg, 93.3% yield) as a brown oil. LC-MS m/z: 226 [M+H]+.

The following intermediate was prepared according to procedures similar to that described for Intermediate 30 by using appropriate starting material.

| Intermediate # | Structure | LC-MS |
|---|---|---|
| 31 | 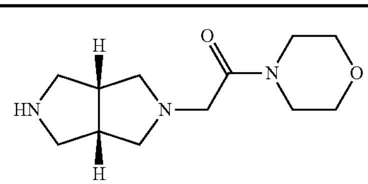 | 240 [M + H]+ |

Intermediate 32

(1R,5S,6r)-3-azabicyclo[3.1.0]hexan-6-ylmethyl methylcarbamate

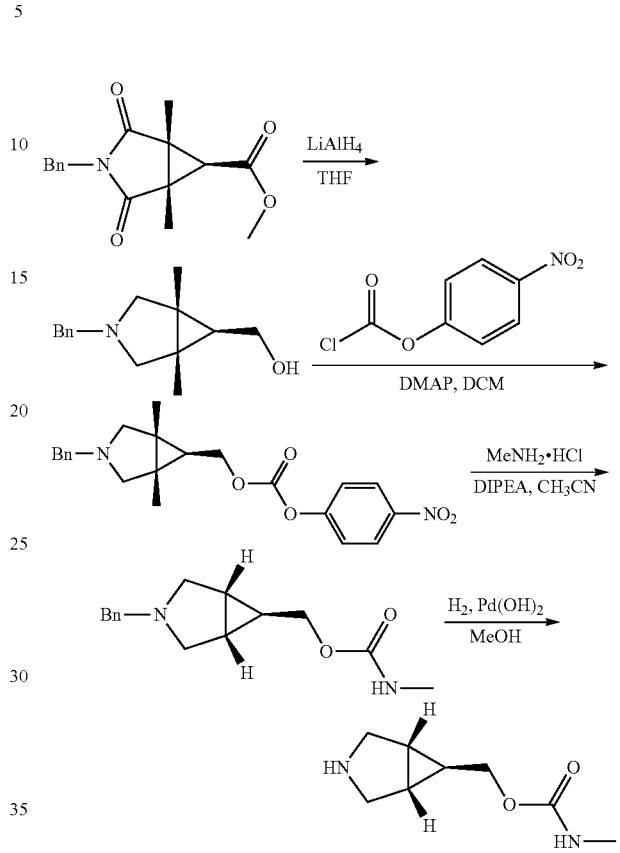

Intermediate 32

Step 1: ((1R,5S,6r)-3-benzyl-3-azabicyclo[3.1.0]hexan-6-yl)methanol

To a solution of (1R,5S,6r)-methyl 3-benzyl-2,4-dioxo-3-azabicyclo[3.1.0]hexane-6-carboxylate (1 g, 3.66 mmol) in dry THF (10 mL) was added LiAlH4 (695 mg, 18.3 mmol) in portions at 0° C., and the reaction was stirred to 50° C. overnight. The mixture was cooled and carefully quenched with water (0.7 mL), aqueous NaOH solution (0.7 mL, 15% wt) followed by water (2.1 mL). The slurry was filtered, and the filter cake was washed with EtOAc. The filtrate was extracted with EtOAc (20 mL×2) and the combined organic layers were dried over anhydrous Na2SO4 and concentrated to give ((1R,5S,6r)-3-benzyl-3-azabicyclo[3.1.0]hexan-6-yl)methanol (750 mg, 96.1% yield) as a yellow oil. LC-MS m/z: 204 [M+H]+.

Step 2: ((1R,5S,6r)-3-benzyl-3-azabicyclo[3.1.0]hexan-6-yl)methyl 4-nitrophenyl carbonate To a solution of ((1R,5S,6r)-3-benzyl-3-azabicyclo[3.1.0]hexan-6-yl)methanol (800 mg, 3.94 mmol) and DMAP (961 mg, 7.88 mmol) in anhydrous DCM (10 mL) was added a solution of p-nitrophenyl chloroformate (1.34 g, 6.69 mmol) in DCM (5 mL) dropwise over 30 min at 0° C. After addition, the mixture was stirred at room temperature for 16 hrs. The mixture was diluted with DCM (10 mL), washed sequentially with 10% aqueous citric acid solution, saturated aqueous K₂CO₃ solution and brine. The organic layer was dried over anhydrous Na₂SO₄ and concentrated and the residue was purified by silica gel column chromatography (DCM:MeOH=80:1) to give the titled product (800 mg, 55.1% yield) as a yellow oil. LC-MS m/z: 368 [M+H]⁺.

Step 3: ((1R,5S,6r)-3-benzyl-3-azabicyclo[3.1.0]hexan-6-yl)methyl methylcarbamate To a mixture methylamine hydrochloride (200 mg, 3.0 mmol) in MeCN (20 mL) and DIPEA (1 mL, 6 mmol) was added ((1R,5S,6r)-3-benzyl-3-azabicyclo[3.1.0]hexan-6-yl)methyl 4-nitrophenyl carbonate (800 mg, 2.17 mmol) in portions at 0° C. After the reaction was stirred at rt overnight, the mixture was concentrated. The residue was dissolved in DCM (20 mL) and washed with ammonium acetate buffer (pH~4, 15 mL×2). The organic layer was washed with aq. NaHCO₃ solution (15 mL×2, 5% wt), dried over Na₂SO₄ and concentrated. The residue was purified via silica gel column chromatography (petroleum ether:ethyl acetate=3:1) to give the titled product (300 mg, 53.1% yield) as a colorless oil. LC-MS m/z: 261[M+H]⁺.

Step 4: (1R,5S,6r)-3-azabicyclo[3.1.0]hexan-6-ylmethyl methylcarbamate

To a solution of ((1R,5S,6r)-3-benzyl-3-azabicyclo[3.1.0]hexan-6-yl)methyl dimethylcarbamate (300 mg, 1.15 mmol) in MeOH (6 mL) was added Pd(OH)₂ (45 mg, 10% wt) and a drop of HOAc. The mixture was degassed and stirred under a H₂ atmosphere at 45° C. for 2 hrs. The reaction was filtered through a pad of Celite, and the filtrate was concentrated to give (1R,5S,6r)-3-azabicyclo[3.1.0]hexan-6-ylmethyl methylcarbamate (190 mg, 96.6% yield) as a light yellow oil. LC-MS m/z: 171 [M+H]⁺.

The following intermediate was prepared according to procedures similar to that described for Intermediate 32 by using appropriate starting material.

| Intermediate # | Structure | LC-MS |
|---|---|---|
| 33 | 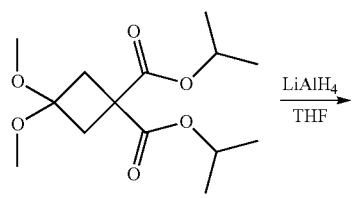 | 185 [M + H]⁺ |

Intermediate 34

4-(2-azaspiro[3.3]heptan-6-ylmethyl)morpholine trifluoroacetate

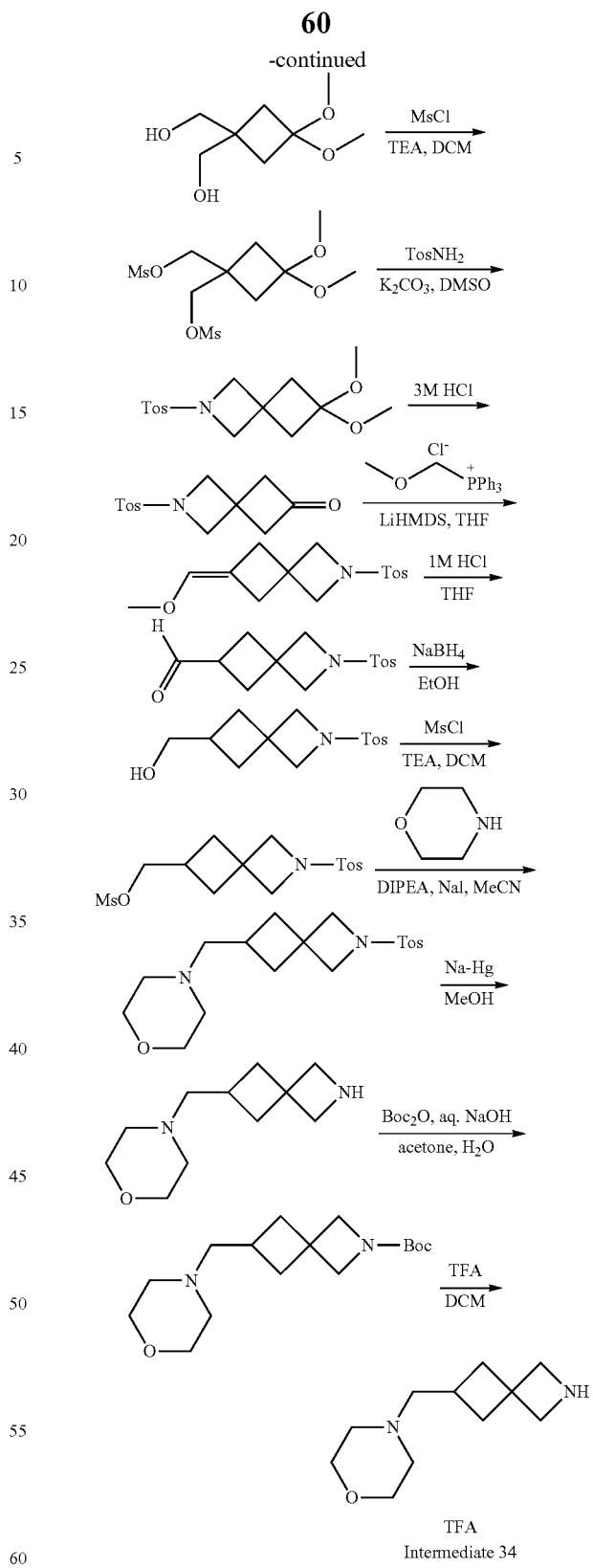

Step 1: (3,3-dimethoxycyclobutane-1,1-diyl)dimethanol

To a suspension of LiAlH₄ (7.16 g, 188.65 mmol) in dry THF (70 mL) was added a solution of diisopropyl 3,3- dimethoxycyclobutane-1,1-dicarboxylate (17.0 g, 58.95 mmol) in THF (80 mL) dropwise at 0° C. The mixture was stirred at room temperature overnight. The reaction was quenched by addition of water (7.16 mL), aqueous sodium hydroxide solution (7.16 mL, 15% wt) and water (21.48 mL). The mixture was stirred at room temperature for 15 min and filtered. The filter cake was then washed with EtOAc (100 mL×2). The combined filtrates were dried over $Na_2SO_4$ and concentrated. The residue was purified by silica gel column chromatography (petroleum ether:EtOAc=5:1 to 1:3) to give (3,3-dimethoxycyclobutane-1,1-diyl)dimethanol (7.3 g, 70.2% yield) as a white solid. $^1$H NMR (400 MHz, $CDCl_3$) δ 3.79 (m, 2H), 3.68 (m, 2H), 3.50 (s, 6H), 3.15 (s, 1H), 2.89 (s, 1H), 2.10 (m, 2H), 1.91 (m, 2H).

Step 2: (3,3-dimethoxycyclobutane-1,1-diyl)bis(methylene) dimethanesulfonate

To a solution of (3,3-dimethoxycyclobutane-1,1-diyl)dimethanol (7.3 g, 41.43 mmol) in DCM (70 mL) was added TEA (34.55 mL, 248.57 mmol) and methanesulfonyl chloride (9.62 mL, 124.28 mmol) dropwise at 0° C. The reaction was stirred at room temperature for 2 hrs. The mixture was diluted with DCM and washed with water. The organic layer was dried over $Na_2SO_4$, filtered and concentrated. The residue was purified by silica gel column chromatography (petroleum ether:EtOAc=10:1 to 1:1) to give (3,3-dimethoxycyclobutane-1,1-diyl)bis(methylene) dimethanesulfonate (11.9 g, 86.4% yield) as a yellow solid. $^1$H NMR (400 MHz, $CDCl_3$) δ 4.22 (s, 4H), 3.08 (s, 6H), 2.98 (s, 6H), 2.04 (s, 4H).

Step 3: 6,6-dimethoxy-2-tosyl-2-azaspiro[3.3]heptane

To a solution of (3,3-dimethoxycyclobutane-1,1-diyl)bis(methylene) dimethanesulfonate (5 g, 15.04 mmol) in DMSO (50 mL) was added solid $K_2CO_3$ (10.40 g, 75.21 mmol) and 4-methylbenzenesulfonamide(2.83 g, 16.55 mmol). The reaction was then stirred at at 85° C. overnight. The mixture was diluted with EtOAc (100 mL), washed with water. The organic layer was dried over $Na_2SO_4$, filtered and concentrated. The residue was purified by silica gel column chromatography (petroleum ether:EtOAc=10:1 to 2:1) to give 6,6-dimethoxy-2-tosyl-2-azaspiro[3.3]heptane (4.2 g, 89.6% yield) as a white solid. LC-MS m/z: 312 $[M+H]^+$.

Step 4: 2-tosyl-2-azaspiro[3.3]heptan-6-one

To a mixture of 6,6-dimethoxy-2-tosyl-2-azaspiro[3.3] heptane (4.0 g, 12.85 mmol) in aqueous HCl solution (60 mL, 3M) was stirred at room temperature overnight. The mixture was concentrated to give 2-tosyl-2-azaspiro[3.3] heptan-6-one (3.1 g, 90.9% yield) as a white solid. LC-MS m/z: 266 $[M+H]^+$.

Step 5: 6-(methoxymethylene)-2-tosyl-2-azaspiro [3.3]heptane

To a solution of (methoxymethyl)triphenylphosphonium (3.88 g, 11.31 mmol) in dry THF (40 mL) was added LiHMDS (9.05 mL, 9.05 mmol) at −10° C. The resulting mixture was stirred at this temperature for 1 hr. Then a solution of 2-tosyl-2-azaspiro[3.3]heptan-6-one (2.0 g, 7.54 mmol) in THF (anhydrous, 20 mL) was added dropwise. The reaction was stirred at room temperature for 4 hrs. The mixture was then cooled to 0° C., quenched with water, extracted with EtOAc (50 mL) The organic layer was dried over $Na_2SO_4$ and concentrated. The residue was purified by silica gel column chromatography (petroleum ether: EtOAc=10:1 to 2:1) to give 6-(methoxymethylene)-2-tosyl-2-azaspiro[3.3]heptane (950 mg, 42.9% yield) as a white solid. LC-MS m/z: 296 $[M+H]^+$.

Step 6: 2-tosyl-2-azaspiro[3.3]heptane-6-carbaldehyde

To a solution of 6-(methoxymethylene)-2-tosyl-2-azaspiro[3.3]heptane (920 mg, 3.14 mmol) in THF (10 mL) was added aqueous HCl (10 mL, 1M). The reaction was stirred at room temperature for 4 hrs. The mixture was diluted with DCM (50 mL), washed with water (50 mL). The organic layer was dried over $Na_2SO_4$ and concentrated to give 2-tosyl-2-azaspiro[3.3]heptane-6-carbaldehyde (850 mg, 97.0% yield) as a white solid. LC-MS m/z: 280 $[M+H]^+$.

Step 7: (2-tosyl-2-azaspiro[3.3]heptan-6-yl)methanol

To a solution of 2-tosyl-2-azaspiro[3.3]heptane-6-carbaldehyde (850 mg, 3.04 mmol) in EtOH (10 mL) was added $NaBH_4$ (115.1 mg, 3.04 mmol) in portions at 0° C. The mixture was then stirred at room temperature for 2 hrs. The reaction was quenched with aqueous 1M HCl at 0° C., and the mixture was extracted with DCM (50 mL×2). The combined organic layers were dried over $Na_2SO_4$, filtered and concentrated. The residue was purified by silica gel column chromatography (petroleum ether:EtOAc=2:1 to 1:2) to give (2-tosyl-2-azaspiro[3.3]heptan-6-yl)methanol (850 mg, 99.2% yield) as a yellow solid. LC-MS m/z: 282 $[M+H]^+$.

Step 8: (2-tosyl-2-azaspiro[3.3]heptan-6-yl)methyl methanesulfonate

To a solution of (2-tosyl-2-azaspiro[3.3]heptan-6-yl) methanol (850 mg, 3.02 mmol) in DCM (10 mL) was added TEA (1.26 mL, 9.06 mmol) and methanesulfonyl chloride (0.35 mL, 4.53 mmol) dropwise at 0° C. The reaction was stirred at room temperature for 3 hrs. The mixture was diluted with DCM and washed with water. The organic layer was dried over $Na_2SO_4$, filtered and concentrated. The residue was purified by silica gel column chromatography (petroleum ether:EtOAc=3:1 to 1:1) to give (2-tosyl-2-azaspiro[3.3]heptan-6-yl)methyl methanesulfonate (1.0 g, 92.0% yield) as a white solid. LC-MS m/z: 360 $[M+H]^+$.

Step 9: 4-((2-tosyl-2-azaspiro[3.3]heptan-6-yl) methyl)morpholine

To a solution of (2-tosyl-2-azaspiro[3.3]heptan-6-yl) methyl methanesulfonate (500 mg, 1.39 mmol) in acetonitrile (20 mL) was added morpholine (0.24 mL, 2.78 mmol), DIPEA (0.48 mL, 2.78 mmol) and NaI (50 mg, 0.33 mmol). The reaction was stirred at reflux overnight. The mixture was then concentrated and the residue was partitioned between EtOAc (50 mL) and water (50 mL). The organic layer was washed with water, dried over anhydrous $Na_2SO_4$, and concentrated. The residue was purified by silica gel column chromatography (DCM:MeOH=100:1 to 50:1) to give 4-((2-tosyl-2-azaspiro[3.3]heptan-6-yl)methyl)morpholine (450 mg, 92.3% yield) as a brown solid. LC-MS m/z: 351 $[M+H]^+$.

Step 10: 4-(2-azaspiro[3.3]heptan-6-ylmethyl)morpholine

To a solution of 4-((2-tosyl-2-azaspiro[3.3]heptan-6-yl)methyl)morpholine (420 mg, 1.20 mmol) in MeOH (5 mL) was added Na amalgam (2.1 g, 5% wt). The reaction was stirred at reflux overnight. The solution was decanted from the liquid Hg, and the residue was washed with methanol. The solutions were concentrated to give 4-(2-azaspiro[3.3]heptan-6-ylmethyl)morpholine (210 mg, 89.2% yield) as a gray solid, which was directly used to the next reaction without purification. LC-MS m/z: 197 [M+H]+.

Step 11: tert-butyl 6-(morpholinomethyl)-2-azaspiro[3.3]heptane-2-carboxylate

A solution of 4-(2-azaspiro[3.3]heptan-6-ylmethyl)morpholine (210 mg, 1.07 mmol) in H$_2$O (5 mL) was adjusted to pH 10 with aqueous NaOH solution (2 M) at 0° C. The solution was diluted with acetone (5 mL) and (Boc)$_2$O (218.3 mg, 1.28 mmol) was added. After the mixture was stirred at room temperature overnight, it was extracted with DCM. The combined organic layers were dried over Na$_2$SO$_4$, filtered and concentrated. The residue was purified by silica gel column chromatography (DCM:MeOH=100:1 to 30:1) to give tert-butyl 6-(morpholinomethyl)-2-azaspiro[3.3]heptane-2-carboxylate (270 mg, 85.1% yield) as a yellow solid. LC-MS m/z: 297 [M+H]+.

Step 12: 4-(2-azaspiro[3.3]heptan-6-ylmethyl)morpholine

To a mixture of tert-butyl 6-(morpholinomethyl)-2-azaspiro[3.3]heptane-2-carboxylate (270 mg, 0.91 mmol) in DCM (2 mL) was added TFA (2 mL) dropwise at 0° C. The reaction was stirred at room temperature for 2 hrs. The mixture was concentrated under reduced pressure to give 4-(2-azaspiro[3.3]heptan-6-ylmethyl)morpholine trifluoroacetate (170 mg, 95.0% yield) as a yellow syrup, which was directly used to the next reaction without purification. LC-MS m/z: 197 [M+H]+.

Example 1

General Procedure for Coupling of Intermediates

A general procedure for preparation of compounds of the present disclosure is provided below using Example 1 as an illustration.

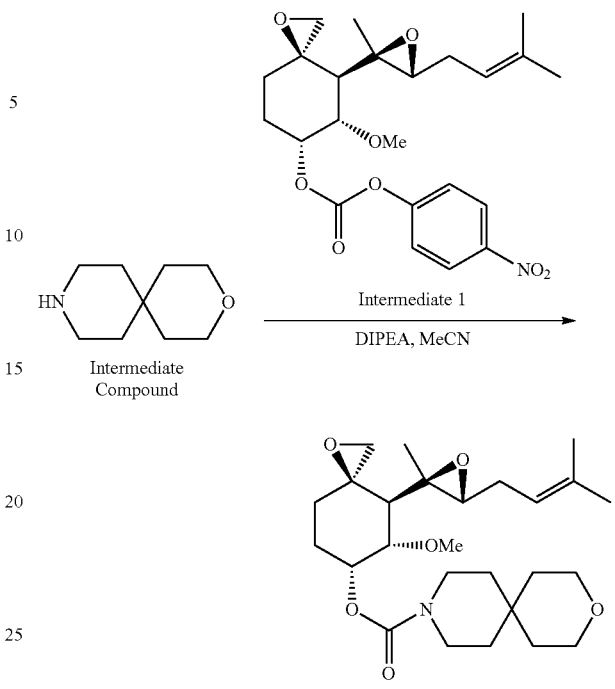

To a mixture of an appropriate intermediate compound in CH$_3$CN was added DIPEA drop-wise at 0-5° C. The mixture was then stirred at 0-5° C. for 10 min, and carbonate Intermediate 1 was added to the mixture in portions at 0° C. under a N$_2$ atmosphere. The reaction mixture was stirred at 25° C. until the reaction was complete as judged by TLC. The solvent was removed under vacuum below 40° C. The residue was diluted with DCM, and the DCM diluent was washed with ammonium acetate buffer (pH~4). The combined aqueous layers were back-extracted with DCM. The combined organic layers were washed with aq. NaHCO$_3$ solution, dried over Na$_2$SO$_4$ and concentrated. Purification by silica gel column chromatography (DCM:MeOH=100:0 to 60:1), followed by preparative HPLC (Method A, H$_2$O (0.1% FA)/CH$_3$CN) gave the title compound. Characterization data are provided below.

The following compounds were prepared according to procedures similar to that described for Example 1 by using the corresponding intermediates.

| Example | Intermediate | Structure | LC-MS | H-NMR (400 MHz, CDCl$_3$) |
|---|---|---|---|---|
| 1 | Commercially available material | 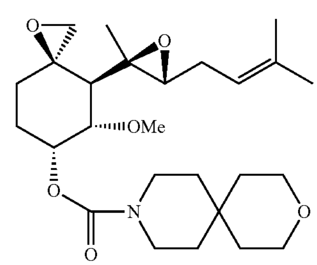 [SMILES: CO[C@@H]1[C@H](OC(=O)N2CCC3(CCOCC3)CC2)CC[C@]2(CO2)[C@H]1[C@@]1(C)O[C@@H]1CC=C(C)C] | 464 [M + H]+ | 5.48-5.50 (m, 1H), 5.11-5.16 (m, 1H), 3.54-3.60 (m, 5H), 3.34-3.37 (m, 7H), 2.92-2.93 (d, J = 4.0 Hz, 1H), 2.47-2.51 (m, 2H), 2.26-2.33 (m, 1H), 2.05-2.13 (m, 1H), 1.87-2.00 (m, 2H), 1.72-1.94 (m, 2H), 1.67 (s, 3H), 1.58 (s, 3H), 1.44 (s, 8H), 1.14 (s, 3H), 1.00-1.05 (m, 1H) |

-continued

| Example | Intermediate | Structure | LC-MS | H-NMR (400 MHz, CDCl₃) |
|---|---|---|---|---|
| 2 | Commercially available material | 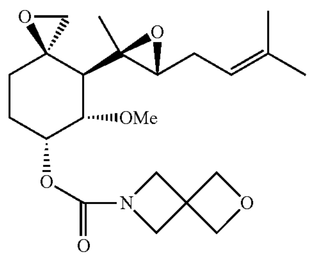 [SMILES: CO[C@@H]1[C@H](OC(=O)N2CC3(COC3)C2)CC[C@]2(CO2)[C@H]1[C@@]1(C)O[C@@H]1CC=C(C)C] | 408 [M + H]⁺ | 5.45 (d, J = 3.2 Hz, 1H), 5.19-5.06 (m, 1H), 4.73-4.68 (m, 4H), 4.10-4.02 (m, 4H), 3.54 (m, 1H), 3.36 (s, 3H), 2.92 (d, J = 4.3 Hz, 1H), 2.51-2.47 (m, 2H), 2.36-2.22 (m, 1H), 2.13-2.06 (m, 1H), 2.02-1.94 (m, 1H), 1.87-1.71 (m, 3H), 1.68 (s, 3H), 1.59 (s, 3H), 1.13 (s, 3H), 1.04-0.95 (m, 1H) |
| 3 | Commercially available material | 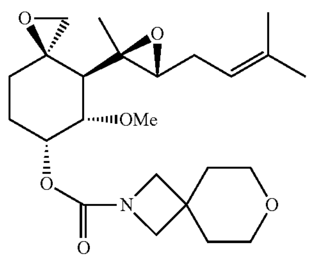 [SMILES: CO[C@@H]1[C@H](OC(=O)N2CC3(CCOCC3)C2)CC[C@]2(CO2)[C@H]1[C@@]1(C)O[C@@H]1CC=C(C)C] | 436 [M + H]⁺ | 5.45 (m, 1H), 5.14 (t, J = 7.5 Hz, 1H), 3.53-3.64 (m, 8H), 3.39 (s, 3H), 2.92 (d, J = 4.3 Hz, 1H), 2.46-2.52 (m, 2H), 2.28-2.29 (m, 1H), 1.95-2.11 (m, 2H), 1.78-1.86 (m, 2H), 1.67-1.77 (m, 6H), 1.59 (s, 3H), 1.52 (s, 3H), 1.14 (s, 3H), 0.91-1.01 (m, 1H) |
| 4 | Commercially available material | 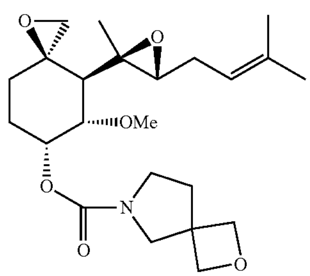 [SMILES: CO[C@@H]1[C@H](OC(=O)N2CCC3(COC3)C2)CC[C@]2(CO2)[C@H]1[C@@]1(C)O[C@@H]1CC=C(C)C] | 422 [M + H]⁺ | 5.59 (d, J = 3.2 Hz, 1H), 5.22-5.24 (m, 1H), 4.68-4.70 (m, 1H), 4.56-4.63 (m, 3H), 3.57-3.69 (m, 3H), 3.33-3.52 (m, 2H), 3.47 (s, 3H), 2.99-3.03 (dd, J = 11.2, 4.4 Hz, 1H), 2.55-2.63 (m, 2H), 2.35-2.40 (m, 1H), 2.15-2.21 (m, 3H), 2.07-2.11 (m, 1H), 1.86-1.98 (m, 3H), 1.76 (s, 3H), 1.67-1.68 (d, J = 4 Hz, 3H), 1.22-1.32 (d, J = 4 Hz, 3H), 1.07-1.13 (m, 1H) |
| 5 | Commercially available material | 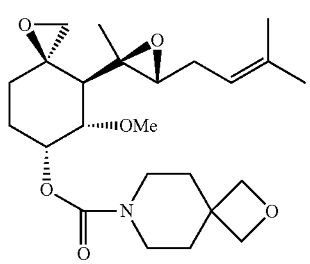 [SMILES: CO[C@@H]1[C@H](OC(=O)N2CCC3(CC2)COC3)CC[C@]2(CO2)[C@H]1[C@@]1(C)O[C@@H]1CC=C(C)C] | 435 [M + H]⁺ | 5.48 (d, J = 2.7 Hz, 1H), 5.14 (m, 1H), 4.43-04.31 (m, 4H), 3.56 (m, 1H), 3.37 (s, 3H), 3.31 (s, 4H), 2.92 (d, J = 4.3 Hz, 1H), 2.54-2.44 (m, 2H), 2.30 (m, 1H), 2.09 (m, 1H), 2.01-1.87 (m, 2H), 1.83-1.73 (m, 5H), 1.68 (s, 3H), 1.59 (s, 3H), 1.18 (s, 1H), 1.14 (s, 3H), 1.06-0.99 (m, 1H) |
| 6 | Commercially available material | 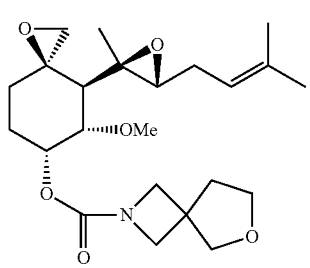 [SMILES: CO[C@@H]1[C@H](OC(=O)N2CC3(CCOC3)C2)CC[C@]2(CO2)[C@H]1[C@@]1(C)O[C@@H]1CC=C(C)C] | 422 [M + H]⁺ | 5.46 (d, J = 3.3 Hz, 1H), 5.14 (t, J = 7.5 Hz, 1H), 3.87 (t, J = 15.7 Hz, 4H), 3.78 (dd, J = 9.8, 6.4 Hz, 4H), 3.54 (dt, J = 10.8, 5.4 Hz, 1H), 3.43-3.36 (m, 3H), 2.91 (d, J = 4.3 Hz, 1H), 2.48 (dd, J = 10.1, 5.3 Hz, 2H), 2.37-02.24 (m, 1H), 2.13-2.03 (m, 3H), 1.96 (dd, J = 13.6, 4.5 Hz, 1H), 1.89-1.83 (m, 1H), 1.78 (dd, J = 12.4, 6.0 Hz, 2H), 1.67(s, 3H), 1.59 (s, 3H), 1.13 (d, J = 6.5 Hz, 3H), 1.03-0.96 (m, 1H) |

| Example | Intermediate | Structure | LC-MS | H-NMR (400 MHz, CDCl₃) |
|---|---|---|---|---|
| 7 | 2 | 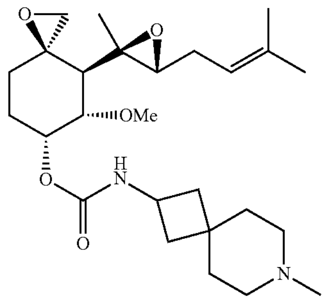 [SMILES: CO[C@@H]1[C@H](OC(=O)NC2CC3(CCN(C)CC3)C2)CC[C@]2(CO2)[C@H]1[C@@]1(C)O[C@@H]1CC=C(C)C] | 463 [M + H]⁺ | 5.39 (s, 1H), 5.10-5.15 (m, 1H), 4.84 (d, J = 7.6 Hz, 1H), 4.02-4.06 (m, 1H), 3.54-3.57 (m, 1H), 3.38 (s, 3H), 2.90 (d, J = 4.4 Hz, 1H), 2.47-2.48 (m, 6H), 206-2.33 (m, 5H), 1.91-1.99 (m, 2H), 1.71-1.85 (m, 6H), 1.62-1.67 (m, 7H), 1.58 (s, 3H), 1.13 (s, 3H), 0.93-1.00 (m, 1H) |
| 8 | 3 | 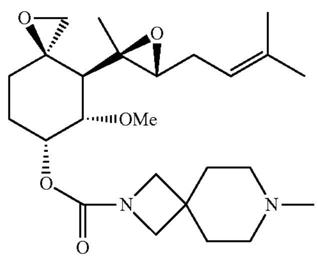 [SMILES: CO[C@@H]1[C@H](OC(=O)N2CC3(CCN(C)CC3)C2)CC[C@]2(CO2)[C@H]1[C@@]1(C)O[C@@H]1CC=C(C)C] | 449 [M + H]⁺ | 5.54 (d, J = 3.0 Hz, 1H), 5.29-5.15 (m, 1H), 3.78 (d, J = 48.8 Hz, 4H), 3.64 (dd, J = 11.2, 2.7 Hz, 1H), 3.45 (d, J = 9.9 Hz, 3H), 2.90 (dd, J = 79.5, 21.1 Hz, 4H), 2.57 (q, J = 4.0 Hz, 5H), 2.43-2.31 (m, 1H), 2.18 (dt, J = 14.8, 7.3 Hz, 1H), 2.11-2.00 (m, 5H), 1.99-1.92 (m, 1H), 1.90-1.82 (m, 2H), 1.76 (s, 2H), 1.68 (s, 3H), 1.22 (s, 3H), 1.12-1.02 (m, 1H) |
| 9 | 4 | 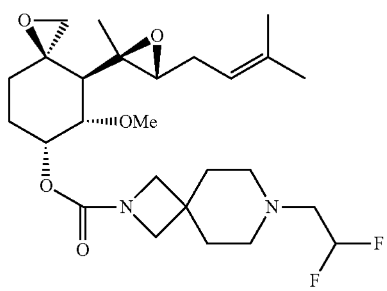 [SMILES: CO[C@@H]1[C@H](OC(=O)N2CC3(CCN(CC(F)F)CC3)C2)CC[C@]2(CO2)[C@H]1[C@@]1(C)O[C@@H]1CC=C(C)C] | 499 [M + H]⁺ | 5.82 (tt, J = 55.8, 4.3 Hz, 1H), 5.45 (d, J = 3.2 Hz, 1H), 5.18-5.09 (m, 1H), 3.71-3.50 (m, 5H), 3.38 (s, 3H), 2.91 (d, J = 4.3 Hz, 1H), 2.66 (td, J = 15.0, 4.3 Hz, 2H), 2.48 (dt, J = 10.2, 6.1 Hz, 6H), 2.29 (dt, J = 13.7, 6.6 Hz, 1H), 2.10 (dt, J = 14.8, 7.4 Hz, 1H), 1.98 (td, J = 13.5, 4.4 Hz, 1H), 1.92-1.83 (m, 1H), 1.82-1.69 (m, 6H), 1.68 (s, 3H), 1.59 (s, 3H), 1.14 (s, 3H), 1.03-0.94 (m, 1H) |
| 10 | 5 | 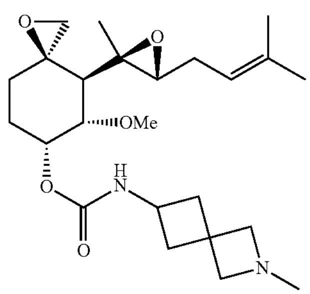 [SMILES: CO[C@@H]1[C@H](OC(=O)NC2CC3(C2)CN(C)C3)CC[C@]2(CO2)[C@H]1[C@@]1(C)O[C@@H]1CC=C(C)C] | 435 [M + H]⁺ | 5.38 (s, 1H), 5.13 (t, J = 8.0 Hz, 1H), 4.98 (d, J = 6.8 Hz, 1H), 3.86-3.93 (m, 5H), 3.53-3.57 (m, 1H), 3.35 (s, 3H), 2.90 (d, J = 4.4 Hz, 1H), 2.56-2.62 (m, 5H), 2.27-2.31 (m, 1H), 2.08-2.13 (m, 3H), 1.73-1.92 (m, 4H), 1.76 (s, 3H), 1.67 (s, 3H), 1.18 (s, 3H), 0.98 (d, J = 8.8 Hz, 1H) |
| 11 | 6 | 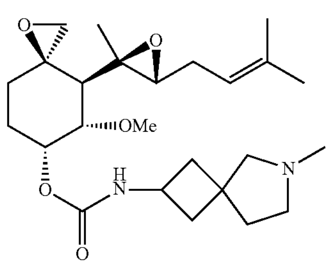 [SMILES: CO[C@@H]1[C@H](OC(=O)NC2CC3(CCN(C)C3)C2)CC[C@]2(CO2)[C@H]1[C@@]1(C)O[C@@H]1CC=C(C)C] | 449 [M + H]⁺ | 5.47 (s, 1H), 5.05-5.23 (m, 2H), 4.13-4.16 (m, 1H), 3.44 (s, 3H), 3.11-3.32 (m, 4H), 2.97 (d, J = 4.4 Hz, 1H), 2.72 (s, 2H), 2.55-2.59 (m, 2H), 2.33-2.47 (m, 3H), 1.90-2.22 (m, 9H), 1.76 (s, 3H), 1.67 (s, 3H), 1.21 (s, 3H), 1.05 (d, J = 8.8 Hz, 1H) |

-continued

| Example | Intermediate | Structure | LC-MS | H-NMR (400 MHz, CDCl$_3$) |
|---|---|---|---|---|
| 12 | 7 | 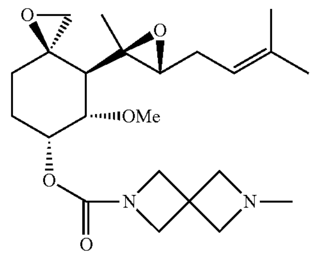 [SMILES: CO[C@@H]1[C@H](OC(=O)N2CC3(CN(C)C3)C2)CC[C@]2(CO2)[C@H]1[C@@]1(C)O[C@@H]1CC=C(C)C] | 421 [M + H]$^+$ | 5.44 (d, J = 3.2 Hz, 1H), 5.19-5.09 (m, 1H), 3.94 (m, 4H), 3.53 (m, 1H), 3.37 (s, 3H), 3.26 (m, 4H), 2.91 (m, 1H), 2.51-2.44 (,. 2H), 2.34-2.24 (m, 1H), 2.23 (s, 3H), 2.10 (m, 1H), 2.02-1.93 (m, 1H), 1.89-1.70 (m, 5H), 1.68 (s, 3H), 1.13 (s, 3H), 1.03-0.95 (m, 1H) |
| 13 | 8 | 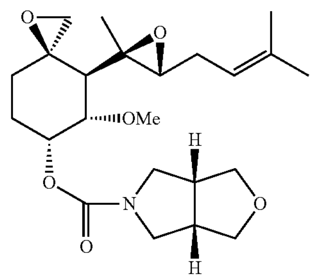 [SMILES: CO[C@@H]1[C@H](OC(=O)N2C[C@H]3COC[C@H]3C2)CC[C@]2(CO2)[C@H]1[C@@]1(C)O[C@@H]1CC=C(C)C] | 422 [M + H]$^+$ | 5.49 (s, 1H), 5.18-5.08 (m, 1H), 3.83 (dt, J = 16.8, 8.4 Hz, 2H), 3.71-3.42 (m, 5H), 3.37 (d, J = 13.4 Hz, 3H), 3.32-3.10 (m, 2H), 2.90 (t, J = 13.2 Hz, 3H), 2.49 (dd, J = 13.2, 5.4 Hz, 2H), 2.34-2.21 (m, 1H), 2.10 (dt, J = 17.8, 7.3 Hz, 1H), 2.04-1.85 (m, 2H), 1.84-1.72 (m, 2H), 1.67 (s, 3H), 1.59 (s, 3H), 1.16 (d, J = 17.3 Hz, 3H), 1.02 (d, J = 12.6 Hz, 1H) |
| 14 | 9 | 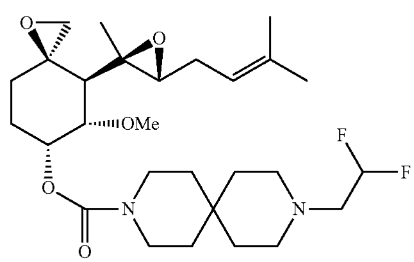 [SMILES: CO[C@@H]1[C@H](OC(=O)N2CCC3(CCN(CC(F)F)CC3)CC2)CC[C@]2(CO2)[C@H]1[C@@]1(C)O[C@@H]1CC=C(C)C] | 527 [M + H]$^+$ | 5.90 (t, J = 55.4 Hz, 1H), 5.48 (d, J = 3.1 Hz, 1H), 5.20-5.09 (m, 1H), 3.56 (dd, J = 11.1, 2.7 Hz, 1H), 3.37 (s, 3H), 3.36-3.29 (m, 3H), 2.92 (d, J = 4.3 Hz, 1H), 2.72 (t, J = 13.2 Hz, 2H), 2.62-2.43 (m, 6H), 2.34-2.24 (m, 1H), 2.09 (dt, J = 14.7, 7.3 Hz, 1H), 2.01-1.88 (m, 2H), 1.78 (dd, J = 12.4, 5.1 Hz, 2H), 1.68 (s, 3H), 1.59 (s, 3H), 1.52 (s, 4H), 1.38 (d, J = 29.3 Hz, 4H), 1.13 (d, J = 6.7 Hz, 3H), 1.02 (dd, J = 11.1, 3.8 Hz, 1H) |
| 15 | 10 | 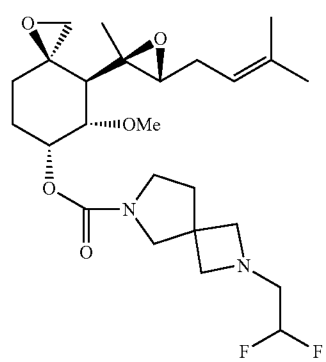 [SMILES: CO[C@@H]1[C@H](OC(=O)N2CCC3(CN(CC(F)F)C3)C2)CC[C@]2(CO2)[C@H]1[C@@]1(C)O[C@@H]1CC=C(C)C] | 485 [M + H]$^+$ | 5.68 (m, 1H), 5.49 (s, 1H), 5.13 (m, 1H), 3.59-3.18 (m, 12H), 2.92 (m, 1H), 2.74 (m, 2H), 2.56-5.44 (m, 2H), 2.29 (m, 1H), 2.16-2.05 (m, 1H), 2.04-1.88 (m, 3H), 1.85 (m, 1H), 1.77 (m, 2H), 1.68 (s, 3H), 1.59 (d, J = 4.5 Hz, 3H), 1.14 (d, J = 2.5 Hz, 3H), 1.01 (d, J = 13.6 Hz, 1H) |
| 16 | 11 | 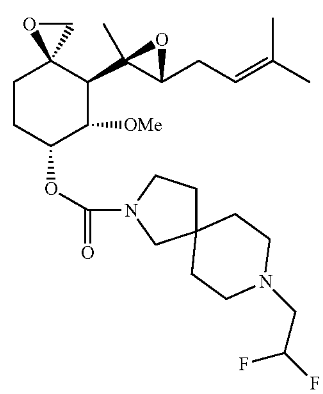 [SMILES: CO[C@@H]1[C@H](OC(=O)N2CCC3(CCN(CC(F)F)CC3)C2)CC[C@]2(CO2)[C@H]1[C@@]1(C)O[C@@H]1CC=C(C)C] | 513 [M + H]$^+$ | 5.87 (m, 1H), 5.57 (s, 1H), 5.19 (d, J = 20.0 Hz, 1H), 3.62 (m, 1H), 3.54-3.30 (m, 5H), 3.27 (d, J = 10.8 Hz, 1H), 3.15 (m, 1H), 3.03-2.95 (m, 1H), 2.79-2.67 (m, 2H), 2.66-2.31 (m, 7H), 2.22-2.02 (m, 2H), 1.99-1.79 (m, 3H), 1.74 (s, 3H), 1.71 (m, 2H), 1.66 (s, 3H), 1.60 (m, 4H), 1.21 (s, 3H), 1.09 (m, 1H) |

-continued

| Example | Intermediate | Structure | LC-MS | H-NMR (400 MHz, CDCl$_3$) |
|---|---|---|---|---|
| 17 | 12 | 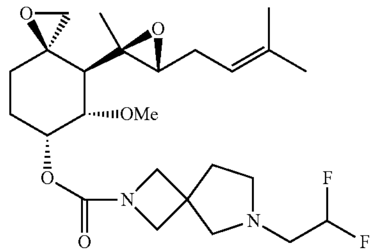 [SMILES: CO[C@@H]1[C@H](OC(=O)N2CC3(CCN(CC(F)F)C3)C2)CC[C@]2(CO2)[C@H]1[C@@]1(C)O[C@@H]1CC=C(C)C] | 485 [M + H]$^+$ | 5.84 (s, 1H), 5.45 (s, 1H), 5.14 (t, J = 7.5 Hz, 1H), 3.85 (s, 4H), 3.54 (dd, J = 11.2, 2.7 Hz, 1H), 3.38 (s, 3H), 2.91 (d, J = 4.3 Hz, 1H), 2.89-2.56 (m, 5H), 2.48 (dd, J = 14.8, 5.2 Hz, 2H), 2.29 (dt, J = 13.5, 6.6 Hz, 1H), 2.16-1.91 (m, 4H), 1.90-1.81 (m, 1H), 1.78 (dd, J = 10.2, 6.0 Hz, 2H), 1.68 (s, 3H), 1.59 (s, 3H), 1.18 (s, 1H), 1.12 (d, J = 6.2 Hz, 3H), 0.99 (dd, J = 10.5, 3.4 Hz, 1H) |
| 18 | 13 | 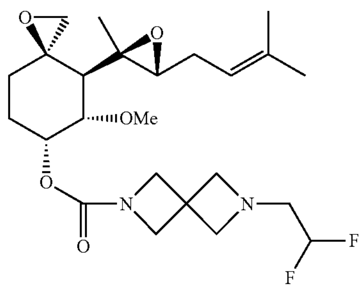 [SMILES: CO[C@@H]1[C@H](OC(=O)N2CC3(CN(CC(F)F)C3)C2)CC[C@]2(CO2)[C@H]1[C@@]1(C)O[C@@H]1CC=C(C)C] | 471 [M + H]$^+$ | 5.67 (tt, J = 55.8, 4.3 Hz, 1H), 5.43 (s, 1H), 5.18-5.10 (m, 1H), 3.95 (m, 4H), 3.53 (dd, J = 11.2, 2.7 Hz, 1H), 3.40 (d, J = 3.4 3H), 3.37 (s, 3H), 2.91 (d, J = 4.3 Hz, 1H), 2.70 (m, 2H), 2.52-2.45 (m, 2H), 2.35-2.23 (m, 1H), 2.09 (dt, J = 14.8, 7.3 Hz, 1H), 1.97 (dt, J = 13.5, 4.2 Hz, 1H), 1.88-1.71 (m, 4H), 1.68 (s, 3H), 1.59 (s, 3H), 1.12 (s, 3H), 1.02-0.96 (m, 1H) |
| 19 | Commercially available material | 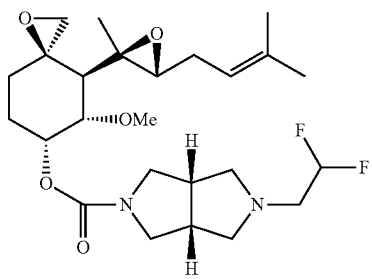 [SMILES: CO[C@@H]1[C@H](OC(=O)N2C[C@H]3CN(CC(F)F)C[C@H]3C2)CC[C@]2(CO2)[C@H]1[C@@]1(C)O[C@@H]1CC=C(C)C] | 485 [M + H]$^+$ | 6.08 (t, J = 55.6 Hz, 1H), 5.35 (s, 1H), 5.20 (t, J = 7.5 Hz, 1H), 3.54 (dd, J = 11.1, 2.4 Hz, 3H), 3.29 (s, 3H), 3.14 (d, J = 9.1 Hz, 2H), 2.86 (d, J = 4.4 Hz, 1H), 2.80 (dd, J = 15.8, 11.8 Hz, 4H), 2.63 (t, J = 7.8 Hz, 2H), 2.58 (d, J = 4.4 Hz, 1H), 2.56-2.51 (m, 3H), 2.18 (t, J = 6.8 Hz, 2H), 2.08 (s, 1H), 1.97 (td, J = 13.3, 4.4 Hz, 1H), 1.78 (dd, J = 16.4, 11.6 Hz, 2H), 1.71 (s, 3H), 1.62 (s, 3H), 1.08 (s, 3H), 1.01 (d, J = 13.4 Hz, 1H) |
| 20 | Commercially available material | 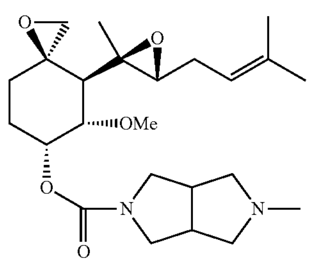 [SMILES: CO[C@@H]1[C@H](OC(=O)N2CC3CN(C)CC3C2)CC[C@]2(CO2)[C@H]1[C@@]1(C)O[C@@H]1CC=C(C)C] | 435 [M + H]$^+$ | 5.34 (s, 1H), 5.18-5.21 (m, 1H), 3.49-3.55 (m, 4H), 3.28 (s, 3H), 3.09-3.17 (m, 3H), 2.86 (d, J = 4.0 Hz, 1H), 2.79 (s, 2H), 2.54-2.58 (m, 2H), 2.51 (s, 3H), 2.25 (s, 3H), 2.16-2.19 (m, 2H), 1.94-2.00 (m, 1H), 1.76-1.81 (m, 2H), 1.71 (s, 3H), 1.61 (s, 3H), 1.08 (s, 3H), 1.01 (d, J = 13.6 Hz, 1H) |
| 21 | Commercially available material | 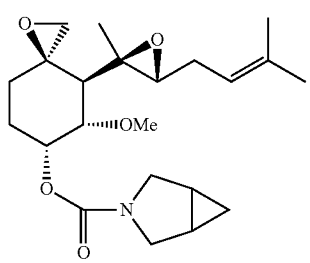 | 362 [M + H]$^+$ | 5.52 (d, J = 10.7 Hz, 1H), 5.22 (t, J = 7.5 Hz, 1H), 3.66-3.53 (m, 2H), 3.53-3.24 (m, 6H), 2.99 (d, J = 4.3 Hz, 1H), 2.64-2.47 (m, 2H), 2.37-2.33 (m, 1H), 2.20-2.13 (m, 1H), 2.09-2.00 (m, 1H), 1.99-1.79 (m, 3H), 1.75 (s, 3H), 1.66 (s, 3H), 1.54-1.39 (m, 2H), 1.20 (s, 3H), 1.07 (d, J = 13.6 Hz, 1H), 0.69 (d, J = 7.2 Hz, 1H), 0.26-0.14 (m, 1H) |

| Example | Intermediate | Structure | LC-MS | H-NMR (400 MHz, CDCl$_3$) |
|---|---|---|---|---|
| 22 | Commercially available material | 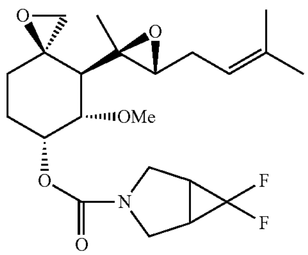 [SMILES: CO[C@@H]1[C@H](OC(=O)N2CC3C(C2)C3(F)F)CC[C@]2(CO2)[C@H]1[C@@]1(C)O[C@@H]1CC=C(C)C] | 428 [M + H]$^+$ | 7.54 (d, J = 23.9 Hz, 1H), 6.78 (d, J = 14.7 Hz, 1H), 5.74 (d, J = 9.2 Hz, 1H), 5.45 (s, 1H), 5.12 (t, J = 7.1 Hz, 1H), 4.44-4.33 (m, 1H), 4.11-3.99 (m, 1H), 3.91 (dd, J = 13.8, 6.0 Hz, 1H), 3.54 (dd, J = 11.3, 2.4 Hz, 1H), 3.36 (d, J = 21.0 Hz, 4H), 3.11 (s, 1H), 2.90 (td, J = 20.1, 9.6 Hz, 4H), 2.65 (s, 3H), 2.54-2.45 (m, 2H), 2.28 (dd, J = 14.2, 6.5 Hz, 1H), 2.19-2.03 (m, 4H), 1.96-1.83 (m, 2H), 1.78 (s, 1H), 1.67 (s, 3H), 1.58 (s, 3H), 1.18 (s, 1H), 1.11 (s, 3H), 1.00 (d, J = 7.6 Hz, 1H), 0.84 (d, J = 6.7 Hz, 3H), 0.76 (d, J = 6.6 Hz, 3H) |
| 23 | Commercially available material | 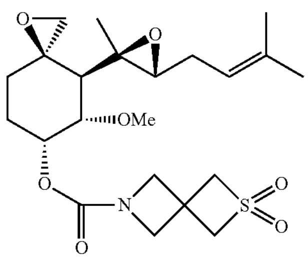 [SMILES: CO[C@@H]1[C@H](OC(=O)N2CC3(C2)CS(=O)(=O)C3)CC[C@]2(CO2)[C@H]1[C@@]1(C)O[C@@H]1CC=C(C)C] | 456 [M + H]$^+$ | 5.57 (d, J = 2.9 Hz, 1H), 5.23 (t, J = 7.5 Hz, 1H), 4.44-4.13 (m, 8H), 3.64 (dd, J = 11.3, 2.7 Hz, 1H), 3.52-3.39 (m, 3H), 3.01 (d, J = 4.3 Hz, 1H), 2.61-2.53 (m, 2H), 2.44-2.33 (m, 1H), 2.18 (dt, J = 14.8, 7.3 Hz, 1H), 2.05 (td, J = 13.3, 5.0 Hz, 1H), 1.97-1.86 (m, 2H), 1.83 (d, J = 11.3 Hz, 1H), 1.78 (d, J = 8.4 Hz, 3H), 1.68 (s, 3H), 1.21 (s, 3H), 1.14-1.06 (m, 1H) |
| 24 | Commercially available material | 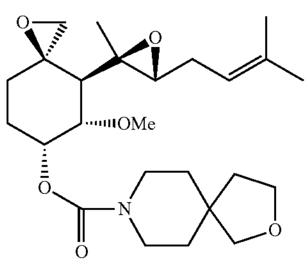 [SMILES: CO[C@@H]1[C@H](OC(=O)N2CCC3(CCOC3)CC2)CC[C@]2(CO2)[C@H]1[C@@]1(C)O[C@@H]1CC=C(C)C] | 450 [M + H]$^+$ | 5.49(s, 1H), 5.14 (t, J = 7.5 Hz, 1H), 3.80 (t, J = 7.1 Hz, 2H), 3.57 (dd, J = 11.1, 2.7 Hz, 1H), 3.49 (s, 2H), 3.44=3.16 (m, 6H), 2.92 (d, J = 4.3 Hz, 1H), 2.49 (dd, J = 13.6, 5.3 Hz, 2H), 2.34-2.24 (m, 1H), 2.16-2.03 (m, 1H), 2.02-1.85 (m, 2H), 1.85-1.72 (m, 2H), 1.76-1.62 (m, 4H), 1.59 (s, 3H), 1.51-1.42 (m, 6H), 1.14 (s, 3H), 1.07-0.99 (m, 1H) |
| 25 | Commercially available material | 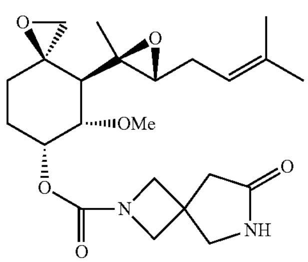 [SMILES: CO[C@@H]1[C@H](OC(=O)N2CC3(CNC(=O)C3)C2)CC[C@]2(CO2)[C@H]1[C@@]1(C)O[C@@H]1CC=C(C)C] | 435 [M + H]$^+$ | 5.63 (s, 1H), 5.47 (d, J = 2.6 Hz, 1H), 5.13 (t, J = 7.4 Hz, 1H), 4.05-3.83 (m, 4H), 3.53 (dt, J = 19.3, 6.4 Hz, 3H), 3.39 (s, 3H), 2.91 (d, J = 4.3 Hz, 1H), 2.54-2.44 (m, 4H), 2.35-2.24 (m, 1H), 2.09 (dt, J = 14.7, 7.4 Hz, 1H), 1.97 (td, J = 13.5, 4.4 Hz, 1H), 1.90-1.73 (m, 3H), 1.68 (s, 3H), 1.59 (s, 3H), 1.12 (d, J = 6.2 Hz, 3H), 1.00 (d, J = 13.6 Hz, 1H) |
| 26 | Commercially available material | 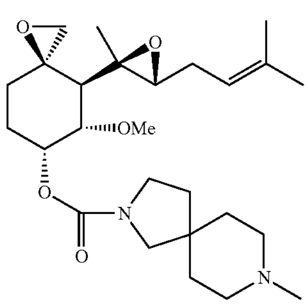 [SMILES: CO[C@@H]1[C@H](OC(=O)N2CCC3(CCN(C)CC3)C2)CC[C@]2(CO2)[C@H]1[C@@]1(C)O[C@@H]1CC=C(C)C] | 463 [M + H]$^+$ | 5.51 (br, 1H), 5.14-5.19 (m, 1H), 3.54-3.57 (m, 1H), 3.22-3.39 (m, 4H), 3.16-3.21 (m, 2H), 2.92-3.04 (m, 1H), 2.26-2.52 (m, 5H), 1.84-2.12 (m, 6H), 1.77-1.80 (m, 3H), 1.61-1.74 (m, 8H), 1.59 (s, 3H), 1.45-1.58 (m, 3H), 1.18 (s, 3H), 0.98-1.02 (m, 1H) |

| Example | Intermediate | Structure | LC-MS | H-NMR (400 MHz, CDCl$_3$) |
|---|---|---|---|---|
| 27 | Commercially available material | 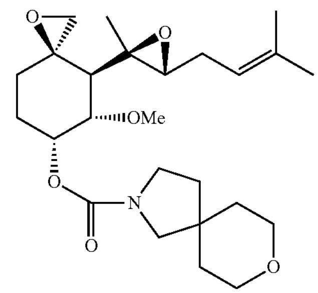 [SMILES: CO[C@@H]1[C@H](OC(=O)N2CCC3(CCOCC3)C2)CC[C@]2(CO2)[C@H]1[C@@]1(C)O[C@@H]1CC=C(C)C] | 450 [M + H]$^+$ | 5.37-5.31 (m, 1H), 5.27-5.14 (m, 1H), 3.68-3.48 (m, 5H), 3.36 (m, 2H), 3.31 (s, 3H), 3.20 (s, 2H), 2.86 (d, J = 4.4 Hz, 1H), 2.57 (d, J = 4.4 Hz, 2H), 2.19 (m, 2H), 1.97 (m, 4.6 Hz, 1H), 1.89-1.67 (m, 8H), 1.63 (s, 3H), 1.55-1.41 (m, 4H), 1.12 (s, 3H), 1.08 (m, 1H) |
| 28 | Commercially available material | 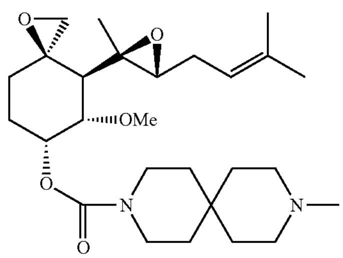 [SMILES: CO[C@@H]1[C@H](OC(=O)N2CCC3(CCN(C)CC3)CC2)CC[C@]2(CO2)[C@H]1[C@@]1(C)O[C@@H]1CC=C(C)C] | 477 [M + H]$^+$ | 5.48 (d, J = 2.8 Hz, 1H), 5.18-5.09 (m, 1H), 3.56 (dd, J = 11.1, 2.7 Hz, 1H), 3.38 (s, 4H), 3.34 (d, J = 5.5 Hz, 3H), 2.92 (d, J = 4.3 Hz, 1H), 2.49 (dd, J = 13.2, 5.4 Hz, 2H), 2.39 (s, 3H), 2.27 (s, 3H), 2.14-2.04 (m, 2H), 2.01-1.86 (m, 3H), 1.82-1.75 (m, 2H), 1.67 (s, 3H), 1.59 (s, 3H), 1.53 (s, 4H), 1.36 (d, J = 47.3 Hz, 4H), 1.13 (d, J = 6.5 Hz, 3H), 1.02 (dd, J = 11.2, 3.8 Hz, 1H) |
| 29 | Commercially available material | 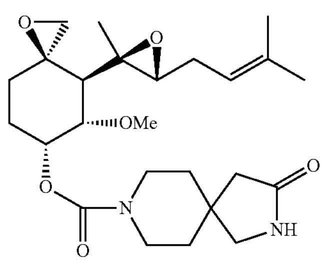 [SMILES: CO[C@@H]1[C@H](OC(=O)N2CCC3(CC2)CNC(=O)C3)CC[C@]2(CO2)[C@H]1[C@@]1(C)O[C@@H]1CC=C(C)C] | 463 [M + H]$^+$ | 5.52 (s, 1H), 5.50 (s, 1H), 5.14 (m, 1H), 3.61-3.43 (m, 3H), 3.37 (s, 3H), 3.26 (m, 2H), 3.18-3.13 (m, 2H), 2.92 (d, J = 4.3 Hz, 1H), 2.49 (m, 2H), 2.35-2.24 (m, 1H), 2.18 (m, 2H), 2.09 (m, 1H), 2.02-1.87 (m, 2H), 1.84-1.74 (m, 2H), 1.67 (s, 3H), 1.58 (m, 7H), 1.13 (m, 3H), 1.07-1.00 (m, 1H) |
| 30 | Commercially available material | 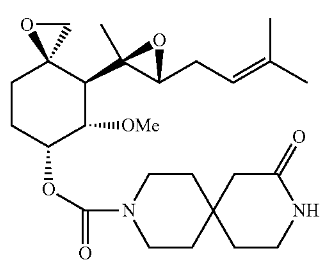 [SMILES: CO[C@@H]1[C@H](OC(=O)N2CCC3(CCNC(=O)C3)CC2)CC[C@]2(CO2)[C@H]1[C@@]1(C)O[C@@H]1CC=C(C)C] | 477 [M + H]$^+$ | 5.49(s, 1H), 5.14 (t, J = 7.5 Hz, 1H), 3.60-3.40 (m, 5H), 3.38 (d, J = 2.9 Hz, 3H), 3.32 (s, 4H), 2.92 (d, J = 4.3 Hz, 1H), 2.48 (d, J = 4.4 Hz, 2H), 2.24 (s, 3H), 2.10 (s, 1H), 2.00-1.88 (m, 2H), 1.77 (dd, J = 12.3, 6.1 Hz, 5H), 1.67 (s, 4H), 1.59 (s, 3H), 1.14 (s, 3H), 1.04 (d, J = 13.3 Hz, 1H) |
| 31 | Commercially available material | 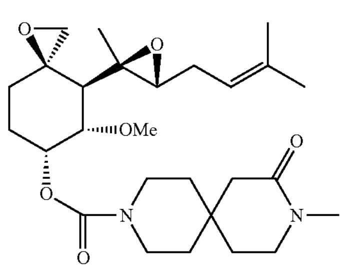 [SMILES: CO[C@@H]1[C@H](OC(=O)N2CCC3(CCN(C)C(=O)C3)CC2)CC[C@]2(CO2)[C@H]1[C@@]1(C)O[C@@H]1CC=C(C)C] | 491 [M + H]$^+$ | 5.48 (s, 1H), 5.13 (m, 1H), 3.56 (dd, J = 11.1, 2.7 Hz, 1H), 3.47 (s, 2H), 3.37 (s, 3H), 3.31-3.22 (m, 4H), 2.92 (d, J = 4.3 Hz, 1H), 2.87 (s, 3H), 2.49 (m, 2H), 2.33-2.20 (m, 3H), 2.09 (m, 1H), 2.00-1.88 (m, 2H), 2.01-1.87 (m, 2H), 1.85-1.74 (m, 2H), 1.67 (m, 5H), 1.59 (s, 3H), 1.41 m, 4H), 1.13 (s, 3H), 1.03 (d, J = 13.5 Hz, 1H) |

| Example | Intermediate | Structure | LC-MS | H-NMR (400 MHz, CDCl₃) |
|---------|--------------|-----------|-------|------------------------|
| 32 | 14 | 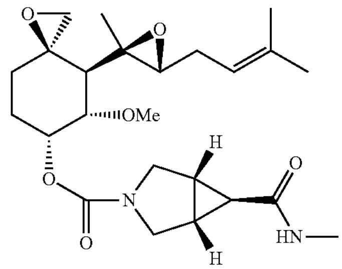 [SMILES: CNC(=O)[C@H]1[C@@H]2CN(C(=O)O[C@@H]3CC[C@]4(CO4)[C@@H]([C@@]4(C)O[C@@H]4CC=C(C)C)[C@@H]3OC)C[C@@H]21] | 449 [M + H]⁺ | 5.51 (t, J = 7.1 Hz, 1H), 5.12 (d, J = 6.3 Hz, 1H), 3.70-3.23 (m, 8H), 2.91 (t, J = 5.3 Hz, 1H), 2.74 (dd, J = 10.2, 4.6 Hz, 3H), 2.62-2.47 (m, 2H), 2.34-2.20 (m, 1H), 2.04 (qdd, J = 17.3, 13.6, 6.9 Hz, 3H), 1.91-1.71 (m, 4H), 1.68 (s, 3H), 1.59 (s, 3H), 1.25 (t, J = 3.0 Hz, 1H), 1.13 (s, 3H), 1.00 (d, J = 11.8 Hz, 1H) |
| 33 | 15 | 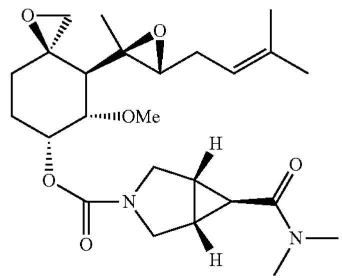 [SMILES: CO[C@@H]1[C@H](OC(=O)N2C[C@@H]3[C@H](C2)[C@H]3C(=O)N(C)C)CC[C@]2(CO2)[C@H]1[C@@]1(C)O[C@@H]1CC=C(C)C] | 463 [M + H]⁺ | 5.49 (s, 1H), 5.19-5.07 (m, 1H), 3.66-3.50 (m, 3H), 3.49-3.39 (m, 2H), 3.39-3.33 (m, 3H), 3.08 (d, J = 20.6 Hz, 3H), 2.92 (d, J = 4.3 Hz, 1H), 2.89 (s, 3H), 2.49 (dd, J = 10.4, 5.3 Hz, 2H), 2.33-2.23 (m, 1H), 2.15-1.91 (m, 4H), 1.84 (ddd, J = 24.6, 10.8, 4.8 Hz, 3H), 1.67 (d, J = 7.4 Hz, 3H), 1.59 (s, 3H), 1.20 (d, J = 12.2 Hz, 1H), 1.13 (s, 3H), 1.01 (t, J = 12.2 Hz, 1H) |
| 34 | 16 | 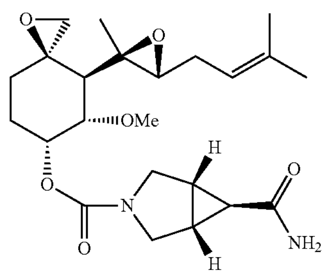 [SMILES: CO[C@@H]1[C@H](OC(=O)N2C[C@@H]3[C@H](C2)[C@H]3C(N)=O)CC[C@]2(CO2)[C@H]1[C@@]1(C)O[C@@H]1CC=C(C)C] | 435 [M + H]⁺ | 5.39-5.51 (m, 1H), 5.10-5.13 (m, 1H), 3.61-3.76 (m, 2H), 3.52-3.57 (m, 2H), 3.36-3.38 (m, 1H), 3.37 (s, 3H), 2.90-2.92 (m, 1H), 2.48-2.52 (m, 2H), 2.26-2.29 (m, 1H), 1.93-2.12 (m, 4H), 1.72-1.85 (m, 7H), 1.68 (s, 3H), 1.57 (s, 3H), 1.12 (s, 3H), 0.99-1.01 (m, 1H) |
| 35 | 17 | 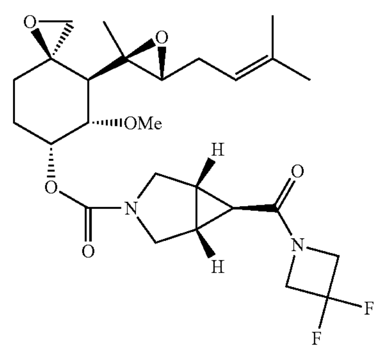 [SMILES: CO[C@@H]1[C@H](OC(=O)N2C[C@@H]3[C@H](C2)[C@H]3C(=O)N2CC(F)(F)C2)CC[C@]2(CO2)[C@H]1[C@@]1(C)O[C@@H]1CC=C(C)C] | 511 [M + H]⁺ | 5.50 (s, 1H), 5.14 (t, J = 7.4 Hz, 1H), 4.67 (s, 1H), 4.48 (d, J = 11.5 Hz, 1H), 4.24 (t, J = 12.1 Hz, 2H), 3.69-3.30 (m, 9H), 2.92 (d, J = 4.3 Hz, 1H), 2.48 (t, J = 4.1 Hz, 2H), 2.28 (d, J = 7.0 Hz, 1H), 2.16-1.88 (m, 4H), 1.79 (dd, J = 20.6, 11.3 Hz, 3H), 1.68 (s, 3H), 1.59 (s, 3H), 1.34 (s, 1H), 1.13 (s, 3H), 1.00 (d, J = 13.3 Hz, 1H) |
| 36 | 18 | 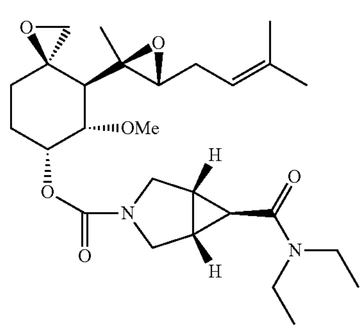 [SMILES: CCN(CC)C(=O)[C@H]1[C@@H]2CN(C(=O)O[C@@H]3CC[C@]4(CO4)[C@@H]([C@@]4(C)O[C@@H]4CC=C(C)C)[C@@H]3OC)C[C@@H]21] | 491 [M + H]⁺ | 7.95 (s, 1H), 5.49 (s, 1H), 5.14 (s, 1H), 3.56 (ddd, J = 11.3, 10.5, 7.2 Hz, 3H), 3.47 (dd, J = 21.0, 10.3 Hz, 2H), 3.41-3.36 (m, 3H), 3.37-3.15 (m, 4H), 2.92 J = 4.3 Hz, 1H), 2.48 (d, J = 4.3 Hz, 2H), 2.34-2.24 (m, 1H), 2.10-1.97 (m, 3H), 1.81 (dd, J = 19.3, 8.2 Hz, 3H), 1.68 (s, 3H), 1.59 (s, 3H), 1.15 (q, J = 6.7 Hz, 7H), 1.06 (dd, J = 20.1, 16.8 Hz, 5H) |

-continued

| Example | Intermediate | Structure | LC-MS | H-NMR (400 MHz, CDCl₃) |
|---|---|---|---|---|
| 37 | 19 | 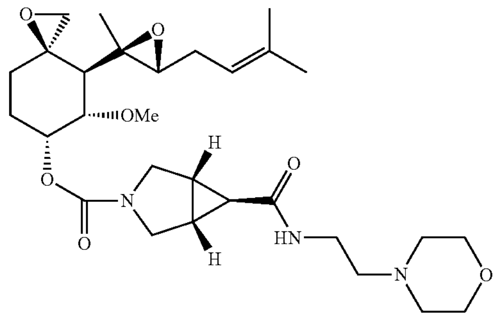 [SMILES: CO[C@@H]1[C@H](OC(=O)N2C[C@@H]3[C@H](C2)[C@H]3C(=O)NCCN2CCOCC2)CC[C@]2(CO2)[C@H]1[C@@]1(C)O[C@@H]1CC=C(C)C] | 548 [M + H]⁺ | 5.49 (s, 1H), 5.13 (s, 1H), 3.86-3.74 (m, 6H), 3.68-3.44 (m, 5H), 3.39 (dd, J = 11.1, 3.7 Hz, 5H), 2.91 (d, J = 4.3 Hz, 1H), 2.80 (d, J = 4.4 Hz, 2H), 2.64 (d, J = 5.6 Hz, 3H), 2.48 (d, J = 4.2 Hz, 2H), 2.28 (d, J = 7.2 Hz, 1H), 2.13-1.86 (m, 5H), 1.79 (d, J = 5.4 Hz, 2H), 1.68 (s, 3H), 1.59 (s, 3H), 1.13 (s, 3H), 1.01 (s, 1H) |
| 38 | 20 | 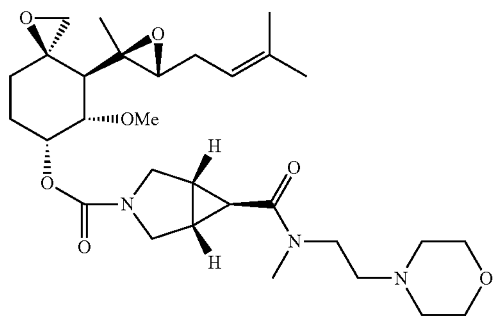 [SMILES: CO[C@@H]1[C@H](OC(=O)N2C[C@@H]3[C@H](C2)[C@H]3C(=O)N(C)CCN2CCOCC2)CC[C@]2(CO2)[C@H]1[C@@]1(C)O[C@@H]1CC=C(C)C] | 562 [M + H]⁺ | 5.49(s, 1H), 5.14 (t, J = 7.4 Hz, 1H), 3.86-3.31 (m, 14H), 3.12 (d, J = 14.1 Hz, 2H), 2.91 (t, J = 6.8 Hz, 2H), 2.50 (tt, J = 24.4, 12.2 Hz, 7H), 2.33-2.23 (m, 1H), 2.16-1.92 (m, 4H), 1.89-1.73 (m, 3H), 1.68 (s, 3H), 1.64-1.54 (m, 4H), 1.12 (d, J = 6.0 Hz, 3H), 1.04-0.95 (m, 1H) |
| 39 | 21 | 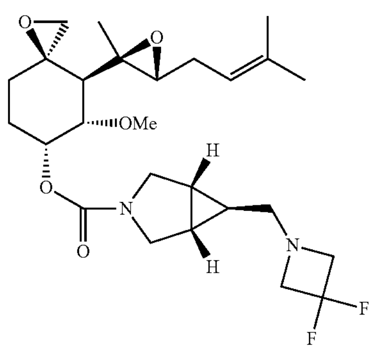 [SMILES: CO[C@@H]1[C@H](OC(=O)N2C[C@@H]3[C@@H](CN4CC(F)(F)C4)[C@@H]3C2)CC[C@]2(CO2)[C@H]1[C@@]1(C)O[C@@H]1CC=C(C)C] | 497 [M + H]⁺ | 5.46(s, 1H), 5.14 (t, J = 7.5 Hz, 1H), 3.95-3.22 (m, 12H), 2.92 (d, J = 4.3 Hz, 1H), 2.69-2.34 (m, 4H), 2.28 (dd, J = 14.3, 7.0 Hz, 1H), 2.09 (dt, J = 14.6, 7.2 Hz, 1H), 2.03-1.91 (m, 1H), 1.86 (d, J = 14.8 Hz, 1H), 1.81-1.71 (m, 3H), 1.68 (s, 3H), 1.59 (s, 3H), 1.40 (d, J = 27.9 Hz, 2H), 1.12(d, J = 6.1 Hz, 3H), 1.09-0.95 (m, 1H), 0.68-0.62(m,1H) |
| 40 | 22 | 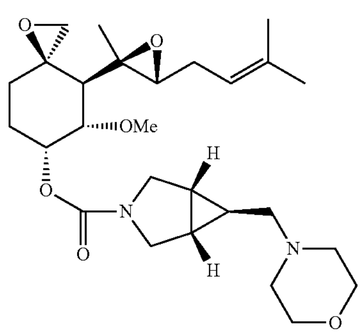 [SMILES: CO[C@@H]1[C@H](OC(=O)N2C[C@@H]3[C@@H](CN4CCOCC4)[C@@H]3C2)CC[C@]2(CO2)[C@H]1[C@@]1(C)O[C@@H]1CC=C(C)C] | 491 [M + H]⁺ | 5.45 (d, J = 10.1 Hz, 1H), 5.18-5.09 (m, 1H), 3.71 (d, J = 18.5 Hz, 1H), 3.39-3.24 (m, 5H), 2.91 (d, J = 4.3 Hz, 1H), 2.69-2.34 (m, 6H), 2.28 (dt, J = 13.0, 6.5 Hz, 3H), 2.08 (dt, J = 22.2, 7.4 Hz, 1H), 2.02-1.72 (m, 5H), 1.68 (s, 3H), 1.59 (s, 3H), 1.13 (s, 3H), 1.00 (dd, J = 13.5, 2.4 Hz, 1H), 0.81-0.63 (m, 1H) |

-continued

| Example | Intermediate | Structure | LC-MS | H-NMR (400 MHz, CDCl$_3$) |
|---|---|---|---|---|
| 41 | 23 | 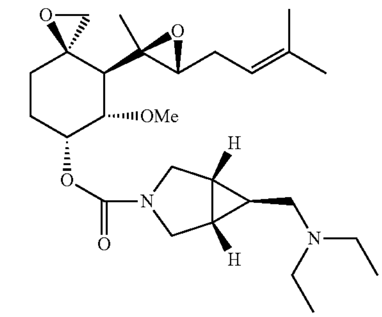 [SMILES: CCN(CC)C[C@@H]1[C@H]2CN(C(=O)O[C@@H]3CC[C@]4(CO4)[C@@H]([C@@]4(C)O[C@@H]4CC=C(C)C)[C@@H]3OC)C[C@@H]12] | 477 [M + H]$^+$ | 5.45 (d, J = 8.0 Hz, 1H), 5.18-5.10 (m, 1H), 3.57 (dd, J = 11.1, 3.1 Hz, 2H), 3.44 (s, 1H), 3.40-3.31 (m, 4H), 2.91 (d, J = 4.3 Hz, 1H), 2.69-2.24 (m, 9H), 2.15-1.71 (m, 6H), 1.68 (s, 3H), 1.59 (s, 3H), 1.35 (d, J = 28.5 Hz, 2H), 1.13 (d, J = 1.4 Hz, 3H), 1.01 (dt, J = 23.6, 7.0 Hz, 7H), 0.72 (ddd, J = 40.2, 6.7, 3.3 Hz, 1H) |
| 42 | 24 | 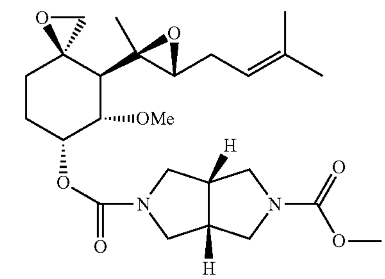 [SMILES: COC(=O)N1C[C@@H]2CN(C(=O)O[C@@H]3CC[C@]4(CO4)[C@@H]([C@@]4(C)O[C@@H]4CC=C(C)C)[C@@H]3OC)C[C@@H]2C1] | 479 [M + H]$^+$ | 5.50 (s, 1H), 5.14 (t, J = 7.5 Hz, 1H), 3.64-3.62 (m, 4H), 3.58-3.54 (m, 4H), 3.39 (s, 3H), 3.26-3.21 (m, 4H), 2.92 (d, J = 4.3 Hz, 1H), 2.81 (s, 2H), 2.51-2.47 (m, 2H), 2.38-2.21 (m, 1H), 2.14-2.04 (m, 1H), 2.03-1.84 (m, 2H), 1.80-1.79 (m, 3H), 1.68 (s, 3H), 1.59 (s, 3H), 1.13 (s, 3H), 1.02 (d, J = 12.6 Hz, 1H) |
| 43 | 25 | 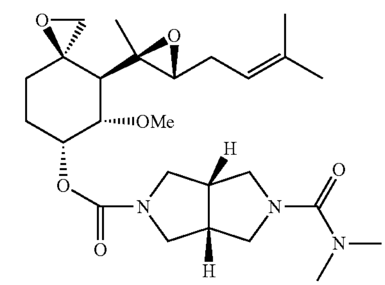 | 492 [M + H]$^+$ | 5.50 (s, 1H), 5.14 (m, 1H), 3.65-3.48 (m, 5H), 3.39 (s, 3H), 3.28-3.07 (m, 4H), 2.92 (d, J = 4.3 Hz, 1H), 2.77 (d, J = 8.9 Hz, 8H), 2.49 (m, 2H), 2.33-2.25 (m, 1H), 2.09 (m, 1H), 2.02-1.96 (m, 1H), 1.90 m, 1H), 1.79 (m, 2H), 1.67 (s, 3H), 1.59 (s, 3H), 1.14 (s, 3H), 1.01 (d, J = 13.5 Hz, 1H) |
| 44 | 26 | 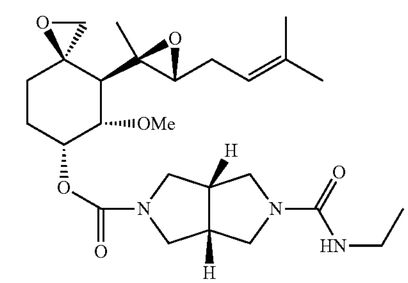 [SMILES: CCNC(=O)N1C[C@@H]2CN(C(=O)O[C@@H]3CC[C@]4(CO4)[C@@H]([C@@]4(C)O[C@@H]4CC=C(C)C)[C@@H]3OC)C[C@@H]2C1] | 492 [M + H]$^+$ | 5.50 (s, 1H), 5.14 (m, 1H), 4.05 (m, 1H), 3.50 (m, 4H), 3.38 (m, 3H), 3.34-3.07 (m, 6H), 2.92 (d, J = 4.1 Hz, 1H), 2.85 (s, 2H), 2.51-2.47 (m, 1H), 2.35-2.22 (m, 1H), 2.15-1.94 (m, 3H), 1.89 (d, J = 12.3 Hz, 1H), 1.82-1.72 (m, 2H), 1.68 (s, 3H), 1.59 (s, 4H), 1.12 (s, 3H), 1.08 (m, 3H), 1.01 (d, J = 13.5 Hz, 1H) |
| 45 | 27 | 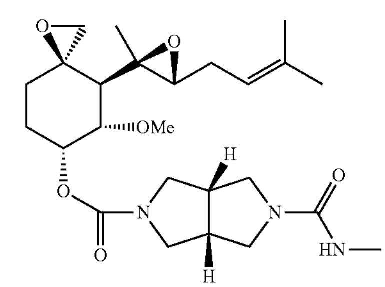 [SMILES: CNC(=O)N1C[C@@H]2CN(C(=O)O[C@@H]3CC[C@]4(CO4)[C@@H]([C@@]4(C)O[C@@H]4CC=C(C)C)[C@@H]3OC)C[C@@H]2C1] | 478 [M + H]$^+$ | 5.49 (s, 1H), 5.14 (m, 1H), 4.10 (s, 1H), 3.71-3.41 (m, 5H), 3.37 (m, 3H), 3.26 (m, 3H), 3.16-3.06 (m, 1H), 2.92 (d, J = 4.3 Hz, 1H), 2.89-2.78 (m, 2H), 2.74 (s, 3H), 2.49 (m, 2H), 2.34-2.24 (m, 1H), 2.09 (m, 1H), 1.99 (m, 1H), 1.89 (dd, J = 14.2, 2.1 Hz, 1H), 1.83-1.74 (m, 2H), 1.68 (s, 3H), 1.59 (s, 3H), 1.12 (s, 3H), 1.01 (d, J = 11.5 Hz, 1H) |

| Example | Intermediate | Structure | LC-MS | H-NMR (400 MHz, CDCl$_3$) |
|---|---|---|---|---|
| 46 | 28 | 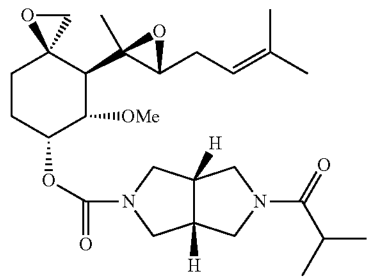 [SMILES: CO[C@@H]1[C@H](OC(=O)N2C[C@@H]3CN(C(=O)C(C)C)C[C@@H]3C2)CC[C@]2(CO2)[C@H]1[C@@]1(C)O[C@@H]1CC=C(C)C] | 491 [M + H]$^+$ | 5.50 (s, 1H), 5.18-5.08 (m, 1H), 3.75-3.52 (m, 5H), 3.40 (d, J = 8.1 Hz, 3H), 3.37 (d, J = 7.3 Hz, 1H), 3.31 (ddd, J = 17.2, 10.4, 4.2 Hz, 2H), 3.22-3.04 (m, 1H), 2.97-2.74 (m, 3H), 2.62-2.52 (m, 1H), 2.51-2.45 (m, 2H), 2.33-2.24 (m, 1H), 2.16-2.05 (m, 1H), 1.99 (td, J = 13.8, 4.2 Hz, 1H), 1.88 (d, J = 13.9 Hz, 1H), 1.79 (d, J = 11.3 Hz, 2H), 1.68 (s, 4H), 1.59 (s, 3H), 1.14 (s, 3H), 1.05 (dd, J = 6.6, 3.3 Hz, 6H) |
| 47 | 29 | 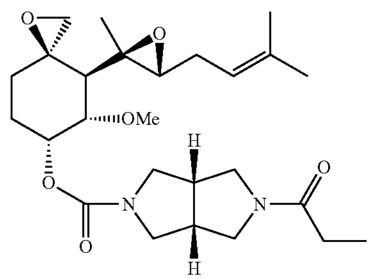 [SMILES: CCC(=O)N1C[C@@H]2CN(C(=O)O[C@@H]3CC[C@]4(CO4)[C@@H]([C@@]4(C)O[C@@H]4CC=C(C)C)[C@@H]3OC)C[C@@H]2C1] | 477 [M + H]$^+$ | 5.48 (d, J = 15.7 Hz, 1H), 5.14 (t, J = 7.4 Hz, 1H), 3.72-3.53 (m, 5H), 3.39 (s, 3H), 3.38 (s, 1H), 3.30-3.23 (m, 2H), 3.13 (ddd, J = 27.4, 13.6, 8.1 Hz, 1H), 2.92 (d, J = 4.1 Hz, 1H), 2.81 (d, J = 5.3 Hz, 2H), 2.53-2.44 (m, 2H), 2.33-2.25 (m, 1H), 2.24-2.15 (m, 2H), 2.15-2.05 (m, 1H), 2.03-1.94 (m, 1H), 1.90 (s, 1H), 1.79 (d, J = 11.4 Hz, 2H), 1.68 (s, 3H), 1.59 (s, 3H), 1.18 (s, 1H), 1.14 (s, 3H), 1.09 (dd, J = 13.1, 5.7 Hz, 3H) |
| 48 | 30 | 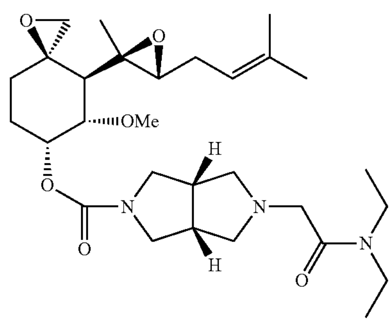 [SMILES: CCN(CC)C(=O)CN1C[C@@H]2CN(C(=O)O[C@@H]3CC[C@]4(CO4)[C@@H]([C@@]4(C)O[C@@H]4CC=C(C)C)[C@@H]3OC)C[C@@H]2C1] | 534 [M + H]$^+$ | 5.48 (s, 1H), 5.14 (s, 1H), 3.75-3.08 (m, 14H), 2.92-2.82 (m, 3H), 2.74-2.40 (m, 5H), 2.31-2.25 (m, 1H), 2.17-1.94 (m, 3H), 1.93-1.73 (m, 5H), 1.68 (s, 3H), 1.27-0.97 (m, 10H), 0.80 (d, J = 7.0 Hz, 1H) |
| 49 | 31 | 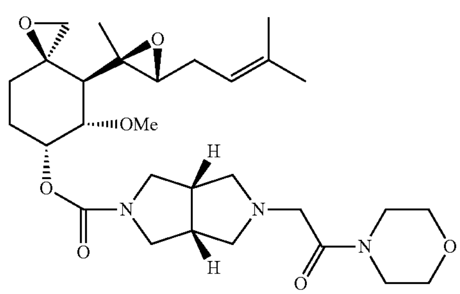 [SMILES: CO[C@@H]1[C@H](OC(=O)N2C[C@H]3CN(CC(=O)N4CCOCC4)C[C@H]3C2)CC[C@]2(CO2)[C@H]1[C@@]1(C)O[C@@H]1CC=C(C)C] | 548 [M + H]$^+$ | 5.49 (s, 1H), 5.13 (s, 1H), 3.76-3.26 (m, 17H), 3.28-3.03 (m, 2H), 2.92-2.68 (m, 3H), 2.62-2.47 (m, 4H), 2.30-2.25 (m, 1H), 2.17-1.95 (m, 3H), 1.91-1.78 (m, 3H), 1.68 (s, 3H), 1.59 (s, 3H), 1.19 (m, 5H), 1.01 (d, J = 13.6 Hz, 1H), 0.81 (t, J = 6.8 Hz, 1H) |
| 50 | 32 | 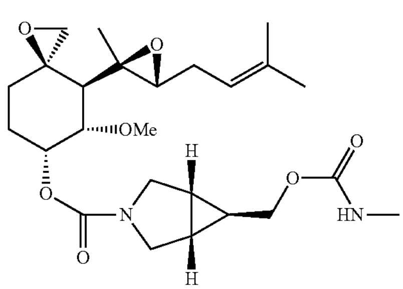 [SMILES: CNC(=O)OC[C@@H]1[C@H]2CN(C(=O)O[C@@H]3CC[C@]4(CO4)[C@@H]([C@@]4(C)O[C@@H]4CC=C(C)C)[C@@H]3OC)C[C@@H]12] | 479 [M + H]$^+$ | 5.42-5.46 (m, 1H), 5.12-5.16 (m, 1H), 4.53-4.62 (m, 1H), 3.82-3.95 (m, 2H), 3.53-3.60 (m, 2H), 3.23-3.44 (m, 6H), 2.91 (d, J = 4.8 Hz, 1H), 2.72-2.74 (m, 3H), 2.46-2.52 (m, 2H), 2.28-2.32 (m, 1H), 2.06-2.12 (m, 1H), 1.79-2.01 (m, 4H), 1.75 (s, 3H), 1.60 (s, 3H), 1.40-1.45 (m, 2H), 1.19 (s, 3H), 0.85-0.95 (m, 2H) |

| Example | Intermediate | Structure | LC-MS | H-NMR (400 MHz, CDCl$_3$) |
|---|---|---|---|---|
| 51 | 33 | 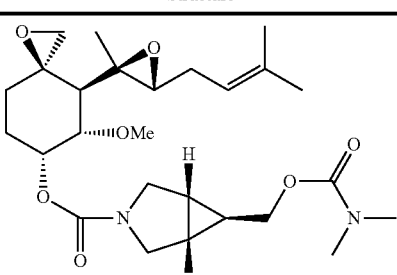 | 493 [M + H]$^+$ | 5.42-5.47 (m, 1H), 5.12-5.16 (m, 1H), 3.92-3.97 (m, 1H), 3.79-3.85 (m, 1H), 3.51-3.62 (m, 2H), 3.41-3.44 (m, 1H), 3.29-3.37 (m, 5H), 2.90 (d, J = 4.4 Hz, 1H), 2.84-2.86 (m, 6H), 2.46-2.51 (m, 2H), 2.26-2.28 (m, 1H), 1.71-2.15 (m, 5H), 1.68 (s, 3H), 1.61 (s, 3H), 1.41-1.47 (m, 2H), 1.14-1.18 (m, 3H), 0.91-1.05 (m, 2H) |
| 52 | 34 | 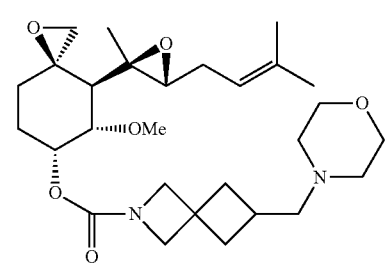 [SMILES: CO[C@@H]1[C@H](OC(=O)N2CC3(CC(CN4CCOCC4)C3)C2)CC[C@]2(CO2)[C@H]1[C@@]1(C)O[C@@H]1CC=C(C)C] | 505 [M + H]$^+$ | 5.42 (d, J = 3.0 Hz, 1H), 5.20-5.10 (m, 1H), 4.17-3.65 (m, 8H), 3.53 (m, 1H), 3.37 (s, 3H), 2.91 (d, J = 4.3 Hz, 1H), 2.53-2.23 (m, 11H), 2.09 (m, 1H), 2.02-1.93 (m, 1H), 1.89-1.70 (m, 6H), 1.68 (s, 3H), 1.59 (s, 3H), 1.12 (s, 3H), 0.99 (m, 1H) |
Following the above procedures, the following compounds are prepared:
| Example | Structure |
|---|---|
| 53 | 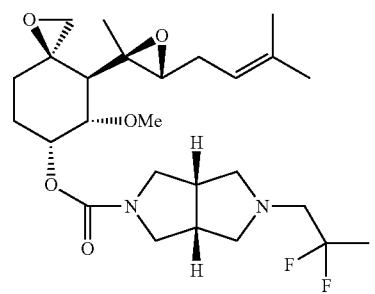 [SMILES: CO[C@@H]1[C@H](OC(=O)N2C[C@H]3CN(CC(C)(F)F)C[C@H]3C2)CC[C@]2(CO2)[C@H]1[C@@]1(C)O[C@@H]1CC=C(C)C] |
| 54 | 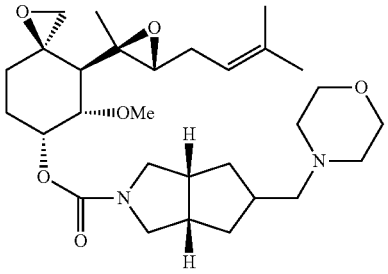 [SMILES: CO[C@@H]1[C@H](OC(=O)N2C[C@H]3CC(CN4CCOCC4)C[C@H]3C2)CC[C@]2(CO2)[C@H]1[C@@]1(C)O[C@@H]1CC=C(C)C] |
| 55 | 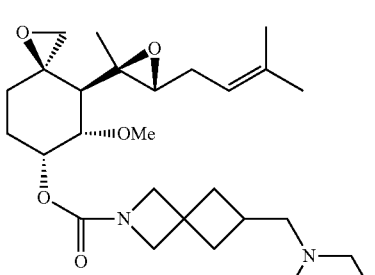 |
| 56 | 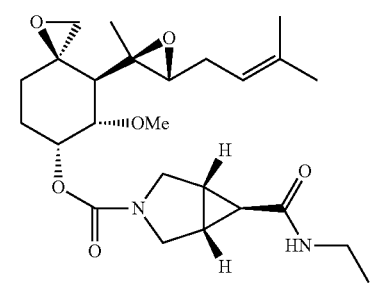 [SMILES: CCNC(=O)[C@H]1[C@@H]2CN(C(=O)O[C@@H]3CC[C@]4(CO4)[C@@H]([C@@]4(C)O[C@@H]4CC=C(C)C)[C@@H]3OC)C[C@@H]21] |
| 57 | 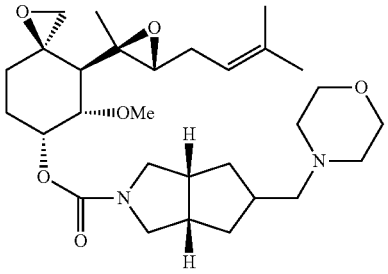 [SMILES: CO[C@@H]1[C@H](OC(=O)N2C[C@H]3CC(CN4CCOCC4)C[C@H]3C2)CC[C@]2(CO2)[C@H]1[C@@]1(C)O[C@@H]1CC=C(C)C] |

-continued

| Example | Structure |
|---------|-----------|
| 58 | 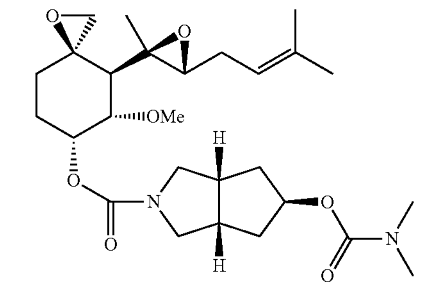 [SMILES: CO[C@@H]1[C@H](OC(=O)N2C[C@H]3C[C@H](OC(=O)N(C)C)C[C@H]3C2)CC[C@]2(CO2)[C@H]1[C@@]1(C)O[C@@H]1CC=C(C)C] |
| 59 | 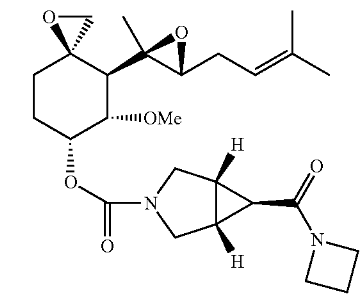 [SMILES: CO[C@@H]1[C@H](OC(=O)N2C[C@@H]3[C@H](C2)[C@H]3C(=O)N2CCC2)CC[C@]2(CO2)[C@H]1[C@@]1(C)O[C@@H]1CC=C(C)C] |
| 60 | 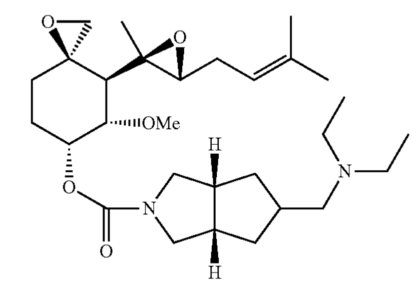 [SMILES: CCN(CC)CC1C[C@@H]2CN(C(=O)O[C@@H]3CC[C@]4(CO4)[C@@H]([C@@]4(C)O[C@@H]4CC=C(C)C)[C@@H]3OC)C[C@@H]2C1] |
| 61 | 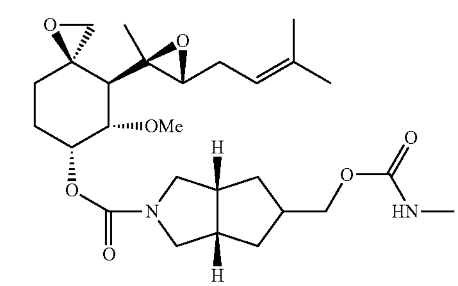 [SMILES: CNC(=O)OCC1C[C@@H]2CN(C(=O)O[C@@H]3CC[C@]4(CO4)[C@@H]([C@@]4(C)O[C@@H]4CC=C(C)C)[C@@H]3OC)C[C@@H]2C1] |

Biological Example A

Compounds are tested for their capacity to inhibit recombinant human MetAP2 activity using the following assay.

Flag tagged Human recombinant MetAP2 expressed and isolated for use as the enzyme source. 10 mM stock solutions of compounds were prepared in 100% DMSO and further diluted in 100% DMSO required concentration to 1 mM stocks. The stock compound solutions and DMSO vehicle controls were diluted to target final compound concentrations using assay buffer to a final concentration of 50 mM HEPES containing 100 mM NaCl, pH adjusted to 7.5. The MAS peptide was formulated to a 7.5 mM stock in distilled water and prior to use further diluted 1:4. Amino acid oxidase was prepared as a stock solution (6.2 mg/ml) and prior to use further diluted 1:49.6 in distilled water. A 250 µM solution of $MnCl_2$ was prepared in advance of thawing an aliquot of MetAP2 enzyme. 40 µl of enzyme was mixed with 100 µl of $MnCl_2$ then further diluted in assay buffer to a final concentration of 16 µg/ml. To test for compound effect on MetAP2 enzyme activity, 5 µl of test compound, 10 µl of MAS substrate/amino acid oxidase mixture, 10 µl of MetAP2 was added to test wells in a 384 well black plate with blank wells containing no enzyme, replaced with 10 µl of assay buffer. All compounds were tested in duplicate on two occasions on the same day. The final in well concentrations of the assay were: 1% DMSO, 0.272 µg/ml MetAP2, 10M MnCl2, 50.0 µg/ml (0.225 U/ml) amino acid oxidase, and 0.0.75 mM MAS.

The plate was sealed with a TopSeal A cover and mixed briefly on an orbital mixer at 900 rpm. The plate was incubated for a further 25 minutes at 25° C. A 5× stock of Amplex buffer was prepared (0.25M sodium phosphate, pH 7.4) and stored at 4° C. When preparing for use the stock was diluted with distilled water. Amplex Ultraread stock solution was prepared at 2.57 mg/ml in 100% DMSO and stored in 50 µl aliquots at −20° C. 20 µl of 505 U/ml. Horse radish peroxidase was diluted in 990 ml of Amplex buffer, 100 µl of this was combined with 50 µl of Amplex Ultrared in 4850 ml of 1× Amplex buffer to generate sufficient detection reagent for a 384 well plate. 25 µl detection reagent was added to each well of the test plate, which was re-sealed and mixed briefly on an orbital shaker. The plate was transferred to an Envision Multi-label reader and RFU measured corresponding to excitation 531 nm and emission 595 nm. At the end of the MetAP2 incubation 25 µl Amplex/HRP mixture per well was added and the plate read plate on a plate reader.

The $IC_{50}$ is defined as the concentration at which a given compound achieves 50% inhibition of control.

Compounds of the disclosure demonstrated activity in the assay of this Example as indicated in the following tables, wherein A represents an $IC_{50}$ of <0.05 µM and B represents an $IC_{50}$ between 0.05 µM and 0.5 µM.

TABLE 1

| Example No. | Compound Name | MetAP2 $IC_{50}$ (µM) |
|---|---|---|
| 1 | (3R,4S,5S,6R)-5-methoxy-4-((2R,3R)-2-methyl-3-(3-methylbut-2-enyl)oxiran-2-yl)-1-oxaspiro[2.5]octan-6-yl 3-oxa-9-azaspiro[5.5]undecane-9-carboxylate | B |
| 2 | (3R,4S,5S,6R)-5-methoxy-4-((2R,3R)-2-methyl-3-(3-methylbut-2-enyl)oxiran-2-yl)-1-oxaspiro[2.5]octan-6-yl 2-oxa-6-azaspiro[3.3]heptane-6-carboxylate | A |
| 8 | (3R,4S,5S,6R)-5-methoxy-4-((2R,3R)-2-methyl-3-(3-methylbut-2-enyl)oxiran-2-yl)-1-oxaspiro[2.5]octan-6-yl 7-methyl-2,7-diazaspiro[3.5]nonane-2-carboxylate formate | A |

TABLE 1-continued

| Example No. | Compound Name | MetAP2 IC$_{50}$ (μM) |
|---|---|---|
| 11 | (3R,4S,5S,6R)-5-methoxy-4-((2R,3R)-2-methyl-3-(3-methylbut-2-enyl)oxiran-2-yl)-1-oxaspiro[2.5]octan-6-yl 6-methyl-6-azaspiro[3.4]octan-2-ylcarbamate formate | A |
| 10 | (3R,4S,5S,6R)-5-methoxy-4-((2R,3R)-2-methyl-3-(3-methylbut-2-enyl)oxiran-2-yl)-1-oxaspiro[2.5]octan-6-yl 2-methyl-2-azaspiro[3.3]heptan-6-ylcarbamate formate | A |
| 7 | (3R,4S,5S,6R)-5-methoxy-4-((2R,3R)-2-methyl-3-(3-methylbut-2-enyl)oxiran-2-yl)-1-oxaspiro[2.5]octan-6-yl 7-methyl-7-azaspiro[3.5]nonan-2-ylcarbamate formate | A |
| 20 | (3aR,6aS)-((3R,4S,5S,6R)-5-methoxy-4-((2R,3R)-2-methyl-3-(3-methylbut-2-enyl)oxiran-2-yl)-1-oxaspiro[2.5]octan-6-yl) 5-methylhexahydropyrrolo[3,4-c]pyrrole-2(1H)-carboxylate formate | A |
| 26 | (3R,4S,5S,6R)-5-methoxy-4-((2R,3R)-2-methyl-3-(3-methylbut-2-enyl)oxiran-2-yl)-1-oxaspiro[2.5]octan-6-yl 8-methyl-2,8-diazaspiro[4.5]decane-2-carboxylate | A |
| 12 | (3R,4S,5S,6R)-5-methoxy-4-((2R,3R)-2-methyl-3-(3-methylbut-2-enyl)oxiran-2-yl)-1-oxaspiro[2.5]octan-6-yl 6-methyl-2,6-diazaspiro[3.3]heptane-2-carboxylate | A |
| 22 | (3R,4S,5S,6R)-5-methoxy-4-((2R,3R)-2-methyl-3-(3-methylbut-2-enyl)oxiran-2-yl)-1-oxaspiro[2.5]octan-6-yl 6,6-difluoro-3-azabicyclo[3.1.0]hexane-3-carboxylate | A |
| 23 | (3R,4S,5S,6R)-5-methoxy-4-((2R,3R)-2-methyl-3-(3-methylbut-2-enyl)oxiran-2-yl)-1-oxaspiro[2.5]octan-6-yl 2-thia-6-azaspiro[3.3]heptane 2,2-dioxide-6-carboxylate | B |
| 27 | (3R,4S,5S,6R)-5-methoxy-4-((2R,3R)-2-methyl-3-(3-methylbut-2-enyl)oxiran-2-yl)-1-oxaspiro[2.5]octan-6-yl 8-oxa-2-azaspiro[4.5]decane-2-carboxylate | B |
| 9 | (3R,4S,5S,6R)-5-methoxy-4-((2R,3R)-2-methyl-3-(3-methylbut-2-enyl)oxiran-2-yl)-1-oxaspiro[2.5]octan-6-yl 7-(2,2-difluoroethyl)-2,7-diazaspiro[3.5]nonane-2-carboxylate formate | B |
| 4 | (3R,4S,5S,6R)-5-methoxy-4-((2R,3R)-2-methyl-3-(3-methylbut-2-enyl)oxiran-2-yl)-1-oxaspiro[2.5]octan-6-yl 6-oxa-2-azaspiro[3.4]octane-2-carboxylate formate | A |
| 5 | (3R,4S,5S,6R)-5-methoxy-4-((2R,3R)-2-methyl-3-(3-methylbut-2-enyl)oxiran-2-yl)-1-oxaspiro[2.5]octan-6-yl 2-oxa-7-azaspiro[3.5]nonane-7-carboxylate | A |
| 3 | (3R,4S,5S,6R)-5-methoxy-4-((2R,3R)-2-methyl-3-(3-methylbut-2-enyl)oxiran-2-yl)-1-oxaspiro[2.5]octan-6-yl 7-oxa-2-azaspiro[3.5]nonane-2-carboxylate | A |
| 24 | (3R,4S,5S,6R)-5-methoxy-4-((2R,3R)-2-methyl-3-(3-methylbut-2-enyl)oxiran-2-yl)-1-oxaspiro[2.5]octan-6-yl 2-oxa-8-azaspiro[4.5]decane-8-carboxylate | B |
| 6 | (3R,4S,5S,6R)-5-methoxy-4-((2R,3R)-2-methyl-3-(3-methylbut-2-enyl)oxiran-2-yl)-1-oxaspiro[2.5]octan-6-yl 6-oxa-2-azaspiro[3.4]octane-2-carboxylate | A |
| 19 | (3aR,6aS)-((3R,4S,5S,6R)-5-methoxy-4-((2R,3R)-2-methyl-3-(3-methylbut-2-enyl)oxiran-2-yl)-1-oxaspiro[2.5]octan-6-yl) 5-(2,2-difluoroethyl)hexahydropyrrolo[3,4-c]pyrrole-2(1H)-carboxylate | B |
| 32 | (1R,5S,6R)-(3R,4S,5S,6R)-5-methoxy-4-((2R,3R)-2-methyl-3-(3-methylbut-2-en-1-yl)oxiran-2-yl)-1-oxaspiro[2.5]octan-6-yl 6-(methylcarbamoyl)-3-azabicyclo[3.1.0]hexane-3-carboxylate | B |
| 33 | (1R,5S,6R)-(3R,4S,5S,6R)-5-methoxy-4-((2R,3R)-2-methyl-3-(3-methylbut-2-en-1-yl)oxiran-2-yl)-1-oxaspiro[2.5]octan-6-yl 6-(dimethylcarbamoyl)-3-azabicyclo[3.1.0]hexane-3-carboxylate | B |
| 34 | (1R,5S,6R)-(3R,4S,5S,6R)-5-methoxy-4-((2R,3R)-2-methyl-3-(3-methylbut-2-en-1-yl)oxiran-2-yl)-1-oxaspiro[2.5]octan-6-yl 6-carbamoyl-3-azabicyclo[3.1.0]hexane-3-carboxylate | A |
| 25 | (3R,4S,5S,6R)-5-methoxy-4-((2R,3R)-2-methyl-3-(3-methylbut-2-enyl)oxiran-2-yl)-1-oxaspiro[2.5]octan-6-yl 7-oxo-2,6-diazaspiro[3.4]octane-2-carboxylate | A |
| compound A | [(3R,6R,7S,8S)-7-methoxy-8-[(2R,3R)-2-methyl-3-(3-methylbut-2-enyl)oxiran-2-yl]-2-oxaspiro[2.5]octan-6-yl] (E)-3-[4-[2-(dimethylamino)ethoxy]phenyl]prop-2-enoate | B |

Biological Example B

Study Summary Mouse DIO:

The objective of this study design was to investigate the efficacy of disclosed compounds in a 10 day DIO mouse model. Effects on body weight, food intake, hematology and blood chemistry were the primary readouts of this study design. Male, Diet Induced Obese (DIO) C57BL/6 mice, 19-21 weeks of age (13-15 weeks on high fat diet) were ordered from a certified vendor and upon receipt were housed on irradiated corncob bedding in micro-isolator cages on a 12-hour light-dark cycle (0700-1900) at 68-74° F. and 30-70% humidity. Mice were fed Research Diets D12492 (60% Kcal fat, 20% Kcal carbohydrate and 20% protein) and provided water ad libitum. DIO mice were received and housed in the facility for approximately two weeks prior to the start of test article administration. On Day −4 or −3, mice were randomized into study groups based on body weight and body weights were continued to be recorded daily for the duration of the study. Daily food intake was assessed starting on Study Day −2 by weighing of the food with hopper together to avoid loss of food in transfer.

Compounds were formulated into a 100% DMSO stock (at 9 mg/mL) prior to the start, and further diluted into the target working concentration using the vehicle of 10% DMSO in water. Prior to test article administration, starting on Day −3 a dosing acclimation occured with all animals receiving a subcutaneous injection of vehicle (10% DMSO) only for 3 days. Starting on Day 1, test compounds or vehicle were administered based on individual body weight, subcutaneously, once a day for 10 days. All mice were sacrificed on Day 11, 24 hours following the final dosing on Day 10. After sacrifice, whole blood was collected and analyzed for hematology and blood chemistry parameters.

Study Summary Rat DIO:

The objective of this study design is to investigate the efficacy of disclosed compounds in an 11 day rat DIO model used to screen compounds for pharmacologic efficacy on endpoints related to obesity and metabolism. Effects on body weight, food intake, hematology and blood chemistries were the primary readouts of this study design. Male Sprague Dawley rats, approximately 8 weeks of age, were ordered from a certified vendor and housed on irradiated corncob bedding in micro-isolator cages, on a 12-hour light-dark cycle (0700-1900) at 68-74° F. and 30-70% humidity. Rats were fed Research Diets D12451 (45% High Fat) and provided water ad libitum. Rats were received and housed in the facility for at least two or three weeks prior to start of test article administration. On Day −4 or −3, rats were randomized into study groups based on body weight and body weights were continued to be recorded daily for the duration of the study. Daily food intake was assessed starting on Study Day −2 by weighing the hopper including the food to avoid loss of food in transfer.

Compounds were formulated into a 100% DMSO stock (at 9 mg/mL) prior to the start, and further diluted into the target working concentration using the vehicle of 10% DMSO in water. Prior to test article administration, starting on Day −3 a dosing acclimation occured with all animals receiving a subcutaneous injection of vehicle (10% DMSO) only for 3 days. Starting on Day 1, test compounds or vehicle were administered based on individual body weight, subcutaneously, once a day for 11 days. All animals were sacrificed on Day 11, approximately 2 hours following the final dosing on Day 11. After sacrifice, whole blood was collected and analyzed for hematology and blood chemistry parameters.

Compounds were tested for weight loss vs. vehicle at 0.3 and 1.0 mpk sc (mg per kg animal weight delivered subcutaneously), and the results are shown in Table 2 below.

TABLE 2

| Example No. | Compound Name | Mouse @ 0.3 mpk sc (%) | Rat @ 0.3 mpk sc (%) | Rat @ 1.0 mpk sc (%) |
|---|---|---|---|---|
| 1 | (3R,4S,5S,6R)-5-methoxy-4-((2R,3R)-2-methyl-3-(3-methylbut-2-enyl)oxiran-2-yl)-1-oxaspiro[2.5]octan-6-yl 3-oxa-9-azaspiro[5.5]undecane-9-carboxylate | 17 | 10.3 | 16.3 |
| 2 | (3R,4S,5S,6R)-5-methoxy-4-((2R,3R)-2-methyl-3-(3-methylbut-2-enyl)oxiran-2-yl)-1-oxaspiro[2.5]octan-6-yl 2-oxa-6-azaspiro[3.3]heptane-6-carboxylate | 11.1 | 8 | 10.2 |
| 8 | (3R,4S,5S,6R)-5-methoxy-4-((2R,3R)-2-methyl-3-(3-methylbut-2-enyl)oxiran-2-yl)-1-oxaspiro[2.5]octan-6-yl 7-methyl-2,7-diazaspiro[3.5]nonane-2-carboxylate formate | 6.2 | | |
| 11 | (3R,4S,5S,6R)-5-methoxy-4-((2R,3R)-2-methyl-3-(3-methylbut-2-enyl)oxiran-2-yl)-1-oxaspiro[2.5]octan-6-yl 6-methyl-6-azaspiro[3.4]octan-2-ylcarbamate formate | 6 | | |
| 10 | (3R,4S,5S,6R)-5-methoxy-4-((2R,3R)-2-methyl-3-(3-methylbut-2-enyl)oxiran-2-yl)-1-oxaspiro[2.5]octan-6-yl 2-methyl-2-azaspiro[3.3]heptan-6-ylcarbamate formate | 8.4 | 2 | 7.2 |
| 7 | (3R,4S,5S,6R)-5-methoxy-4-((2R,3R)-2-methyl-3-(3-methylbut-2-enyl)oxiran-2-yl)-1-oxaspiro[2.5]octan-6-yl 7-methyl-7-azaspiro[3.5]nonan-2-ylcarbamate formate | 1.9 | | |
| 20 | (3aR,6aS)-((3R,4S,5S,6R)-5-methoxy-4-((2R,3R)-2-methyl-3-(3-methylbut-2-enyl)oxiran-2-yl)-1-oxaspiro[2.5]octan-6-yl) 5-methylhexahydropyrrolo[3,4-c]pyrrole-2(1H)-carboxylate formate | 1.4 | | |
| 26 | (3R,4S,5S,6R)-5-methoxy-4-((2R,3R)-2-methyl-3-(3-methylbut-2-enyl)oxiran-2-yl)-1-oxaspiro[2.5]octan-6-yl 8-methyl-2,8-diazaspiro[4.5]decane-2-carboxylate | 5.6 | | |
| 12 | (3R,4S,5S,6R)-5-methoxy-4-((2R,3R)-2-methyl-3-(3-methylbut-2-enyl)oxiran-2-yl)-1-oxaspiro[2.5]octan-6-yl 6-methyl-2,6-diazaspiro[3.3]heptane-2-carboxylate | 1.8 | | |
| 22 | (3R,4S,5S,6R)-5-methoxy-4-((2R,3R)-2-methyl-3-(3-methylbut-2-enyl)oxiran-2-yl)-1-oxaspiro[2.5]octan-6-yl 6,6-difluoro-3-azabicyclo[3.1.0]hexane-3-carboxylate | 15.5 | | |

TABLE 2-continued

| Example No. | Compound Name | Mouse @ 0.3 mpk sc (%) | Rat @ 0.3 mpk sc (%) | Rat @ 1.0 mpk sc (%) |
|---|---|---|---|---|
| 23 | (3R,4S,5S,6R)-5-methoxy-4-((2R,3R)-2-methyl-3-(3-methylbut-2-enyl)oxiran-2-yl)-1-oxaspiro[2.5]octan-6-yl 2-thia-6-azaspiro[3.3]heptane 2,2-dioxide-6-carboxylate | 2 | | |
| 27 | (3R,4S,5S,6R)-5-methoxy-4-((2R,3R)-2-methyl-3-(3-methylbut-2-enyl)oxiran-2-yl)-1-oxaspiro[2.5]octan-6-yl 8-oxa-2-azaspiro[4.5]decane-2-carboxylate | 16.3 | | |
| 9 | (3R,4S,5S,6R)-5-methoxy-4-((2R,3R)-2-methyl-3-(3-methylbut-2-enyl)oxiran-2-yl)-1-oxaspiro[2.5]octan-6-yl 7-(2,2-difluoroethyl)-2,7-diazaspiro[3.5]nonane-2-carboxylate formate | 21.5 | | |
| 4 | (3R,4S,5S,6R)-5-methoxy-4-((2R,3R)-2-methyl-3-(3-methylbut-2-enyl)oxiran-2-yl)-1-oxaspiro[2.5]octan-6-yl 6-oxa-2-azaspiro[3.4]octane-2-carboxylate formate | 15.4 | | |
| 5 | (3R,4S,5S,6R)-5-methoxy-4-((2R,3R)-2-methyl-3-(3-methylbut-2-enyl)oxiran-2-yl)-1-oxaspiro[2.5]octan-6-yl 2-oxa-7-azaspiro[3.5]nonane-7-carboxylate | 16.7 | 6.6 | |
| 3 | (3R,4S,5S,6R)-5-methoxy-4-((2R,3R)-2-methyl-3-(3-methylbut-2-enyl)oxiran-2-yl)-1-oxaspiro[2.5]octan-6-yl 7-oxa-2-azaspiro[3.5]nonane-2-carboxylate | 18.9 | 7.9 | |
| 13 | (3aR,6aS)-((3R,4S,5S,6R)-5-methoxy-4-((2R,3R)-2-methyl-3-(3-methylbut-2-enyl)oxiran-2-yl)-1-oxaspiro[2.5]octan-6-yl) tetrahydro-1H-furo[3,4-c]pyrrole-5(3H)-carboxylate | 16.9 | 3.1 | |
| 24 | (3R,4S,5S,6R)-5-methoxy-4-((2R,3R)-2-methyl-3-(3-methylbut-2-enyl)oxiran-2-yl)-1-oxaspiro[2.5]octan-6-yl 2-oxa-8-azaspiro[4.5]decane-8-carboxylate | 20.5 | 6.3 | |
| 6 | (3R,4S,5S,6R)-5-methoxy-4-((2R,3R)-2-methyl-3-(3-methylbut-2-enyl)oxiran-2-yl)-1-oxaspiro[2.5]octan-6-yl 6-oxa-2-azaspiro[3.4]octane-2-carboxylate | 13.9 | 2.7 | |
| 19 | (3aR,6aS)-((3R,4S,5S,6R)-5-methoxy-4-((2R,3R)-2-methyl-3-(3-methylbut-2-enyl)oxiran-2-yl)-1-oxaspiro[2.5]octan-6-yl) 5-(2,2-difluoroethyl)hexahydropyrrolo[3,4-c]pyrrole-2(1H)-carboxylate | 22.6 | 7.6 | |
| 32 | (1R,5S,6R)-(3R,4S,5S,6R)-5-methoxy-4-((2R,3R)-2-methyl-3-(3-methylbut-2-en-1-yl)oxiran-2-yl)-1-oxaspiro[2.5]octan-6-yl 6-(methylcarbamoyl)-3-azabicyclo[3.1.0]hexane-3-carboxylate | 4 | | |
| 33 | (1R,5S,6R)-(3R,4S,5S,6R)-5-methoxy-4-((2R,3R)-2-methyl-3-(3-methylbut-2-en-1-yl)oxiran-2-yl)-1-oxaspiro[2.5]octan-6-yl 6-(dimethylcarbamoyl)-3-azabicyclo[3.1.0]hexane-3-carboxylate | 13.8 | | |
| 37 | (1R,5S,6R)-(3R,4S,5S,6R)-5-methoxy-4-((2R,3R)-2-methyl-3-(3-methylbut-2-en-1-yl)oxiran-2-yl)-1-oxaspiro[2.5]octan-6-yl 6-((2-morpholinoethyl)carbamoyl)-3-azabicyclo[3.1.0]hexane-3-carboxylate | 4.3 | | |
| 34 | (1R,5S,6R)-(3R,4S,5S,6R)-5-methoxy-4-((2R,3R)-2-methyl-3-(3-methylbut-2-en-1-yl)oxiran-2-yl)-1-oxaspiro[2.5]octan-6-yl 6-carbamoyl-3-azabicyclo[3.1.0]hexane-3-carboxylate | 3 | | |
| 14 | (3R,4S,5S,6R)-5-methoxy-4-((2R,3R)-2-methyl-3-(3-methylbut-2-enyl)oxiran-2-yl)-1-oxaspiro[2.5]octan-6-yl 9-(2,2-difluoroethyl)-3,9-diazaspiro[5.5]undecane-3-carboxylate | 23.3 | 11.6 | |
| 25 | (3R,4S,5S,6R)-5-methoxy-4-((2R,3R)-2-methyl-3-(3-methylbut-2-enyl)oxiran-2-yl)-1-oxaspiro[2.5]octan-6-yl 7-oxo-2,6-diazaspiro[3.4]octane-2-carboxylate | 2 | | |
| 29 | (3R,4S,5S,6R)-5-methoxy-4-((2R,3R)-2-methyl-3-(3-methylbut-2-enyl)oxiran-2-yl)-1-oxaspiro[2.5]octan-6-yl 3-oxo-2,8-diazaspiro[4.5]decane-8-carboxylate | −0.5 | | |

TABLE 2-continued

| Example No. | Compound Name | Mouse @ 0.3 mpk sc (%) | Rat @ 0.3 mpk sc (%) | Rat @ 1.0 mpk sc (%) |
|---|---|---|---|---|
| 40 | (1R,5S,6S)-((3R,4S,5S,6R)-5-methoxy-4-((2R,3R)-2-methyl-3-(3-methylbut-2-enyl)oxiran-2-yl)-1-oxaspiro[2.5]octan-6-yl) 6-(morpholinomethyl)-3-azabicyclo[3.1.0]hexane-3-carboxylate | 11.1 | | |
| 30 | (3R,4S,5S,6R)-5-methoxy-4-((2R,3R)-2-methyl-3-(3-methylbut-2-enyl)oxiran-2-yl)-1-oxaspiro[2.5]octan-6-yl 8-oxo-3,9-diazaspiro[5.5]undecane-3-carboxylate | 1.1 | | |
| 28 | (3R,4S,5S,6R)-5-methoxy-4-((2R,3R)-2-methyl-3-(3-methylbut-2-enyl)oxiran-2-yl)-1-oxaspiro[2.5]octan-6-yl 9-methyl-3,9-diazaspiro[5.5]undecane-3-carboxylate | 8 | | |
| 31 | (3R,4S,5S,6R)-5-methoxy-4-((2R,3R)-2-methyl-3-(3-methylbut-2-enyl)oxiran-2-yl)-1-oxaspiro[2.5]octan-6-yl 9-methyl-8-oxo-3,9-diazaspiro[5.5]undecane-3-carboxylate | 3.6 | | |
| 15 | (3R,4S,5S,6R)-5-methoxy-4-((2R,3R)-2-methyl-3-(3-methylbut-2-enyl)oxiran-2-yl)-1-oxaspiro[2.5]octan-6-yl 2-(2,2-difluoroethyl)-2,6-diazaspiro[3.4]octane-6-carboxylate | 22.5 | | |
| 21 | (3R,4S,5S,6R)-5-methoxy-4-((2R,3R)-2-methyl-3-(3-methylbut-2-enyl)oxiran-2-yl)-1-oxaspiro[2.5]octan-6-yl 3-azabicyclo[3.1.0]hexane-3-carboxylate | 21.2 | | |
| 16 | (3R,4S,5S,6R)-5-methoxy-4-((2R,3R)-2-methyl-3-(3-methylbut-2-enyl)oxiran-2-yl)-1-oxaspiro[2.5]octan-6-yl 8-(2,2-difluoroethyl)-2,8-diazaspiro[4.5]decane-2-carboxylate | 23.4 | | |
| 42 | (3aR,6aS)-2-((3R,4S,5S,6R)-5-methoxy-4-((2R,3R)-2-methyl-3-(3-methylbut-2-enyl)oxiran-2-yl)-1-oxaspiro[2.5]octan-6-yl) 5-methyl tetrahydropyrrolo[3,4-c]pyrrole-2,5(1H,3H)-dicarboxylate | 12.4 | | |
| compound A | [(3R,6R,7S,8S)-7-methoxy-8-[(2R,3R)-2-methyl-3-(3-methylbut-2-enyl)oxiran-2-yl]-2-oxaspiro[2.5]octan-6-yl] (E)-3-[4-[2-(dimethylamino)ethoxy]phenyl]prop-2-enoate | 18.0 | 20.0 | |

Biological Example C

Study Summary HT-1080:

The human fibrosarcoma cell line HT-1080 were grown to almost complete confluence in T75 tissue culture flasks in preparation for the experiment. The cells were trypsinised and re-suspended in complete medium using DMEM plus 9% FBS including penicillin/streptomycin supplements. 500 cells in a total volume of 25 µl were seeded into black walled 384 well plates and returned to a CO2 incubator over-night. Compounds and standards were prepared at 333.3× actual test concentration in neat DMSO. 10 point dose response curves of test compounds were generated by 1:3 serial dilutions, 2 µl of DMSO stock was transferred to 109 µl complete medium. This was further diluted 1:6 in complete medium, with 5 µl of the resulting solution added to the incubated 384 well plate. The assay had a final DMSO concentration of 0.3%, a level which was identified as being non-cytotoxic to the cells. For experimental blanks at the start of the experiment, CellTiter-Glo was added to a satellite plate of cells (identical to the experimental plate), when adding compounds on Day 1. The average of these wells is used as the blanks in the calculation template. Following 72 hours incubation with compounds and standard the plate was removed from the incubator and allowed to equilibrate at room temperature for at least 30 minutes. CellTiter-Glo was thawed and subsequently 30 µl added to columns 2-23. The plate was covered with a clear Perkin Elmer Topseal and placed on a plate shaker for 10-20 mins to aid homogenous mixing. Luminescence per well was determined using an EnVision 2104 Multilabel Reader (PerkinElmer) or other suitable reader. The compound blank value recorded on Day 1 is subtracted from all other data. Data is expressed as % inhibition of mean DMSO control response and the $EC_{50}$ is calculated as 50% maximum response. The $EC_{50}$ values are determined from a sigmoidal 4 parameter curve fit using XLfit in conjunction with Activity Base (IDBS; Guildford, Surrey, UK). The bottom of the curve is fixed to 0% inhibition.

Study Summary Rat Embryofetal:

The objective of this study design was to evaluate the potential effects of disclosed compounds on embryo/fetal development when given subcutaneously to pregnant rats once every three days during the critical period of organogenesis (Gestation Days 6-18). Female, Sprague Dawley rats, approximately 10 weeks of age, time bred, were ordered from a certified vendor and housed individually housed in stainless steel cages suspended over flush pans, on a 12-hour light-dark cycle (0700-1900) at 20-26° C. and 30-70% humidity. Rats were fed a standard rodent chow and provided water ad libitum. Rats were received and housed in the facility for a period of approximately 1 to 2 days.

Compounds were formulated using 100% DMSO mixed in Sterile Water for Injection, resulting in 2% DMSO solution in water. If necessary, due to limited solubility of a test article, a higher percentage of DMSO solution in water was used. Groups of 8 mated and presumed pregnant female rats were given subcutaneous doses of vehicle or test article, once every three days, beginning on Gestation Day 6 and ending on Gestation Day 18 (Days 6, 9, 12, 15, and 18), maintained two more days, and then euthanized and necropsied on Gestation Day 20. Body weights was recorded for all animals on Gestation Days 5 (purpose of randomization), 6, 9, 12, 15, 18, and 20 (scheduled euthanasia). Food consumption by weight was recorded on Gestation Days 6, 9, 12, 15, 18, and 20 (scheduled termination).

At necropsy, the dams were examined visually for external abnormalities including palpable masses. The abdominal, thoracic, and cranial cavities and their contents were examined for abnormalities and findings will be recorded. The reproductive tract were examined to record the number of ovarian corpora lutea, the number and location of uterine implantation sites noting the position of the cervix, and the number of early resorptions, late resorptions, live fetuses, and dead fetuses. For dead fetuses and late resorptions, crown-to-rump length and weight were recorded, if possible, and the fetus was discarded. For viable fetuses, weight, sex, and grossly visible external abnormalities were recorded. Fetuses with external findings involving the head had a fresh visceral evaluation performed on the head to confirm the external finding, if applicable.

The results are summarized in Table 3, below, wherein A represents an $EC_{50}$ of <0.50 nM and B represents an $EC_{50}$ between 0.50 nM and 1.0 nM.

TABLE 3

| Example | HT-1080 EC50 (nM) | Rat Embryofetal @6 mpk |
|---|---|---|
| 2 | A | Positive |
| 22 | A | Negative |
| 27 | A | Positive |
| 9 | A | Positive |
| 4 | A | Negative |
| compound A | B | Positive |

INCORPORATION BY REFERENCE

All publications and patents mentioned herein are hereby incorporated by reference in their entirety for all purposes as if each individual publication or patent was specifically and individually incorporated by reference. In case of conflict, the present application, including any definitions herein, will control.

EQUIVALENTS

While specific embodiments of the subject invention have been discussed, the above specification is illustrative and not restrictive. Many variations of the present disclosure will become apparent to those skilled in the art upon review of this specification. The full scope of the disclosure should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present disclosure.

What is claimed is:
1. A compound represented by:

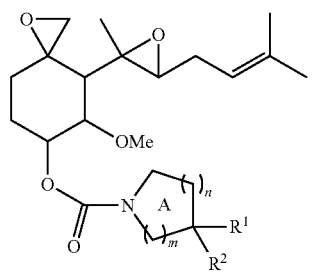

wherein:
n is 0;
m is 1;
$R^1$ and $R^2$, together with the carbon or carbons to which they are attached, form a 4-6 membered saturated heterocyclic ring B having one or two heteroatoms selected from the group consisting of O, $S(O)_w$ (wherein w is 0, 1 or 2) and $NR^h$, or
$R^1$ and $R^2$, together with the carbon or carbons to which they are attached, form a 3-6 membered saturated carbocyclic ring B, wherein carbocyclic ring B may optionally be substituted on a free carbon by one or two substituents each independently selected from the group consisting of halogen, hydroxyl, $C_{1-3}$alkyl, and —$C_{1-6}$alkylene-$NR^iR^j$, wherein $C_{1-3}$alkyl or $C_{1-6}$alkylene-$NR^iR^j$ may optionally be substituted by one or more fluorine atoms;
Ring A may be optionally substituted by a substituent selected from the group consisting of halogen, hydroxyl, and $C_{1-3}$alkyl, wherein $C_{1-3}$alkyl may optionally be substituted by one or more fluorine atoms or a substituent selected from the group consisting of cyano, hydroxyl, and $N(R^aR^b)$;
$R^h$ is independently selected for each occurrence from the group consisting of hydrogen, $C_{1-6}$alkyl, $C_{3-6}$alkenyl, and $C_{3-6}$alkynyl, wherein $C_{1-6}$alkyl, $C_{3-6}$alkenyl, and $C_{3-6}$alkynyl may optionally be substituted by one or more substituents selected from $R^P$;
$R^P$ is independently selected, for each occurrence, from the group consisting of halogen, hydroxyl, cyano, $C_{1-6}$alkoxy, and $R^iR^jN$—;
$R^i$ and $R^j$ are selected independently for each occurrence from the group consisting of hydrogen and $C_{1-6}$alkyl, or $R_i$ and $R_j$ taken together with the nitrogen to which they are attached form a 4-9 membered heterocyclic ring, which may have an additional heteroatom selected from the group consisting of N, O, and $S(O)_w$ (wherein w is 0, 1 or 2), wherein if said 4-9 membered heterocyclic ring contains a —NH moiety that nitrogen may be optionally substituted by a substituent selected from the group consisting of hydrogen, $C_{1-6}$alkyl optionally be substituted by one or more substituents selected from the group consisting of fluorine, hydroxyl, and cyano;

$R^a$ and $R^b$ are independently selected, for each occurrence, from the group consisting of hydrogen and $C_{1-4}$alkyl;

and pharmaceutically acceptable salts and/or stereoisomers thereof.

2. The compound of claim 1, wherein $R^1$ and $R^2$, together with the carbon or carbons to which they are attached, form a 4-membered saturated heterocyclic ring B having one $NR^h$.

3. The compound of claim 1, wherein $R^1$ and $R^2$, together with the carbon or carbons to which they are attached, form a 4 membered saturated heterocyclic ring B having one $S(O)_2$.

4. The compound of claim 1, wherein ring A and ring B, taken together, are selected from the group consisting of:

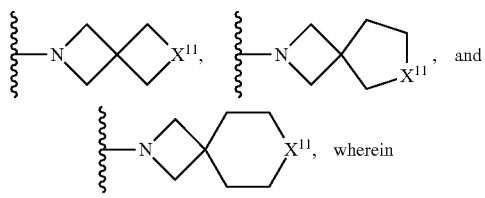, and

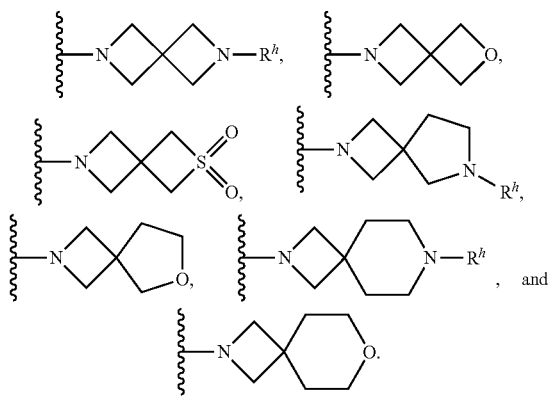, wherein $X^{11}$ is selected from the group consisting of $C(R^{11}R^{22})$, $NR^h$, O, and $S(O)_2$; and $R^{11}$ and $R^{22}$ are each independently selected from the group consisting of hydrogen, halogen, and —$C_{1-6}$alkylene-$NR^iR^j$, wherein $R^i$ and $R^j$ taken together with the nitrogen to which they are attached form a 4-9 membered heterocyclic ring wherein if said heterocyclic ring contains a —NH moiety that nitrogen may be optionally substituted by a substituent $C_{1-6}$alkyl optionally substituted by one or more substituents selected from the group consisting of fluorine, hydroxyl and cyano;

$R^h$ is independently selected for each occurrence from the group consisting of hydrogen, and $C_{1-6}$alkyl, wherein $C_{1-6}$alkyl may optionally be substituted by one or more substituents selected from $R^P$;

$R^P$ is independently selected, for each occurrence, from the group consisting of halogen, hydroxyl, and cyano.

5. The compound of claim 1, wherein ring A and ring B, taken together, are selected from the group consisting of:

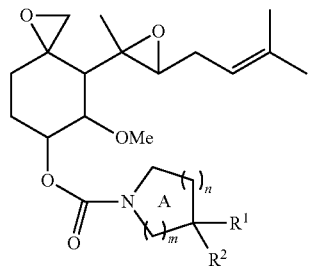

6. The compound of claim 5, wherein $R^h$ is selected from the group consisting of hydrogen and $C_{1-3}$alkyl optionally substituted by one or more fluorine atoms.

7. The compound of claim 5, wherein $R^h$ is selected from the group consisting of hydrogen, methyl,

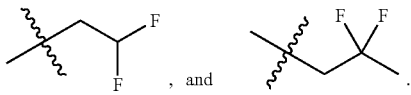

8. The compound of claim 4, wherein ring A and ring B taken together are selected from the group consisting of:

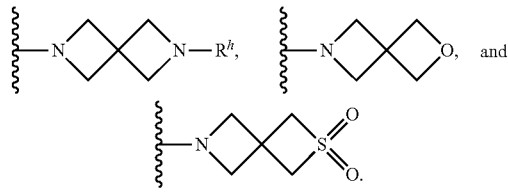

9. The compound of claim 8, wherein $R^h$ is selected from the group consisting of hydrogen, methyl,

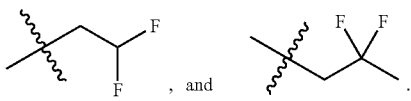

10. A compound represented by:

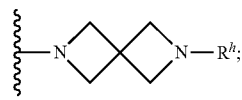

wherein:

n is 0;

m is 1;

$R^1$ and $R^2$, together with the carbon or carbons to which they are attached, form a 4 membered saturated heterocyclic ring B, wherein ring A and B, taken together, are represented by:

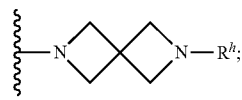

$R^h$ is independently selected for each occurrence from the group consisting of hydrogen and $C_{1-6}$alkyl, wherein $C_{1-6}$alkyl may optionally be substituted by one or more substituents selected from $R^P$;

$R^P$ is independently selected, for each occurrence, from the group consisting of halogen, hydroxyl, and cyano; and pharmaceutically acceptable salts and/or stereoisomers thereof.

11. A compound selected from the group consisting of:

(3R,4S,5S,6R)-5-methoxy-4-((2R,3R)-2-methyl-3-(3-methylbut-2-en-1-yl)oxiran-2-yl)-1-oxaspiro[2.5]octan-6-yl 2-oxa-6-azaspiro[3.3]heptane-6-carboxylate;

(3R,4S,5S,6R)-5-methoxy-4-((2R,3R)-2-methyl-3-(3-methylbut-2-en-1-yl)oxiran-2-yl)-1-oxaspiro[2.5]octan-6-yl 7-oxa-2-azaspiro[3.5]nonane-2-carboxylate;

(3R,4S,5S,6R)-5-methoxy-4-((2R,3R)-2-methyl-3-(3-methylbut-2-en-1-yl)oxiran-2-yl)-1-oxaspiro[2.5]octan-6-yl 6-oxa-2-azaspiro[3.4]octane-2-carboxylate;

(3R,4S,5S,6R)-5-methoxy-4-((2R,3R)-2-methyl-3-(3-methylbut-2-en-1-yl)oxiran-2-yl)-1-oxaspiro[2.5]octan-6-yl 7-methyl-2,7-diazaspiro[3.5]nonane-2-carboxylate;

(3R,4S,5S,6R)-5-methoxy-4-((2R,3R)-2-methyl-3-(3-methylbut-2-en-1-yl)oxiran-2-yl)-1-oxaspiro[2.5]octan-6-yl 7-(2,2-difluoroethyl)-2,7-diazaspiro[3.5]nonane-2-carboxylate;

(3R,4S,5S,6R)-5-methoxy-4-((2R,3R)-2-methyl-3-(3-methylbut-2-en-1-yl)oxiran-2-yl)-1-oxaspiro[2.5]octan-6-yl 6-methyl-2,6-diazaspiro[3.3]heptane-2-carboxylate;

(3R,4S,5S,6R)-5-methoxy-4-((2R,3R)-2-methyl-3-(3-methylbut-2-en-1-yl)oxiran-2-yl)-1-oxaspiro[2.5]octan-6-yl 6-(2,2-difluoroethyl)-2,6-diazaspiro[3.4]octane-2-carboxylate;

(3R,4S,5S,6R)-5-methoxy-4-((2R,3R)-2-methyl-3-(3-methylbut-2-en-1-yl)oxiran-2-yl)-1-oxaspiro[2.5]octan-6-yl 6-(2,2-difluoroethyl)-2,6-diazaspiro[3.3]heptane-2-carboxylate;

(3R,4S,5S,6R)-5-methoxy-4-((2R,3R)-2-methyl-3-(3-methylbut-2-en-1-yl)oxiran-2-yl)-1-oxaspiro[2.5]octan-6-yl 2-thia-6-azaspiro[3.3]heptane-6-carboxylate 2,2-dioxide;

(3R,4S,5S,6R)-5-methoxy-4-((2R,3R)-2-methyl-3-(3-methylbut-2-en-1-yl)oxiran-2-yl)-1-oxaspiro[2.5]octan-6-yl 6-(morpholinomethyl)-2-azaspiro[3.3]heptane-2-carboxylate;

(3R,4S,5S,6R)-5-methoxy-4-((2R,3R)-2-methyl-3-(3-methylbut-2-en-1-yl)oxiran-2-yl)-1-oxaspiro[2.5]octan-6-yl 6-((4-(2,2-difluoroethyl)piperazin-1-yl)methyl)-2-azaspiro[3.3]heptane-2-carboxylate;

and a pharmaceutically acceptable salt or stereoisomer thereof.

12. The compound (3R,4S,5S,6R)-5-methoxy-4-((2R,3R)-2-methyl-3-(3-methylbut-2-en-1-yl)oxiran-2-yl)-1-oxaspiro[2.5]octan-6-yl 6-(2,2-difluoroethyl)-2,6-diazaspiro[3.3]heptane-2-carboxylate or pharmaceutically acceptable salts thereof.

13. A pharmaceutically acceptable composition comprising a compound of claim 12 and a pharmaceutically acceptable excipient.

14. A pharmaceutically acceptable composition comprising a compound of claim 1 and a pharmaceutically acceptable excipient.

* * * * *